US006680313B2

(12) United States Patent
Kano et al.

(10) Patent No.: US 6,680,313 B2
(45) Date of Patent: Jan. 20, 2004

(54) CARBAPENUM DERIVATIVES

(75) Inventors: Yuko Kano, Yokohama (JP); Takahisa Maruyama, Yokohama (JP); Yumiko Sambongi, Yokohama (JP); Kazuhiro Aihara, Yokohama (JP); Kunio Atsumi, Yokohama (JP); Kastuyoshi Iwamatsu, Yokohama (JP); Takashi Ida, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 10/182,179
(22) PCT Filed: Jan. 26, 2001
(86) PCT No.: PCT/JP01/00528
§ 371 (c)(1), (2), (4) Date: Jul. 25, 2002
(87) PCT Pub. No.: WO01/55154
PCT Pub. Date: Aug. 2, 2001

(65) Prior Publication Data
US 2003/0027809 A1 Feb. 6, 2003

(30) Foreign Application Priority Data
Jan. 26, 2000 (JP) .......................................... 2000-17290
(51) Int. Cl.[7] ................... C07D 519/06; A61K 31/429; A61P 31/04
(52) U.S. Cl. ................... 514/210.14; 540/302
(58) Field of Search ...................... 514/210.14; 540/302

(56) References Cited
U.S. PATENT DOCUMENTS
6,458,780 B1 * 10/2002 Kano et al. ................. 540/302

FOREIGN PATENT DOCUMENTS

| WO | 96/28455 | 9/1996 | | |
|---|---|---|---|---|
| WO | 98/23623 | 6/1998 | | |
| WO | 98/32760 | 7/1998 | | |
| WO | 00/06581 | 2/2000 | | |
| WO | WO 200155155 A1 * | 8/2001 | ......... | A61K/31/429 |
| WO | WO 200242312 A1 * | 5/2002 | ......... | A61K/31/429 |

* cited by examiner

Primary Examiner—Mark L. Berch
(74) Attorney, Agent, or Firm—Wenderoth, Lind & Ponack, L.L.P.

(57) ABSTRACT

An objective of the present invention is to provide carbapenem derivatives which have potent antibiotic activity against MRSA, PRSP, Influenzavirus, and β-lactamase-producing bacteria and are stable against DHP-1. The compounds according to the present invention are compounds represented by formula (I) or pharmaceutically acceptable salts thereof:

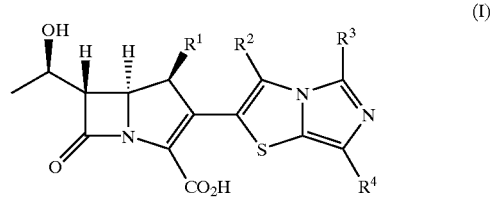

wherein $R^1$ represents H or methyl; $R^2$ and $R^3$ represent H, a halogen atom, alkyl or the like; and $R^4$ represents substituted lower alkylthio or the like.

11 Claims, No Drawings

CARBAPENUM DERIVATIVES

BACKGROUND OF THE INVENTION

1. Field of the Invention

The present invention relates to novel carbapenem derivatives which have excellent antibiotic activity against a wide spectrum of bacteria, and more particularly to novel carbapenem derivatives which have a substituted imidazo[5,1-b]thiazole group at the 2-position on the carbapenem ring.

2. Background Art

Carbapenem derivatives, by virtue of potent antibiotic activity against a wide spectrum of bacteria, have been energetically studied as a highly useful β-lactam agent, and Imipenem, Panipenem, and Meropenem have already been clinically used.

At the present time, both Imipenem and Panipenem, however, are used as a mixture due to instability against renal dehydropeptidase-1 (hereinafter abbreviated to "DHP-1") in the case of Imipenem and in order to reduce nephrotoxicity in the case of Panipenem. Meropenem which has recently been marketed has a methyl group at the 1β-position, so that it has increased stability against DHP-1 and thus can be used alone. The stability against DHP-1, however, is still unsatisfactory. The antibiotic activity also is not necessarily satisfactory against methicillin resistant *Staphylococcus aureus* (hereinafter abbreviated to "MRSA"), penicillin resistant *Streptococcus pneumoneae* (hereinafter abbreviated to "PRSP"), resistant *Pseudomonas aeruginosa*, enterococci, and Influenzavirus which currently pose serious clinical problems. Therefore, drugs useful for these bacteria responsible for infectious diseases have been desired in the art.

WO 96/28455 describes carbapenem derivatives having a novel aromatic heterocyclic imidazo[5,1-b]thiazolium-6-ylmethyl group at the 2-position of the carbapenem ring, WO 98/23623 describes carbapenem derivatives having an imidazo[5,1-b]thiazole group through a pyrrolidinylthio group at the 2-position of the carbapenem ring, and WO 98/32760 describes derivatives with a carbon atom on an imidazo[5,1-b]thiazole group being attached to the 2-position of the carbapenem ring.

SUMMARY OF THE INVENTION

An object of the present invention is to provide carbapenem derivatives which have potent antibiotic activity against MRSA, PRSP, Influenzavirus, and β-lactamase-producing bacteria and are stable against DHP-1.

According to one aspect of the present invention, there is provided a compound represented by formula (I) or a pharmaceutically acceptable salt thereof:

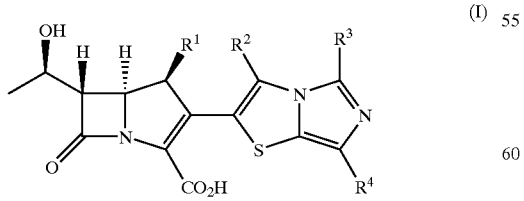

(I)

wherein
$R^1$ represents a hydrogen atom or methyl;
$R^2$ and $R^3$, which may be the same or different, represent a hydrogen atom,
a halogen atom,
lower alkyl on which one or more hydrogen atoms may be substituted by hydroxyl or amino,
lower alkylcarbonyl,
carbamoyl,
aryl, or
lower alkylthio; and
$R^4$ represents
substituted lower alkylthio wherein one or more substituents of the alkyl portion, which may be the same or different, are selected from the group consisting of a halogen atom, nitro, azido, cyano, lower cycloalkyl, isothioureido, hydroxyl, lower alkoxy, phosphonoxy, formyl, lower alkylcarbonyl, arylcarbonyl, carboxy, lower alkoxycarbonyl, carbamoyl, N-lower alkylcarbamoyl, N,N-di-lower alkylcarbamoyl, amino, N-lower alkylamino, N,N-di-lower alkylamino, formylamino, lower alkylcarbonylamino, aminosulfonylamino, (N-lower alkylamino)sulfonylamino, (N,N-di-lower alkylamino)sulfonylamino, formimidoylamino, acetimidoylamino, guanidino, amindsulfonyl, (N-lower alkylamino)sulfonyl, (N,N-di-lower alkylamino)sulfonyl, aryl, a monocyclic or bicyclic heterocyclic ring containing one or more hetero atoms, which may be the same or different, pyridinium-1-yl, 1-azonia-4-azabicyclo[2,2,2]oct-1-yl, and 4-lower alkyl-1,4-diazoniabicyclo[2,2,2]oct-1-yl wherein the lower alkyl portion may be substituted by one or more groups selected from the group consisting of a halogen atom, hydroxyl, carbamoyl, and amino,
lower cycloalkylthio wherein one or more hydrogen atoms of the cycloalkyl portion may be substituted by a group selected from the group consisting of a halogen atom, nitro, cyano, hydroxyl, carbamoyl, and amino,
$C_{2-4}$ alkenylthio,
$C_{2-4}$ alkynylthio,
substituted arylthio wherein one or more substituents of the aryl portion, which may be the same or different, are selected from the group consisting of a halogen atom, nitro, cyano, hydroxyl, carbamoyl, and amino,
thio substituted by a monocyclic or bicyclic heterocyclic ring containing one or more hetero atoms which may be the same or different, wherein, when the ring contains a nitrogen atom, lower alkyl optionally having carbamoyl may be attached to the nitrogen atom and the nitrogen atom may be in the form of a quaternary ammonium atom,
substituted lower alkylsulfinyl wherein one or more substituents of the alkyl portion, which may be the same or different, are selected from the group consisting of a halogen atom, hydroxyl, carbamoyl, and amino,
substituted lower alkylsulfonyl wherein one or more substituents of the alkyl portion, which may be the same or different, are selected from the group consisting of a halogen atom, hydroxyl, carbamoyl, and amino, or
sulfonyl substituted by a monocyclic or bicyclic heterocyclic ring containing one or more hetero atoms which may be the same or different, wherein, when the ring contains a nitrogen atom, lower alkyl optionally having carbamoyl may be attached to the nitrogen atom and the nitrogen atom may be in the form of a quaternary ammonium atom.

The carbapenem derivatives represented by formula (I) have potent antibiotic activities against a wide spectrum of Gram-positive bacteria and Gram-negative bacteria. The compounds represented by formula (I) have potent antibiotic activity particularly against MRSA, PRSP, Influenzavirus, and β-lactamase-producing bacteria. The carbapenem derivatives of the present invention advantageously have low toxicity and high safety.

DETAILED DESCRIPTION OF THE INVENTION

As used herein, the term "lower alkyl" or "lower alkoxy" as a group or a part of a group means straight-chain or branched $C_{1-6}$, preferably $C_{1-4}$, alkyl or alkyloxy. Examples of the lower alkyl include methyl, ethyl, n-propyl, i-propyl, n-butyl, i-butyl, s-butyl, t-butyl, n-pentyl, and n-hexyl. Examples of the lower alkoxy include methoxy, ethoxy, n-propoxy, i-propoxy, n-butoxy, s-butoxy, and t-butoxy.

The term "lower cycloalkyl" means $C_{3-6}$ monocyclic alkyl.

The term "halogen atom" means a fluorine, chlorine, bromine, or iodine atom.

The term "aryl" as a group or a part of a group means a six- to 10-membered monocyclic or bicyclic aromatic carbocyclic ring, and examples thereof include phenyl and naphthyl with phenyl being preferred.

The term "hetero atom" as used herein means a nitrogen atom, an oxygen atom, or a sulfur atom.

The "monocyclic or bicyclic heterocyclic ring containing one or more hetero atoms" preferably means a five- to 12-membered monocyclic or bicyclic saturated or unsaturated heterocyclic ring containing 1 to 4 hetero atoms. The hetero atom constituting the heterocyclic ring is preferably one or two nitrogen atoms.

Examples of the heterocyclic ring include pyrrolidine, piperidine, and pyridine.

$R^1$ preferably represents methyl.

$R^2$ and $R^3$, which may be the same or different, preferably represent a hydrogen atom or lower alkylthio, more preferably a hydrogen atom or methylthio, particularly preferably a hydrogen atom.

$R^4$ preferably represents substituted lower alkylthio wherein one or more substituents of the alkyl portion, which may be the same or different, are selected from the group consisting of a halogen atom, azido, isothioureido, hydroxyl, phosphonoxy, lower alkylcarbonyl, carbamoyl, amino, formylamino, aminosulfonylamino, (N,N-di-lower alkylamino)sulfonylamino, formimidoylamino, acetimidoylamino amino, guanidino, aryl, a pyridine ring, pyridinium-1-yl, 1-azonia-4-azabicyclo[2,2,2]oct-1-yl, and 4-lower alkyl-1,4-diazoniabicyclo[2,2,2]oct-1-yl in which lower alkyl may be substituted by one or more groups selected from the group consisting of a halogen atom, hydroxyl, carbamoyl, and amino, thio substituted by a heterocyclic ring selected from the group consisting of pyrrolidine, piperidine, and pyridine, wherein lower alkyl optionally having carbamoyl may be attached to the nitrogen atom in the ring and the nitrogen atom may be in the form of a quaternary ammonium atom, lower alkylsulfinyl optionally substituted by hydroxyl, lower alkylsulfonyl optionally substituted by hydroxyl, or sulfonyl substituted by a heterocyclic ring selected from the group consisting of pyrrolidine, piperidine, and pyridine, wherein lower alkyl optionally having carbamoyl may be attached to the nitrogen atom in the ring and the nitrogen atom may be in the form of a quaternary ammonium atom.

$R^4$ more preferably represents trifluoromethylthio, 2-fluoroethylthio, 2-bromoethylthio, 2-azidoethylthio, 2-(isothioureidoethyl)thio, 2-hydroxyethylthio, (2R)-2,3-dihydroxypropylthio, 2-phosphonoxyethylthio, 2-oxopropylthio, carbamoylmethylthio, 2-aminoethylthio, 3-aminopropylthio, 6-aminohexylthio, (2R)-3-amino-2-hydroxypropylthio, 2-formylaminoethylthio, 2-(aminosulfonylamino)ethylthio, 2-[(N,N-dimethylamino)sulfonyl-amino]ethylthio, 2-(formimidoylamino)ethylthio, 2-(acetimidoylamino)ethylthio, 3-(acetimidoylamino) propylthio, 2-guanidinoethylthio, 3-guanidinopropylthio, benzylthio, (pyridin-2-yl)methylthio, 2-(pyridinium-1-yl) ethylthio, 2-(1-azonia-4-azabicyclo[2,2,2]oct-1-yl) ethylthio, (3S)-3-pyrrolidinylthio, 4-piperidinylthio, (pyridin-2-yl)thio, (pyridin-4-yl)thio, (1-carbamoylmethylpyridinium-2-yl)thio, 2-hydroxyethylsulfinyl, 2-hydroxyethylsulfonyl, or (pyridin-4-yl)sulfonyl. Among them, substituted lower alkylthio is more preferred, and guanidino-substituted lower alkylthio or pyrrolidinylthio is particularly preferred.

Among the compounds represented by formula (I), a group of preferred compounds include those wherein $R^4$ represents substituted lower alkylthio, thio substituted by a monocyclic or bicyclic heterocyclic ring containing one or more hetero atoms which may be the same or different, substituted lower alkylsulfinyl, substituted lower alkylsulfonyl, or sulfonyl substituted by a monocyclic or bicyclic heterocyclic ring containing one or more hetero atoms which may be the same or different, wherein, when the ring contains a nitrogen atom, lower alkyl optionally having carbamoyl may be attached to the nitrogen atom and the nitrogen atom may be in the form of a quaternary ammonium atom.

Another group of preferred compounds include those wherein $R^4$ represents substituted lower alkylthio, optionally substituted lower cycloalkylthio, $C_{2-4}$ alkenylthio, $C_{2-4}$ alkynylthio, substituted arylthio, thio substituted by a monocyclic or bicyclic heterocyclic ring containing one or more hetero atoms which may be the same or different, substituted lower alkylsulfinyl, or substituted lower alkylsulfonyl.

A group of more preferred compounds include those wherein $R^1$ represents a hydrogen atom or methyl, $R^2$ and $R^3$, which may be the same or different, represent a hydrogen atom or lower alkylthio, and $R^4$ represents substituted lower alkylthio wherein one or more substituents thereof are selected from the group consisting of a halogen atom, azido, isothioureido, hydroxyl, phosphonoxy, lower alkylcarbonyl, carbamoyl, amino, formylamino, aminosulfonylamino, (N,N-di-lower alkylamino) sulfonyl-amino, formimidoylamino, acetimidoylamino, guanidino, aryl, pyridyl, pyridinium-1-yl, 1-azonia-4-azabicyclo[2,2,2]oct-1-yl, and 4-lower alkyl-1,4-diazoniabicyclo[2,2,2]oct-1-yl in which lower alkyl may be substituted by one or more groups selected from the group consisting of a halogen atom, hydroxyl, carbamoyl, and amino, thio substituted by a heterocyclic ring selected from the group consisting of pyrrolidine, piperidine, and pyridine, wherein lower alkyl optionally having carbamoyl may be attached to the nitrogen atom in the ring and the nitrogen atom may be in the form of a quaternary ammonium atom, lower alkylsulfinyl optionally substituted, by hydroxyl,
lower alkylsulfonyl optionally substituted by hydroxyl, or sulfonyl substituted by a heterocyclic ring selected from the group consisting of pyrrolidine, piperidine, and pyridine, wherein lower alkyl optionally having carbamoyl may be attached to the nitrogen atom in the ring and the nitrogen atom may be in the form of a quaternary ammonium atom.

Another group of more preferred compounds include those wherein $R^1$ represents a hydrogen atom or methyl, $R^2$ and $R^3$, which may be the same or different, represent a hydrogen atom or lower alkylthio, and $R^4$ represents substituted lower alkylthio wherein one or more substituents thereof are selected from the group consisting of a halogen atom, azido, isothioureido, hydroxyl, phosphonoxy, lower alkylcarbonyl, carbamoyl, amino, formylamino, aminosulfonylamino, (N,N-di-lower alkylamino)sulfonyl-amino, formimidoylamino, acetimidoylamino, guanidino, aryl, pyridyl, pyridinium-1-yl, 1-azonia-4-azabicyclo[2,2,2]oct-1-yl, and 4-lower alkyl-1,4-diazoniabicyclo[2,2,2]oct-1-yl in which one or more hydrogen atoms on lower alkyl may be substituted by a halogen atom, hydroxyl, carbamoyl, or amino.

A group of further preferred compounds include those wherein $R^1$ represents methyl and $R^2$ and $R^3$ represent a hydrogen atom.

A group of particularly preferred compounds include those wherein $R^1$ represents methyl, $R^2$ and $R^3$ represent a hydrogen atom and $R^4$ represents amino or guanidino-substituted lower alkylthio or pyrrolidinylthio, more preferably those wherein $R^1$ represents methyl, $R^2$ and $R^3$ represent a hydrogen atom and $R^4$ represents 2-aminoethylthio, 2-guanidinoethylthio, or (3S)-pyrrolidin-3-ylthio.

Salts of the compounds represented by formula (I) are pharmaceutically acceptable salts, and include, for example, inorganic salts, such as lithium, sodium, potassium, calcium, and magnesium salts, ammonium salts, salts with organic bases, such as triethylamine and diisopropylethylamine, salts with mineral acids, such as hydrochloric acid, sulfuric acid, phosphoric acid, and nitric acid, or salts with organic acids, such as acetic acid, carbonic acid, citric acid, malic acid, oxalic acid, and methanesulfonic acid. Preferred are sodium salts, potassium salts, and hydrochlorides.

Specific examples of carbapenem derivatives represented by formula (I) according to the present invention include, but are not limited to:

1. sodium (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate;
2. sodium (1S,5R,6S)-6-((1R)-1-hydroxyethyl)-2-[7-(2-hydroxyethyl)sulfinylimidazo[5,1-b]thiazol-2-yl]-1-methyl-1-carbapen-2-em-3-carboxylate (a mixture of diastereomers);
3. sodium (1S,5R,6S)-6-((1R)-1-hydroxyethyl)-2-[7-(2-hydroxyethyl)sulfonylimidazo[5,1-b]thiazol-2-yl]-1-methyl-1-carbapen-2-em-3-carboxylate;
4. sodium (5R,6S)-6-((1R)-1-hydroxyethyl)-2-[7-(2-hydroxyethyl)thioimidazo[5,1-b]thiazol-2-yl]-1-carbapen-2-em-3-carboxylate;
5. sodium (1S,5R,6S)-2-[7-(2-aminoethyl)thioimidazo[5,1-b]thiazol-2-yl]-6-((1R)-1-hydroxyethyl)-1-methyl-1-carbapen-2-em-3-carboxylate;
6. sodium (1S,5R,6S)-6-((1R)-1-hydroxyethyl)-1-methyl-2-[7-(2-phosphonoxyethyl)thioimidazo[5,1-b]thiazol-2-yl]-1-carbapen-2-em-3-carboxylate;
7. sodium (1S,5R,6S)-2-[7-(2-azidoethyl)thioimidazo[5,1-b]thiazol-2-yl]-6-((1R)-1-hydroxyethyl)-1-methyl-1-carbapen-2-em-3-carboxylate;
8. sodium (5R,6S)-2-[7-(2-aminoethyl)thioimidazo[5,1-b]thiazol-2-yl]-6-((1R)-1-hydroxyethyl)-1-carbapen-2-em-3-carboxylate;
9. sodium (1S,5R,6S)-2-(7-carbamoylmethylthio-5-methylthioimidazo[5,1-b]thiazol-2-yl)-6-((1R)-1-hydroxyethyl)-1-methyl-1-carbapen-2-em-3-carboxylate;
10. (1S,5R,6S)-6-((1R)-1-hydroxyethyl)-1-methyl-2-[7-[2-(pyridinium-1-yl)ethyl]thioimidazo[5,1-b]thiazol-2-yl]-1-carbapen-2-em-3-carboxylate (intramolecular salt);
11. (5R,6S)-6-((1R)-1-hydroxyethyl)-2-[7-[2-(pyridinium-1-yl)ethyl]thioimidazo[5,1-b]thiazol-2-yl]-1-carbapen-2-em-3-carboxylate (intramolecular salt);
12. sodium (1S,5R,6S)-2-[7-(2-formimidoylaminoethyl)thioimidazo[5,1-b]thiazol-2-yl]-6-((1R)-1-hydroxyethyl)-1-methyl-1-carbapen-2-em-3-carboxylate;
13. sodium (1S,5R,6S)-2-[7-(2-acetimidoylaminoethyl)thioimidazo[5,1-b]thiazol-2-yl]-6-((1R)-1-hydroxyethyl)-1-methyl-1-carbapen-2-em-3-carboxylate;
14. sodium (1S,5R,6S)-2-[7-(2-fluoroethyl)thioimidazo[5,1-b]thiazol-2-yl]-6-((1R)-1-hydroxyethyl)-1-methyl-1-carbapen-2-em-3-carboxylate;
15. sodium (1S,5R,6S)-6-((1R)-1-hydroxyethyl)-1-methyl-2-[5-methylthio-7-(2-phosphonoxyethyl)thioimidazo[5,1-b]thiazol-2-yl]-1-carbapen-2-em-3-carboxylate;
16. sodium (1S,5R,6S)-6-((1R)-1-hydroxyethyl)-2-[7-(2-hydroxyethyl)thio-5-methylthioimidazo[5,1-b]thiazol-2-yl]-1-methyl-1-carbapen-2-em-3-carboxylate;
17. sodium (1S,5R,6S)-2-[7-(2-aminoethyl)thio-5-methylimidazo[5,1-b]thiazol-2-yl]-6-((1R)-1-hydroxyethyl)-1-methyl-1-carbapen-2-em-3-carboxylate;
18. sodium (1S,5R,6S)-2-[7-(2-formylaminoethyl)-thioimidazo[5,1-b]thiazol-2-yl]-6-((1R)-1-hydroxyethyl)-1-methyl-1-carbapen-2-em-3-carboxylate;
19. sodium (1S,5R,6S)-2-[7-(3-aminopropyl)thioimidazo[5,1-b]thiazol-2-yl]-6-((1R)-1-hydroxyethyl)-1-methyl-1-carbapen-2-em-3-carboxylate;
20. sodium (1S,5R,6S)-2-[7-(2-guanidinoethyl)-thioimidazo[5,1-b]thiazol-2-yl]-6-((1R)-1-hydroxyethyl)-1-methyl-1-carbapen-2-em-3-carboxylate;

21. sodium (1S,5R,6S)-2-[7-(3-acetimidoylaminopropyl)thioimidazo[5,1-b]thiazol-2-yl]-6-((1R)-1-hydroxyethyl)-1-methyl-1-carbapen-2-em-3-carboxylate;
22. (1S,5R,6S)-2-[7-(6-aminohexyl)thioimidazo[5,1-b]thiazol-2-yl]-6-((1R)-1-hydroxyethyl)-1-methyl-1-carbapen-2-em-3-carboxylic acid;
23. sodium (1S,5R,6S)-6-((1R)-1-hydroxyethyl)-1-methyl-2-[7-((3S)-pyrrolidin-3-yl)thioimidazo[5,1-b]-thiazol-2-yl]-1-carbapen-2-em-3-carboxylate;
24. sodium (1S,5R,6S)-6-((1R)-1-hydroxyethyl)-1-methyl-2-(7-trifluoromethylthioimidazo[5,1-b]thiazol-2-yl)-1-carbapen-2-em-3-carboxylate;
25. (1S,5R,6S)-2-(7-carbamoylmethylthioimidazo-[5,1-b]thiazol-2-yl)-6-((1R)-1-hydroxyethyl)-1-methyl-1-carbapen-2-em-3-carboxylic acid;
26. (1S,5R,6S)-2-[7-(2-aminosulfonylaminoethyl)-thioimidazo[5,1-b]thiazol-2-yl]-6-((1R)-1-hydroxyethyl)-1-methyl-1-carbapen-2-em-3-carboxylic acid;
27. sodium (1S,5R,6S)-6-((1R)-1-hydroxyethyl)-1-methyl-2-[7-(piperidin-4-yl)thioimidazo[5,1-b]thiazol-2-yl]-1-carbapen-2-em-3-carboxylate;
28. sodium (1S,5R,6S)-2-[7-(2-N,N-dimethylaminosulfonylaminoethyl)thioimidazo[5,1-b]thiazol-2-yl]-6-((1R)-1-hydroxyethyl)-1-methyl-1-carbapen-2-em-3-carboxylate;
29. (1S,5R,6S)-2-[7-[2-(1-azonia-4-azabicyclo-[2,2,2]oct-1-yl)ethyl]thioimidazo[5,1-b]thiazol-2-yl]-6-((1R)-1-hydroxyethyl)-1-methyl-1-carbapen-2-em-3-carboxylate (intramolecular salt) hydrochloride;
30. (1S,5R,6S)-2-[7-(3-guanidinopropyl)thioimidazo-[5,1-b]thiazol-2-yl]-6-((1R)-1-hydroxyethyl)-1-methyl-1-carbapen-2-em-3-carboxylic acid;
31. sodium (1S,5R,6S)-2-[7-(2-bromoethyl)thioimidazo[5,1-b]thiazol-2-yl]-6-((1R)-1-hydroxyethyl)-1-methyl-1-carbapen-2-em-3-carboxylate;
32. sodium (1S,5R,6S)-2-(7-benzylthioimidazo-[5,1-b]thiazol-2-yl)-6-((1R)-1-hydroxyethyl)-1-methyl-1-carbapen-2-em-3-carboxylate;
33. (1S,5R,6S)-6-((1R)-1-hydroxyethyl)-2-[7-(2-isothioureidoethyl)thioimidazo[5,1-b]thiazol-2-yl]-1-methyl-1-carbapen-2-em-3-carboxylic acid;
34. sodium (1S,5R,6S)-6-((1R)-1-hydroxyethyl)-1-methyl-2-[7-(pyridin-2-yl)methylthioimidazo[5,1-b]-thiazol-2-yl]-1-carbapen-2-em-3-carboxylate;
35. sodium (1S,5R,6S)-6-((1R)-1-hydroxyethyl)-1-methyl-2-[7-(pyridin-2-yl)thioimidazo[5,1-b]thiazol-2-yl]-1-carbapen-2-em-3-carboxylate;
36. (1S,5R,6S)-2-[7-(1-carbamoylmethylpyridinium-2-yl)thioimidazo[5,1-b]thiazol-2-yl]-6-((1R)-1-hydroxyethyl)-1-methyl-1-carbapen-2-em-3-carboxylate (intramolecular salt);
37. sodium (1S,5R,6S)-2-[7-((2R)-2,3-dihydroxypropyl)thioimidazo[5,1-b]thiazol-2-yl]-6-((1R)-1-hydroxyethyl)-1-methyl-1-carbapen-2-em-3-carboxylate;
38. sodium (1S,5R,6S)-6-((1R)-1-hydroxyethyl)-1-methyl-2-[7-(2-oxopropyl)thioimidazo[5,1-b]thiazol-2-yl]-1-carbapen-2-em-3-carboxylate;
39. sodium (1S,5R,6S)-2-[7-((2R)-3-amino-2-hydroxypropyl)thioimidazo[5,1-b]thiazol-2-yl]-6-((1R)-1-hydroxyethyl)-1-methyl-1-carbapen-2-em-3-carboxylate;
40. sodium (1S,5R,6S)-6-((1R)-1-hydroxyethyl)-1-methyl-2-[7-(pyridin-4-yl)thioimidazo[5,1-b]thiazol-2-yl]-1-carbapen-2-em-3-carboxylate; and
41. sodium (1S,5R,6S)-6-((1R)-1-hydroxyethyl)-1-methyl-2-[7-(pyridin-4-yl)sulfonylimidazo[5,1-b]thiazol-2-yl]-1-carbapen-2-em-3-carboxylate.

The compounds represented by formula (I) according to the present invention are preferably produced according to the following scheme:

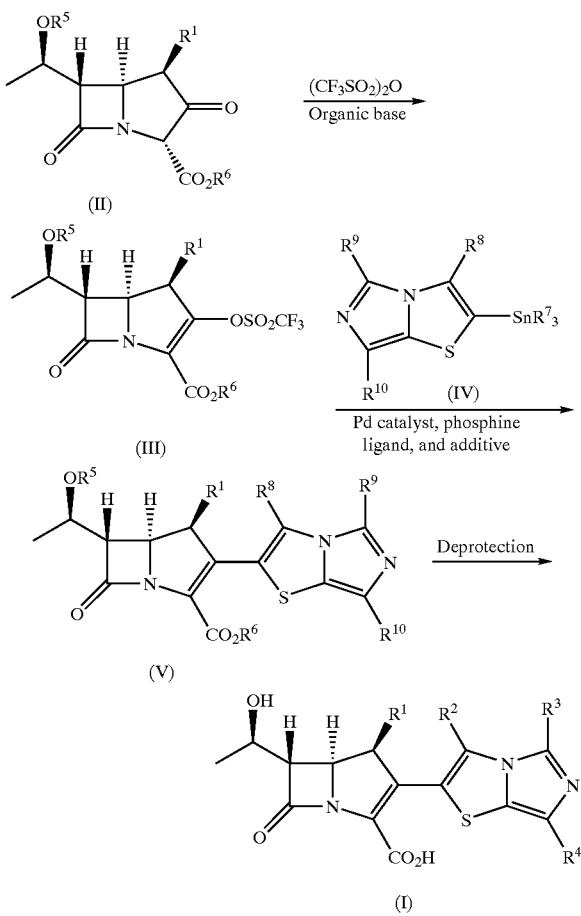

wherein $R^1$, $R^2$, $R^3$, and $R^4$ each have the same meaning as defined in formula (I), $R^5$ represents a hydrogen atom or a protective group of hydroxyl, for example, t-butyldimethylsilyl, trimethylsilyl, triethylsilyl, 4-nitrobenzyloxycarbonyl, 4-methoxybenzyloxycarbonyl, or allyloxycarbonyl; $R^6$ represents a protective group of carboxyl, for example, 4-nitrobenzyl, 4-methoxybenzyl, diphenylmethyl, t-butyldimethylsilyl, or allyl; $R^7$ represents lower alkyl, preferably n-butyl or methyl; $R^8$ and $R^9$ have the same meaning as $R^2$ and $R^3$ or represent a group in which a functional group, for example, hydroxyl, amino, or carboxyl, contained in $R^2$ and $R^3$ has been protected by a conventional protective group; and $R^{10}$ has the same meaning as $R^4$ or represents a group in which a functional group, for example, hydroxyl, amino, or carboxyl, contained, in $R^4$ has been protected by a conventional protective group. The term "conventional protective group" as used herein refers to a protective group described in Protective Groups in organic Synthesis, Theodora W. Greene and Peter G. M. Wuts, published by John Wiley & Sons, Inc.

The compound of formula (II) indicated in the scheme in the first step can be synthesized by the conventional process, and the tin compound of formula (IV) indicated in the scheme in the second step can be synthesized by a process described in WO 98/32760.

In the first step, the compound of formula (II) can be converted to the compound of formula (III) by the following method. Specifically, the compound of formula (II) is reacted with one equivalent or an excessive amount of trifluoromethanesulfonic anhydride in the presence of an organic base, preferably diisopropylethylamine, in an amount of one equivalent or an excessive amount relative to trifluoromethanesulfonic anhydride in an inert solvent, such as acetonitrile, tetrahydrofuran, dichloromethane, or toluene or a mixed solvent composed of the above inert solvents, at a temperature of −50° C. to +50° C. for 10 min to 24 hr, followed by conventional separation and purification to give the compound of formula (III).

Next, in the second step, the compound of formula (III) can be converted to the compound of formula (V) by the following method. Specifically, the compound of formula (III) is reacted with one equivalent or an excessive amount of the compound of formula (IV) in the presence of 0.001 to 1 equivalent of a palladium catalyst, for example, tetrakis(triphenylphosphine)palladium(0), tris(dibenzylideneacetone)dipalladium(0), or tris(dibenzylideneacetone)dipalladium(0)-chloroform adduct, 0.01 to 1 equivalent of a phosphine ligand, for example, triphenylphosphine, tri-2-furylphosphine, tri-2-thienylphosphine, or tris(2,4,6-trimethoxyphenyl)-phosphine, and 1 to 10 equivalents of an additive, for example, zinc chloride, lithium chloride, or cesium fluoride alone or in combination thereof, in an inert solvent, for example, tetrahydrofuran, dimethoxyethane, dioxane, acetonitrile, acetone, ethanol, dimethylsulfoxide, sulfolane, N,N-dimethylformamide, N,N-dimethylacetamide, N-methylpyrrolidinone, or hexamethylphosphoric triamide or a mixed solvent composed of the above inert solvents, at 0° C.–100° C. for 10 min to 7 days, followed by conventional post-treatment to give the compound of formula (V).

Finally, in the third step, the protective group in the compound of formula (V) may be removed by a deprotection reaction in one stage or plural stages depending on the kinds of the protective groups to give the compound of formula (I).

In this case, the deprotection reaction for removing the protective group may be carried out by conventional methods commonly known in the art, although it varies depending upon the kinds of protective groups used. When any one of or all the protective groups can be removed under acidic conditions, a mineral acid such as hydrochloric acid, an organic acid such as formic acid, acetic acid or citric acid, or a Lewis acid such as aluminum chloride may be used. On the other hand, when the protective groups are removed under reducing conditions, a catalytic reduction in the presence of a variety of catalysts, or a metallic reducing agent such as zinc or iron may be used. When $R^5$ is a silyl-type protective group such as t-butyldimethylsilyl, trimethylsilyl, or triethylsilyl, it can be easily removed with a fluorine ion reagent such as tetrabutylammonium fluoride. When $R^5$ is allyloxycarbonyl and $R^6$ is allyl, the protective groups can be easily removed with a variety of palladium complexes, for example, tetrakis(triphenylphosphine)palladium(0).

The compounds of formula (I) thus obtained can be isolated and purified, for example, by crystallization, chromatography with nonionic macro-high porous resin, gel filtration with Sephadex or the like, or reverse phase column chromatography on silica gel.

The compounds according to the present invention have potent antibiotic activity against a wide spectrum of Gram-positive and Gram-negative bacteria, and, in addition, exhibit potent antibiotic activity against MRSA, PRSP, Influenzavirus, and β-lactamase-producing bacteria. Further, they have no significant toxicity and are stable against DHP-1. Thus, the compounds according to the present invention can be used for the treatment of infectious diseases caused by various pathogenic bacteria in animals including humans. A pharmaceutical composition comprising as active ingredient the compound according to the present invention or a pharmacologically acceptable salt thereof can be administered orally or parenterally by administration routes, for example, intravenous injection, intramuscular injection, or subcutaneous, rectal, or percutaneous administration, to a human and a non-human animal.

The pharmaceutical composition comprising as active ingredient the compound according to the present invention can be formulated into appropriate dosage forms, primarily into any one of the preparation forms including: injections such as intravenous injection or intramuscular injection; preparations for oral administration such as capsules, tablets, granules, powders, pills, particulates, or troches; preparations for rectal administration; and fatty suppositories, depending on its administration routes.

These preparations can be prepared by the usual methods with pharmaceutically acceptable additives for preparations commonly used in the art, for example, excipients, fillers, binders, humidifiers, disintegrants, surface active agents, lubricants, dispersants, buffers, preservatives, dissolution aids, antiseptics, flavoring agents, analgesic agents, and stabilizers.

Such non-toxic additives usable herein include, for example, lactose, fructose, glucose, starch, gelatin, magnesium carbonate, synthetic magnesium silicate, talc, magnesium stearate, methylcellulose or a salt thereof, gum arabic, polyethylene glycol, syrup, petrolatum, glycerin, ethanol, propylene glycol, citric acid, sodium chloride, sodium sulfite, and sodium phosphate.

The dosage may be appropriately determined, for example, in consideration of the dosage route and the age, sex and condition of patients, and the preparation may be administered for the treatment of infectious diseases usually in an amount of about 25 mg to 2000 mg, preferably 50 mg to 1000 mg, per day per adult in one or several portions.

EXAMPLES

Synthesis Example 1

7-(2-t-Butyldimethyl-silyloxyethyl)thio-2-(tri-n-butylstannyl)imidazo[5,1-b]thiazole a) 7-(2-t-Butyldimethylsilyloxyethyl)thioimidazo-[5,1-b]thiazole A solution of 250 mg of 7-iodoimidazo[5,1-b]thiazole in 5 ml of dry THF was cooled in ice, and a 0.93 M methylmagnesium bromide/THF solution (1.08 ml) was added to the solution under an argon atmosphere. The mixture was stirred at that temperature for 25 min, and the solvent was then removed by distillation under the reduced pressure. The residue was suspended in 5 ml of THF, and 34 mg of sulfur was added to the suspension. The mixture was heated under reflux for 40 min. 2-t-Butyldimethylsilyloxy ethanol (246 mg) was dissolved in 5 ml of dichloromethane. 2,6-Lutidine (0.179 ml) and 0.247 ml of trifluoromethanesulfonic anhydride were added to the solution at −30° C. under an argon atmosphere. The mixture was stirred at that temperature for 40 min, and the reaction solution was then diluted with dichloromethane. The diluted solution was washed with a dilute aqueous hydrochloric acid solution. The organic layer was dried over anhydrous magnesium sulfate, and was then concentrated under the reduced pressure. The residue was dissolved in 3 ml of THF. The solution was then added at room temperature to the reaction solution with sulfur added thereto. The mixture was stirred for 2 hr. A saturated aqueous ammonium chloride solution was added to the reaction mixture, and the mixture was then extracted with ethyl acetate, followed by washing with a dilute aqueous sodium thiosulfate solution and saturated brine in that order. The organic layer was dried over anhydrous magnesium sulfate. The solvent was removed by distillation, and the residue was purified by column chromatography on silica gel (hexane:ethyl acetate=1:1) to prepare 146 mg of 7-(2-t-butyldimethylsilyloxyethyl)thioimidazo[5,1-b]thiazole.

NMR (CDCl$_3$) δ: 0.02 (6H, s), 0.85 (9H, s), 2.85–2.95 (2H, m), 3.75–3.85 (2H, m), 6.87 (1H, d, J=4.2 Hz), 7.39 (1H, d, J=4.2 Hz), 7.99 (1H, s)

b) 7-(2-t-Butyldimethylsilyloxyethyl)thio-2-(tri-n-butylstannyl)imidazo[5,1-b]thiazole Tri-n-butylstannyl chloride (1.79 ml) and 13.2 ml of a 1.0 N lithiumbis(trimethylsilyl)amide/THF solution were added to a solution of 1.734 g of 7-(2-t-butyldimethylsilyloxyethyl)thioimidazo[5,1-b]thiazole in 60 ml of THF at −40° C. under an argon atmosphere, and the mixture was stirred at that temperature for one hr. An aqueous ammonium chloride solution was added to the reaction solution. The mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=3:1) to prepare 2.784 g of the title compound.

NMR (CDCl$_3$) δ: 0.01 (6H, s), 0.84 (9H, s), 0.91 (9H, t, J=7.4 Hz), 1.1–1.2 (6H, m), 1.3–1.45 (6H, m), 1.5–1.65 (6H, m), 2.85–2.95 (2H, m), 3.75–3.85 (2H, m), 7.12 (1H, s), 7.91 (1H, s)

Synthesis Example 2

7-(2-Azidoethyl)thio-2-(tri-n-butylstannyl)imidazo [5,1-b]thiazole a) 7-(2-Hydroxyethyl)thioimidazo[5,1-b]thiazole A solution of 5.0 g of 7-iodoimidazo[5,1-b]thiazole in 100 ml of dry THF was cooled in ice, and 23.15 ml of a 0.95 M methylmagnesium bromide/THF solution was added dropwise to the cooled solution under an argon atmosphere. The mixture was stirred at that temperature for 30 min. The solvent was then removed by distillation under the reduced pressure. The residue was suspended in 100 ml of THF. Sulfur (672 mg) was added to the suspension, and the mixture was heated under reflux for 30 min. The reaction solution was cooled to room temperature, and 1.87 ml of 2-iodoethanol was added thereto. The mixture was stirred for 4 hr. A saturated aqueous ammonium chloride solution and a dilute aqueous sodium thiosulfate solution were added to the reaction mixture, followed by extraction with ethyl acetate once and with dichloromethane twice. The organic layer was dried over anhydrous magnesium sulfate. The solvent was removed by distillation, and the residue was purified by column chromatography on silica gel (dichloromethane: methanol=20:1) to prepare 2.96 g of 7-(2-hydroxyethyl)thioimidazo[5,1-b]thiazole.

NMR (CDCl$_3$) δ: 2.9–3.0 (2H, m), 3.8–3.9 (2H, m), 6.90 (1H, d, J=4.3 Hz), 7.41 (1H, d, J=4.3 Hz), 8.01 (1H, s)

b) 7-(2-Azidoethyl)thioimidazo[5,1-b]thiazole 7-(2-Hydroxyethyl)thioimidazo[5,1-b]thiazole (1.67 g) was suspended in a mixed solvent composed of 70 ml of dichloromethane and 7 ml of DMF. N,N-Diisopropylethylamine (1.89 ml) and 0.774 ml of methanesulfonyl chloride were added to the suspension at −20° C. under an argon atmosphere. The mixture was stirred at that temperature for one hr. The reaction solution was then diluted with dichloromethane, and the diluted solution was adjusted to pH 3.3 by the addition of a dilute hydrochloric acid solution. The organic layer was separated, and the aqueous layer was extracted with dichloromethane twice. The combined organic layer was washed with an aqueous sodium hydrogencarbonate solution, and was dried over anhydrous magnesium sulfate. DMF (25 ml) was added thereto, and dichloromethane was removed by distillation under the reduced pressure. Sodium azide (1.63 g) was added to the residue, and the mixture was stirred at 50° C. for 7 hr. Brine was added to the reaction solution, and the mixture was extracted with ethyl acetate three times. The organic layers were combined, and washed with brine three times. The residue was purified by column chromatography on silica gel (hexane:ethyl acetate=1:2 to ethyl acetate only) to prepare 1.496 g of 7-(2-azidoethyl)thioimidazo[5,1-b] thiazole.

NMR (CDCl$_3$) δ: 2.9–3.0 (2H, m), 3.4–3.5 (2H, m), 6.90 (1H, d, J=4.2 Hz), 7.42 (1H, d, J=4.2 Hz), 8.02 (1H, s)

c) 7-(2-Azidoethyl)thio-2-(tri-n-butylstannyl)imidazo[5,1-b]thiazole

Tri-n-butylstannyl chloride (3.53 ml) and 12.34 ml of a 1.0 N lithiumbis(trimethylsilyl)amide/THF solution were added to a solution of 2.32 g of 7-(2-azidoethyl)thioimidazo [5,1-b]thiazole in 75 ml of THF at −65° C. under an argon atmosphere. The temperature of the mixture was raised to −30° C. over a period of 2 hr, during which time a 1.0 N lithiumbis(trimethylsilyl)amide/THF solution (1.0 ml) was added to the mixture four times. An aqueous ammonium chloride solution was added to the reaction mixture, and the mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=2:1) to prepare 4.62 g of the title compound.

NMR (CDCl$_3$) δ: 0.92 (9H, t, J=7.2 Hz), 1.1–1.2 (6H, m), 1.3–1.4 (6H, m), 1.5–1.65 (6H, m), 2.9–3.0 (2H, m), 3.45–3.55 (2H, m), 7.16 (1H, s), 7.95 (1H, s)

Synthesis Example 3

7-(2-Azidoethyl)thio-5-methylthio-2-(tri-n-butylstannyl)imidazo[5,1-b]thiazole a) 2-Methanesulfonyloxyethyl disulfide N,N-Diisopropylethylamine (4.35 ml) and 1.70 ml of methanesulfonyl chloride were added to a suspension of 1.22 ml of 2-hydroxyethyl disulfide in 30 ml of dichloromethane at −40° C. under an argon atmosphere. The mixture was stirred at that temperature for 30 min. The reaction solution was then diluted with dichloromethane, and the diluted solution was washed with an dilute aqueous hydrochloric acid solution, an aqueous sodium hydrogencarbonate solution, and water in that order, and was dried over anhydrous magnesium sulfate. The solvent was removed by distillation under the reduced pressure to prepare 3.08 g of 2-methanesulfonyloxyethyl disulfide.

NMR (CDCl$_3$) δ: 3.0–3.1 (4H, m), 3.07 (6H, s), 4.4–4.5 (4H, m)

b) 2-Azidoethyl disulfide

Sodium azide (572 mg) was added to a solution of 910 mg of 2-methanesulfonyloxyethyl disulfide in 20 ml of DMF, and the mixture was stirred at 50° C. for 2.5 hr. Brine was added to the reaction solution, and the mixture was extracted with ethyl acetate twice. The organic layers were combined, washed with brine twice, and then dried over anhydrous magnesium sulfate. The solvent was removed by distillation under the reduced pressure, and the residue was purified by column chromatography on silica gel (hexane:ethyl acetate= 10:1) to prepare 509 mg of 2-azidoethyl disulfide.

NMR (CDCl$_3$) δ: 2.85–2.95 (4H, m), 3.55–3.65 (4H, m)

c) 2-Azidoethyl (2-azidoethane)thiolsulfonate

A solution of 509 mg of 2-azidoethyl disulfide in 30 ml of dichloromethane was cooled in ice, and 1.61 g of 3-chloroperbenzoic acid was added to the cooled solution. The mixture was stirred at that temperature for one hr. The reaction solution was diluted with dichloromethane. The diluted solution was washed with an aqueous sodium thiosulfate solution, an aqueous sodium hydrogencarbonate solution, and water in that order, and was dried over anhydrous magnesium sulfate. The solvent was removed by distillation, and the residue was purified by column chromatography on silica gel (hexane:ethyl acetate=2:1) to prepare 212 mg of 2-azidoethyl (2-azidoethane)thiolsulfonate.

NMR (CDCl$_3$) δ: 3.3–3.4 (2H, m), 3.6–3.75 (4H, m), 3.8–3.9 (2H, m)

d) 7-Iodo-5-methylthioimidazo[5,1-b]thiazole

A 0.95 M ethylmagnesium bromide/THF solution (21.2 ml) was added to a solution of 7.77 g of 5,7-diiodoimidazo [5,1-b]thiazole in 65 ml of dry THF at −40° C. under an argon atmosphere. The mixture was stirred at that temperature for 30 min, and 2.46 ml of methylmethanethiol sulfonate was added thereto. The mixture was stirred at room temperature for 1.5 hr. A saturated aqueous ammonium chloride solution was added to the reaction mixture, and the mixture was then extracted with ethyl acetate, followed by washing with a dilute aqueous sodium thiosulfate solution and saturated brine in that order. The organic layer was dried over anhydrous magnesium sulfate. The solvent was removed by distillation. The residue was dissolved in 60 ml of dichloromethane. Hexane (100 ml) was added to the solution, and the mixture was subjected to displacement concentration. The resultant solid was collected by filtration to prepare 3.96 g of 7-iodo-5-methylthioimidazo[5,1-b] thiazole.

NMR (CDCl$_3$) δ: 2.53 (3H, s), 6.90 (1H, d, J=4.1 Hz), 7.50 (1H, d, J=4.1 Hz)

e) 7-(2-Azidoethyl)thio-5-methylthioimidazo[5,1-b]thiazole

A solution of 395 mg of 7-iodo-5-methylthioimidazo[5, 1-b]thiazole in 7 ml of THF was cooled in ice. A 0.96 M ethylmagnesium bromide/THF solution (1.39 ml) was added to the solution under an argon atmosphere. The mixture was stirred at that temperature for 15 min. A solution of 355 mg of 2-azidoethyl (2-azidoethane) thiolsulfonate in 2 ml of THF was then added thereto, and the mixture was stirred at that temperature for 25 min. An aqueous ammonium chloride solution was added to the reaction solution, and the mixture was extracted with ethyl acetate twice, followed by washing with an aqueous sodium thiosulfate solution and brine in that order, and was dried over anhydrous magnesium sulfate. The solvent was removed by distillation, and the residue was purified by column chromatography on silica gel (hexane:ethyl acetate=5:1) to prepare 292 mg of 7-(2-azidoethyl)thio-5-methylthioimidazo[5,1-b]thiazole.

NMR (CDCl$_3$) δ: 2.58 (3H, s), 2.9–3.0 (2H, m), 3.4–3.55 (2H, m), 6.90 (1H, d, J=4.2 Hz), 7.40 (1H, d, J=4.2 Hz)

f) 7-(2-Azidoethyl)thio-5-methylthio-2-(tri-n-butylstannyl) imidazo[5,1-b]thiazole The procedure of Synthesis Example 2c) was repeated, except that 292 mg 7-(2-azidoethyl)thio-5-methylthioimidazo[5,1-b]thiazole was used as the starting compound. Thus, 485 mg of the title compound was prepared.

NMR (CDCl$_3$) δ: 0.92 (9H, t, J=7.4 Hz), 1.15–1.25 (6H, m), 1.3–1.45 (6H, m), 1.5–1.65 (6H, m), 2.56 (3H, s), 2.9–3.0 (2H, m), 3.45–3.55 (2H, m), 7.12 (1H, s)

Synthesis Example 4

7-(2-Formylaminoethyl)thio-2-(tri-n-butylstannyl) imidazo[5,1-b]thiazole a) 7-(2-Formylaminoethyl)thioimidazo[5,1-b]thiazole 7-(2-Azidoethyl)thioimidazo[5,1-b]thiazole (397 mg) was dissolved in a mixed solvent composed of 10 ml of THF and 10 ml of water. A 1 N aqueous hydrochloric acid solution (5.3 ml) and 200 mg of 10% Pd-C were added to the solution. The air in the reaction vessel was replaced by hydrogen, and the contents of the reaction vessel were stirred at room temperature for 6 hr. The catalyst was removed by filtration on Celite, and was then washed with water. The filtrate was concentrated under the reduced pressure until the volume was substantially halved. Dichloromethane (20 ml) was added, and the mixture was adjusted to pH 7.0 by the addition of an aqueous sodium hydrogencarbonate solution. Formic acid (0.90 ml) and 0.50 ml of acetic anhydride, which had been stirred at 50° C. for 5 min, were added thereto under ice cooling. The mixture was stirred at that temperature for 20 min while maintaining the pH value at about 7.0. The reaction solution was adjusted to pH 8.3 by the addition of an aqueous sodium hydrogencarbonate solution, and was then extracted with dichloromethane three times. The organic layer was dried over anhydrous magnesium sulfate. The solvent was then removed by distillation, and the residue was purified by column chromatography on silica gel (dichloromethane:methanol=20:1) to prepare 250 mg of 7-(2-formylaminoethyl)thioimidazo[5,1-b]thiazole.

NMR (CDCl$_3$) δ: 2.85–2.95 (2H, m), 3.5–3.6 (2H, m), 6.92 (1H, d, J=4.3 Hz), 7.2–7.4 (1H, m), 7.43 (1H, d, J=4.3 Hz), 8.02 (1H, s), 8.22 (1H, s)

b) 7-(2-Formylaminoethyl)thio-2-(tri-n-butylstannyl) imidazo[5,1-b]thiazole

A 1.6 N n-butyllithium/n-hexane solution (11.7 ml) was added to a solution of 1.19 g of 7-(2-formylaminoethyl) thioimidazo[5,1-b]thiazole in 50 ml of THF at −55° C. under an argon atmosphere. The mixture was stirred at that temperature for 10 min. Tri-n-butylstannyl chloride (2.24 ml) was added thereto, and the mixture was stirred for 20 min. The temperature of the reaction solution was raised to −30° C. over a period of one hr, during which time 3.34 ml of a 1.6 N n-butyllithium/n-hexane solution and 2.4 ml of tri-n-butylstannyl chloride were added. An aqueous ammonium chloride solution was added to the reaction solution, and the mixture was extracted with ethyl acetate, followed by washing with brine. The organic layer was dried over anhydrous magnesium sulfate. The solvent was removed by distillation, and the residue was purified by column chromatography on silica gel (ethyl acetate only to dichloromethane:methanol= 20:1) to prepare 1.615 g of the title compound.

NMR (CDCl$_3$) δ: 0.92 (9H, t, J=7.3 Hz), 1.1–1.2 (6H, m), 1.3–1.45 (6H, m), 1.5–1.65 (6H, m), 2.75–2.85 (2H, m), 3.5–3.6 (2H, m), 7.16 (1H, s), 7.6–7.7 (1H, m), 7.94 (1H, s), 8.21 (1H, s)

Synthesis Example 5

7-[3-(4-Nitrobenzyloxycarbonyl)aminopropyl]thio-2-(tri-n-butylstannyl)imidazo[5,1-b]thiazole a) 7-[3-(4-Nitrobenzyloxycarbonyl)aminopropyl] thioimidazo[5,1-b]thiazole The procedure of Synthesis Example 2a) was repeated, except that 1.25 g of 7-iodoimidazo[5,1-b]thiazole and 1.82 g 1-iodo-3-(4-nitrobenzyloxycarbonyl)aminopropane were used as the starting compounds. Thus, 810 mg of 7-[3-(4-nitrobenzyloxycarbonyl)aminopropyl]thioimidazo-[5,1-b]thiazole was prepared.

NMR (CDCl$_3$) δ: 1.75–1.9 (2H, m), 2.8–2.9 (2H, m), 3.3–3.45 (2H, m), 5.18 (2H, s), 5.50 (1H, br s), 6.88 (1H, d, J=4.3 Hz), 7.41 (1H, d, J=4.3 Hz), 7.50 (2H, d, J=8.6 Hz), 8.01 (1H, s), 8.20 (2H, d, J=8.6 Hz)

b) 7-[3-(4-Nitrobenzyloxycarbonyl)aminopropyl]thio-2-(tri-n-butylstannyl)imidazo[5,1-b]thiazole Tri-n-butylstannyl chloride (1.21 ml) and 9.47 ml of a 1.0 N lithiumbis(trimethylsilyl)amide/THF solution were added to a solution of 1.11 g of 7-[3-(4-nitrobenzyloxycarbonyl)aminopropyl]thioimidazo[5,1-b]thiazole in 28 ml of THF at −45° C. under an argon atmosphere, and the mixture was stirred for one hr. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=1:1) to prepare 1.24 g of the title compound.

NMR (CDCl$_3$) δ: 0.91 (9H, t, J=7.3 Hz), 1.1–1.2 (6H, m), 1.3–1.4 (6H, m), 1.5–1.6 (6H, m), 1.8–1.9 (2H, m), 2.8–2.9 (2H, m), 3.35–3.45 (2H, m), 5.18 (2H, s), 5.58 (1H, br s), 7.15 (1H, s), 7.50 (2H, d, J=8.7 Hz), 7.94 (1H, s), 8.20 (2H, d, J=8.7 Hz)

Synthesis Example 6

7-[2-N,N'-Bis(4-nitrobenzyloxycarbonyl)guanidinoethyl]thio-2-(tri-n-butylstannyl)imidazo[5,1-b]thiazole a) 1H-Pyrazole-1-[N-(4-nitrobenzyloxycarbonyl)]-carboxamidine 1H-Pyrazole-1-carboxamidine hydrochloride (1.46 g) was suspended in 20 ml of dichloromethane. N,N-Diisopropylethylamine (4.52 ml) and 2.59 g of 4-nitrobenzyl chloroformate were added to the suspension. The mixture was stirred at room temperature for 30 min. The precipitated crystal was collected by filtration, and was washed with dichloromethane to prepare 2.373 g of 1H-pyrazole-1-[N-(4-nitrobenzyloxycarbonyl)]carboxamidine.

NMR (CDCl$_3$) δ: 5.30 (2H, s), 6.4–6.5 (1H, m), 7.60 (2H, d, J=8.7 Hz), 7.65–7.75 (1H, m), 8.23 (2H, d, J=8.7 Hz), 8.4–8.5 (1H, m), 9.02 (1H, br s)

b) 1H-Pyrazole-1-[N,N'-bis(4-nitrobenzyloxycarbonyl)]carboxamidine

A solution of 1.51 g of 1H-pyrazole-1-[N-(4-nitrobenzyloxycarbonyl)]carboxamidine in 70 ml of THF was cooled in ice, and 731 mg of sodium hydride was added to the cooled solution under an argon atmosphere. The mixture was stirred for 20 min. 4-Nitrobenzyl chloroformate (1.69 g) was added thereto, and the mixture was stirred at that temperature for 2 hr. An aqueous ammonium chloride solution was added to the reaction solution, and the mixture was extracted with ethyl acetate twice. The organic layer was washed with brine twice, and was dried over anhydrous magnesium sulfate. The solvent was removed by distillation, and the residue was purified by column chromatography on silica gel (hexane:ethyl acetate=1:2) to prepare 1.821 g of 1H-pyrazole-1-[N,N'-bis(4-nitrobenzyloxycarbonyl)]carboxamidine.

NMR (CDCl$_3$) δ: 5.30 (2H, s), 5.32 (2H, s), 6.5–6.55 (1H, m), 7.53 (2H, d, J=8.7 Hz), 7.60 (2H, d, J=8.7 Hz), 7.68–7.72 (1H, m), 8.2–8.3 (4H, m), 8.3–8.35 (1H, m), 9.46 (1H, br s)

c) 7-[2-N,N'-Bis(4-nitrobenzyloxycarbonyl)guanidinoethyl]thioimidazo[5,1-b]thiazole 7-(2-Azidoethyl)thioimidazo[5,1-b]thiazole (2.18 g) was dissolved in a mixed solvent composed of 48 ml of ethanol and 10 ml of water. A 1 N aqueous hydrochloric acid solution (9.69 ml) and 2.18 g of 10% Pd-C were added to the solution. The air in the reaction vessel was replaced by hydrogen, and the contents of the reaction vessel were stirred at room temperature for 16 hr. The catalyst was removed by filtration on Celite, and was then washed with water. The filtrate was concentrated to dryness, and the residue was dissolved in 80 ml of DMF. N,N-Diisopropylethylamine (1.68 ml) and 4.53 g of 1H-pyrazole-1-[N,N'-bis(4-nitrobenzyloxycarbonyl)]carboxamidine were added to the solution, and the mixture was stirred at room temperature for 18 hr. Brine was added to the reaction solution, and the mixture was extracted with ethyl acetate twice. The organic layer was washed with brine three times, and was then dried over anhydrous magnesium sulfate. The solvent was removed by distillation. Dichloromethane (20 ml) and 10 ml of ethyl acetate were added to the residue. The insolubles were collected by filtration to prepare 2.80 g of 7-[2-N,N'-bi(4-nitrobenzyloxycarbonyl)guanidinoethyl]thioimidazo-[5,1-b]thiazole.

NMR (CDCl$_3$) δ: 2.95–3.05 (2H, m), 3.6–3.7 (2H, m), 5.21 (2H, s), 5.31 (2H, s), 6.87 (1H, d, J=4.2 Hz), 7.40 (1H, d, J=4.2 Hz), 7.54 (2H, d, J=8.7 Hz), 7.55 (2H, d, J=8.7 Hz), 8.0 (1H, s), 8.20 (2H, d, J=8.7 Hz), 8.25 (2H, d, J=8.7 Hz), 8.88 (1H, br s)

d) 7-[2-N,N'-Bis(4-nitrobenzyloxycarbonyl)guanidinoethyl]thio-2-(tri-n-butylstannyl)imidazo[5,1-b]thiazole The procedure of Synthesis Example 5b) was repeated, except that 78.3 mg of 7-[2-N,N'-bis(4-nitrobenzyloxycarbonyl)guanidinoethyl]thioimidazo[5,1-b]thiazole was used as the starting compound. Thus, 47.9 mg of the title compound was prepared.

NMR (CDCl$_3$) δ: 0.92 (9H, t, J=7.2 Hz), 1.1–1.2 (6H, m), 1.3–1.4 (6H, m), 1.5–1.6 (6H, m), 2.9–3.0 (2H, m), 3.6–3.7 (2H, m), 5.21 (2H, s), 5.31 (2H, s), 7.14 (1H, s), 7.5–7.6 (4H, m), 7.93 (1H, s), 8.15–8.3 (4H, m), 8.9–9.0 (1H, m), 11.79 (1H, br s)

Synthesis Example 7

7-(6-Azidohexyl)thio-2-(tri-n-butylstannyl)imidazo[5,1-b]thiazole a) 7-(6-Azidohexyl)thioimidazo[5,1-b]thiazole The procedure of Synthesis Example 1a) was repeated, except that 1.00 g of 7-iodoimidazo[5,1-b]thiazole and 686 mg of 6-azido-1-hexanol were used as the starting compounds. Thus, 636 mg of 7-(6-azidohexyl)thioimidazo[5,1-b]thiazole was prepared.

NMR (CDCl$_3$) δ: 1.3–1.5 (4H, m), 1.5–1.7 (4H, m), 2.75–2.85 (2H, m), 3.2–3.3 (2H, m), 6.87 (1H, d, J=4.2 Hz), 7.39 (1H, d, J=4.2 Hz), 8.00 (1H, s)

b) 7-(6-Azidohexyl)thio-2-(tri-n-butylstannyl)imidazo[5,1-b]thiazole

Tri-n-butylstannyl chloride (0.969 ml) and 5.66 ml of a 1.0 N lithiumbis(trimethylsilyl)amide/THF solution were added to a solution of 636 mg of 7-(6-azidohexyl)thioimidazo[5,1-b]thiazole in 20 ml of THF at −40° C. under an argon atmosphere. The mixture was stirred for 45 min. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=2:1) to prepare 1.01 g of the title compound.

NMR (CDCl$_3$) δ: 0.92 (9H, t, J=7.2 Hz), 1.1–1.2 (6H, m), 1.3–1.45 (6H, m), 1.5–1.65 (6H, m), 2.75–2.85 (2H, m), 3.2–3.3 (2H, m), 7.13 (1H, s), 7.93 (1H, s)

Synthesis Example 8

7-[(3S)-1-(4-Nitrobenzyloxycarbonyl)pyrrolidin-3-yl]thio-2-(tri-n-butylstannyl)imidazo[5,1-b]thiazole a) 7-[(3S)-1-(4-Nitrobenzyloxycarbonyl)pyrrolidin-3-yl]thioimidazo[5,1-b]thiazole The procedure of Synthesis Example 1a) was repeated, except that 1.00 g of 7-iodoimidazo[5,1-b]thiazole and 1.49 g of (3R)-3-hydroxy-1-(4-nitrobenzyloxycarbonyl)pyrrolidine were used as the starting compounds. Thus, 814 mg of 7-[(3S)-1-(4-nitrobenzyloxycarbonyl)pyrrolidin-3-yl]thioimidazo[5,1-b]thiazole was prepared.

NMR (DMSO-d$_6$) δ: 1.8–2.0 (1H, m), 2.1–2.3 (1H, m), 3.25–3.7 (5H, m), 5.20 (2H, s), 7.29, 7.31 (total 1H, s each), 7.58–7.66 (2H, m), 7.91, 7.92 (total 1H, s each), 8.20–8.30 (3H, m)

b) 7-[(3S)-1-(4-Nitrobenzyloxycarbonyl)pyrrolidin-3-yl]thio-2-(tri-n-butylstannyl)imidazo[5,1-b]thiazole The procedure of Synthesis Example 2c) was repeated, except that 450 mg of 7-[(3S)-1-(4-nitrobenzyloxycarbonyl)pyrrolidin-3-yl]thioimidazo[5,1-b]thiazole was used as the starting compound. Thus, 203 mg of the title compound was prepared.

NMR (CDCl$_3$) δ: 0.8–1.0 (9H, m), 1.0–1.2 (6H, m), 1.3–1.5 (6H, m), 1.5–1.7 (6H, m), 1.9–2.3 (2H, m), 3.4–3.8 (5H, m), 5.22 (2H, s), 7.15, 7.16 (total 1H, s each), 7.45–7.55 (2H, m), 7.95, 7.96 (total 1H, s each), 8.15–8.25 (2H, m)

Synthesis Example 9

7-Carbamoylmethylthio-2-(tri-n-butylstannyl)imidazo[5,1-b]thiazole

In the same manner as in Synthesis Example 2a), a reaction was carried out using 1.00 g of 7-iodoimidazo[5,1-b]thiazole and 888 mg of iodoacetamide as the starting compounds, and the extract was concentrated to dryness to prepare 1.02 g of 7-carbamoyl methylthioimidazo[5,1-b]thiazole as a crude product. Thereafter, 112 mg of the crude product was suspended in a mixed solvent composed of 8 ml of THF and 2 ml of HMPA. A 1.6 N n-butyllithium/n-hexane solution (1.21 ml) and 0.224 ml of tri-n-butylstannyl chloride were added dropwise to the suspension at –45° C. under an argon atmosphere. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (dichloromethane:ethyl acetate=1:2 to ethyl acetate only) to prepare 56.5 mg of the title compound.

NMR (CDCl$_3$) δ: 0.92 (9H, t, J=7.2 Hz), 1.1–1.2 (6H, m), 1.3–1.4 (6H, m), 1.5–1.7 (6H, m), 3.42 (2H, s), 5.55 (1H, br s), 7.16 (1H, s), 7.93 (1H, s), 8.00 (1H, br s)

Synthesis Example 10

7-[2-(4-Nitrobenzyloxycarbonyl)aminosulfonylaminoethyl]thio-2-(tri-n-butylstannyl)imidazo[5,1-b]thiazole a) 7-[2-(4-Nitrobenzyloxycarbonyl)aminosulfonylaminoethyl]thioimidazo[5,1-b]thiazole 7-(2-Azidoethyl)thioimidazo[5,1-b]thiazole (2.55 g) was dissolved in a mixed solvent composed of 55 ml of THF and 55 ml of water. A 1 N aqueous hydrochloric acid solution (30.0 ml) and 2.55 g of 10% Pd-C were added to the solution. The air in the reaction vessel was replaced by hydrogen, and the contents of the reaction vessel were stirred at room temperature for 24 hr. The catalyst was removed by filtration on Celite, and was then washed with water. The filtrate was concentrated to dryness, and 30 ml of a 1 N aqueous sodium hydroxide solution was added, followed by extraction with dichloromethane five times. The organic layer was dried over anhydrous magnesium sulfate. The solvent was then removed by distillation. The residue was dissolved in 14 ml of dichloromethane. A solution of 1.22 ml of triethylamine and 2.05 g of (4-nitrobenzyloxycarbonyl)aminosulfonyl chloride in 10 ml of dichloromethane was added to the solution at –20° C. under an argon atmosphere. The mixture was stirred at that temperature for one hr. The reaction solution was diluted with dichloromethane, and the diluted solution was washed with an aqueous sodium hydrogencarbonate solution. The organic layer was dried over anhydrous magnesium sulfate. The solvent was then removed by distillation, and the residue was purified by column chromatography on silica gel (dichloromethane:methanol=30:1) to prepare 805 mg of 7-[2-(4-nitrobenzyloxycarbonyl)aminosulfonylaminoethyl]thioimidazo[5,1-b]thiazole.

NMR (CD$_3$OD) δ: 2.8–2.85 (2H, m), 3.15–3.25 (2H, m), 5.29 (2H, s), 7.16 (1H, d, J=4.2 Hz), 7.61 (2H, d, J=8.7 Hz), 7.74 (1H, d, J=4.2 Hz)

b) 7-[2-(4-Nitrobenzyloxycarbonyl)aminosulfonylaminoethyl]thio-2-(tri-n-butylstannyl)imidazo[5,1-b]-thiazole The procedure of Synthesis Example 1b) was repeated, except that 39.7 mg of 7-[2-(4-nitrobenzyloxycarbonyl)aminosulfonylaminoethyl]thioimidazo[5,1-b]thiazole was used as the starting compound. Thus, 18.4 mg of the title compound was prepared.

NMR (CDCl$_3$) δ: 0.92 (9H, t, J=7.2 Hz), 1.15–1.25 (6H, m), 1.3–1.4 (6H, m), 1.5–1.65 (6H, m), 2.8–2.9 (2H, m), 3.4–3.5 (2H, m), 5.32 (2H, s), 7.15 (1H, s), 7.53 (2H, d, J=9.0 Hz), 7.95 (1H, s), 8.17 (2H, d, J=9.0 Hz)

Synthesis Example 11

7-[1-(4-Nitrobenzyloxycarbonyl)piperidin-4-yl]thio-2-(tri-n-butylstannyl)imidazo[5,1-b]thiazole a) 7-Acetylthioimidazo[5,1-b]thiazole The procedure of Example 2a) was repeated, except that 5.0 g of 7-iodoimidazo[5,1-b]thiazole and 1.71 ml of acetyl chloride were used as the starting compounds. Thus, 2.02 g of 7-acetylthioimidazo[5,1-b]thiazole was prepared.

NMR (CDCl$_3$) δ: 2.41 (3H, s), 6.92 (1H, d, J=4.2 Hz), 7.46 (1H, d, J=4.2 Hz), 8.08 (1H, s)

b) 7-[1-(4-Nitrobenzyloxycarbonyl)piperidin-4-yl]-thioimidazo[5,1-b]thiazole

4-Hydroxy-1-(4-nitrobenzyloxycarbonyl)piperidine (336 mg) was dissolved in 5 ml of dichloromethane. 2,6-Lutidine (0.154 ml) and 0.212 ml of trifluoromethanesulfonic anhydride were added to the solution at –50° C. under an argon atmosphere. The mixture was stirred at that temperature for 25 min. The reaction solution was then diluted with dichloromethane, and the diluted solution was washed with a dilute aqueous hydrochloric acid solution. The organic layer was dried over anhydrous magnesium sulfate, and was then concentrated under the reduced pressure to a volume of about 2 ml. A solution of 198 mg of 7-acetylthioimidazo[5,1-b]thiazole in 1 ml of methanol was cooled in ice, and 1.08 ml of a 1.018 M sodium methoxide/methanol solution was added to the cooled solution. The mixture was stirred for 10 min. The above extract was added to this mixture, and the mixture was stirred at room temperature for 2.5 hr. A saturated aqueous ammonium chloride solution was added to the reaction mixture, followed by extraction with ethyl acetate twice. The organic layer was washed with saturated brine, and was then dried over anhydrous magnesium sulfate. The solvent was removed by distillation, and the residue was purified by column chromatography on silica gel (dichloromethane:ethyl acetate=1:1 to ethyl acetate only) to prepare 276 mg of 7-[1-(4-nitrobenzyloxycarbonyl) piperidin-4-yl]thioimidazo[5,1-b]thiazole.

NMR (CDCl$_3$) δ: 1.5–2.05 (4H, m), 2.9–3.2 (3H, m), 4.0–4.2 (2H, m), 5.20 (2H, s), 6.90 (1H, d, J=3.9 Hz), 7.43 (1H, d, J=3.9 Hz), 7.48 (2H, d, J=8.7 Hz), 8.05 (1H, s), 8.21 (2H, d, J=8.7 Hz)

c) 7-[1-(4-Nitrobenzyloxycarbonyl)piperidin-4-yl]thio-2-(tri-n-butylstannyl)imidazo[5,1-b]thiazole The procedure of Synthesis Example 2c) was repeated, except that 276 mg of 7-[1-(4-nitrobenzyloxycarbonyl) piperidin-4-yl]thioimidazo[5,1-b]thiazole was used as the starting compound. Thus, 55.8 mg of the title compound was prepared.

NMR (CDCl$_3$) δ: 0.93 (9H, t, J=7.5 Hz), 1.1–1.2 (6H, m), 1.3–1.4 (6H, m), 1.4–1.75 (8H, m), 1.9–2.05 (2H, m), 2.9–3.2 (3H, m), 4.0–4.2 (2H, m), 5.20 (2H, s), 7.16 (1H, s), 7.49 (2H, d, J=8.7 Hz), 7.97 (1H, s), 8.21 (2H, d, J=8.7 Hz)

Synthesis Example 12

7-(2-N,N-Dimethylaminosulfonylaminoethyl)thio-2-(tri-n-butylstannyl)imidazo[5,1-b]thiazole a) 7-(2-N,N-Dimethylaminosulfonylaminoethyl) thioimidazo[5,1-b]thiazole 7-(2-Azidoethyl)thioimidazo[5,1-b]thiazole (675 mg) was dissolved in a mixed solvent composed of 13 ml of ethanol and 3 ml of water. A 1 N aqueous hydrochloric acid solution (3.0 ml) and 675 mg of 10% Pd-C were added to the solution. The air in the reaction vessel was replaced by hydrogen, and the contents of the reaction vessel were stirred at room temperature for 24 hr. The catalyst was removed by filtration on Celite, and was washed with water. The filtrate was concentrated to dryness. A 1 N aqueous sodium hydroxide solution (20 ml) was added thereto, and the mixture was extracted with dichloromethane five times. The organic layer was dried over anhydrous magnesium sulfate. The solvent was then removed by distillation, and the residue was dissolved in 6 ml of dichloromethane. Triethylamine (0.333 ml) and 0.205 ml of dimethylsulfamoyl chloride were added to the solution at −20° C. under an argon atmosphere. The mixture was stirred at that temperature for one hr. Triethylamine (0.666 ml in total) and dimethylsulfamoyl chloride (0.342 ml in total) were added thereto with stirring over a period of 20 hr, during which time the temperature was raise to room temperature. An aqueous sodium hydrogencarbonate solution was added to the reaction solution, and the mixture was extracted with dichloromethane three times. The organic layer was dried over anhydrous magnesium sulfate. The solvent was then removed by distillation, and the residue was purified by column chromatography on silica gel (dichloromethane:methanol=30:1) to prepare 366 mg of 7-(2-N,N-dimethylaminosulfonylaminoethyl)thioimidazo [5,1-b]thiazole.

NMR (CDCl$_3$) δ: 2.81 (6H, s), 2.85–2.95 (2H, m), 3.3–3.4 (2H, m), 6.25–6.35 (1H, m), 6.91 (1H, d, J=4.2 Hz), 7.21 (1H, d, J=4.2 Hz), 8.03 (1H, s)

b) 7-(2-N,N-Dimethylaminosulfonylaminoethyl)thio-2-(tri-n-butylstannyl)imidazo[5,1-b]thiazole Tri-n-butylstannyl chloride (0.369 ml) and 2.48 ml of a 1.0 N lithiumbis(trimethylsilyl)amide/THF solution were added to a solution of 303 mg of 7-(2-N,N-dimethylaminosulfonylaminoethyl)thioimidazo[5,1-b] thiazole in 8 ml of THF at −50° C. under an argon atmosphere. The mixture was stirred at that temperature for 30 min. An aqueous ammonium chloride solution was added to the reaction solution, and the mixture was extracted with ethyl acetate, followed by washing with brine. The organic layer was dried over anhydrous magnesium sulfate. The solvent was then removed by distillation, and the residue was purified by column chromatography on silica gel (hexane:ethyl acetate=1:2) to prepare 2.784 g of the title compound.

NMR (CDCl$_3$) δ: 0.92 (9H, t, J=7.2 Hz), 1.1–1.2 (6H, m), 1.3–1.4 (6H, m), 1.5–1.65 (6H, m), 2.81 (6H, s), 2.85–2.95 (2H, m), 3.3–3.4 (2H, m), 6.4–6.5 (1H, m), 7.15 (1H, s), 7.96 (1H, s)

Synthesis Example 13

7-(2-Bromoethyl)thio-2-(tri-n-butylstannyl)imidazo [5,1-b]thiazole a) 7-(2-Bromoethyl)thioimidazo[5,1-b]thiazole The procedure of Synthesis Example 11b) was repeated, except that 990 mg of 7-acetylthioimidazo[5,1-b]thiazole and 0.461 ml of 2-bromo ethanol were used as the starting compounds. Thus, 1.06 g of 7-(2-bromoethyl)thioimidazo [5,1-b]thiazole was prepared.

NMR (CDCl$_3$) δ: 3.1–3.2 (2H, m), 3.5–3.6 (2H, m), 6.90 (1H, d, J=3.9 Hz), 7.42 (1H, d, J=3.9 Hz), 8.01 (1H, s)

b) 7-(2-Bromoethyl)thio-2-(tri-n-butylstannyl)imidazo[5,1-b]thiazole

The procedure of Synthesis Example 2c) was repeated, except that 1.06 g of 7-(2-bromoethyl)thioimidazo[5,1-b] thiazole was used as the starting compound. Thus, 1.62 g of the title compound was prepared.

NMR (CDCl$_3$) δ: 0.92 (9H, t, J=7.2 Hz), 1.1–1.2 (6H, m), 1.3–1.4 (6H, m), 1.5–1.65 (6H, m), 3.1–3.2 (2H, m), 3.5–3.6 (2H, m), 7.15 (1H, s), 7.94 (1H, s)

Synthesis Example 14

5,7-Bis(methylthio)-2-(tri-n-butylstannyl)imidazo[5, 1-b]thiazole a) 5,7-Bis(methylthio)imidazo[5,1-b]thiazole A 0.95 M ethylmagnesium bromide/THF solution (35.5 ml) was added to a solution of 5.50 g of 5,7-diiodoimidazo [5,1-b]thiazole in 45 ml of dry THF at −40° C. under an argon atmosphere. The mixture was stirred at that temperature for 2.5 hr. Methyl methanethiolsulfonate (3.88 ml) was added thereto, and the mixture was stirred at room temperature for 1.5 hr. A saturated aqueous ammonium chloride solution was added to the reaction mixture, and the mixture was then extracted with ethyl acetate, followed by washing with a dilute aqueous sodium thiosulfate solution and saturated brine in that order. The organic layer was dried over anhydrous magnesium sulfate. The solvent was removed by distillation, and the residue was purified by column chromatography on silica gel (hexane:ethyl acetate=1:1) to prepare 1.40 g of 5,7-bis(methylthio)imidazo[5,1-b]thiazole.

NMR (CDCl$_3$) δ: 2.43 (3H, s), 2.55 (3H, s), 6.86 (1H, d, J=4.1 Hz), 7.38 (1H, d, J=4.1 Hz)

b) 5,7-Bis(methylthio)-2-(tri-n-butylstannyl)imidazo[5,1-b] thiazole 5,7-Bis(methylthio)imidazo[5,1-b]thiazole (1.66 g) was dissolved in 50 ml of THF under an argon atmosphere. The solution was cooled to −60° C. A 1.6 N n-butyllithium/n- hexane solution (5.76 ml) and 2.29 ml of tri-n-butylstannyl chloride were added dropwise in that order to the solution, and the temperature of the mixture was raised to −40° C. over a period of one hr. Ethyl acetate (100 ml) was added to the reaction solution, and the mixture was washed with 100 ml of brine. The organic layer was dried over anhydrous magnesium sulfate, and was filtered. The solvent was removed by distillation under the reduced pressure. The residue was purified by column chromatography on silica gel (hexane:ethyl acetate=4:1) to prepare 2.31 g of the title compound.

NMR (CDCl$_3$) δ: 0.92 (9H, t, J=7.3 Hz), 1.15–1.20 (6H, m), 1.30–1.41 (6H, m), 1.56–1.62 (6H, m), 2.42 (3H, s), 2.54 (3H, s), 7.12 (1H, s)

Synthesis Example 15

2-(Tri-n-butylstannyl)-7-trifluoromethylthioimidazo [5,1-b]thiazole a) 7-Trifluoromethylthioimidazo[5,1-b]thiazole The procedure of Synthesis Example 2a) was repeated, except that 2.91 g of 7-iodoimidazo[5,1-b]thiazole and 4.91 g of S-(trifluoromethyl)dibenzothiophenium trifluoromethanesulfonate were used as the starting compounds. Thus, 590 mg of 7-trifluoromethylthioimidazo[5,1-b] thiazole was prepared.

NMR (CDCl$_3$) δ: 6.99 (1H, d, J=4.4 Hz), 7.49 (1H, d, J=4.4 Hz), 8.09 (1H, s)

b) 2-(Tri-n-butylstannyl)-7-trifluoromethylthioimidazo[5,1-b]thiazole

7-Trifluoromethylthioimidazo[5,1-b]thiazole (590 mg) was dissolved in 10 ml of THF under an argon atmosphere, and the solution was cooled to −65° C. Tri-n-butylstannyl chloride (2.07 ml) and 7.2 ml of a 1.0 N lithiumbis (trimethylsilyl)amide/THF solution were added dropwise in that order to the cooled solution. The temperature of the mixture was raised to −40° C. over a period of 30 min. Ethyl acetate (40 ml) was added to the reaction solution, and the mixture was washed with 40 ml of brine. The organic layer was dried over anhydrous magnesium sulfate, and was then filtered. The solvent was removed by distillation under the reduced pressure. The residue was purified by column chromatography on silica gel (hexane:ethyl acetate=4:1) to prepare 951 mg of the title compound.

NMR (CDCl$_3$) δ: 0.92 (9H, t, J=7.3 Hz), 1.16–1.20 (6H, m), 1.30–1.41 (6H, m), 1.54–1.62 (6H, m), 7.21 (1H, s), 8.01 (1H, s)

Synthesis Example 16

7-(2-Fluoroethyl)thio-2-(tri-n-butylstannyl)imidazo [5,1-b]thiazole a) 7-(2-Fluoroethyl)thioimidazo[5,1-b]thiazole The procedure of Synthesis Example 1a) was repeated, except that 400 mg of 7-iodoimidazo[5,1-b]thiazole and 218 mg of 2-fluoroethanol were used as the starting compounds. Thus, 204 mg of 7-(2-fluoroethyl)thioimidazo[5,1-b] thiazole was prepared.

NMR (CDCl$_3$) δ: 3.02–3.12 (2H, m), 4.45–4.67 (2H, m), 6.89 (1H, d, J=4.2 Hz), 7.41 (1H, d, J=4.2 Hz), 8.01 (1H, s)

b) 7-(2-Fluoroethyl)thio-2-(tri-n-butylstannyl)imidazo[5,1-b]thiazole

The procedure of Synthesis Example 15b) was repeated, except that 202 mg of 7-(2-fluoroethyl)thioimidazo[5,1-b] thiazole was used as the starting compound. Thus, 951 mg of the title compound was prepared.

NMR (CDCl$_3$) δ: 0.92 (9H, t, J=7.3 Hz), 1.14–1.19 (6H, m), 1.31–1.41 (6H, m), 1.54–1.62 (6H, m), 3.01–3.09 (2H, m), 4.50 (1H, t, J=7.1 Hz), 4.62 (1H, t, J=7.1 Hz), 7.14 (1H, s), 7.94 (1H, s)

Synthesis Example 17

7-[3-N,N'-Bis(4-nitrobenzyloxycarbonyl) guanidinopropyl]thio-2-(tri-n-butylstannyl)imidazo [5,1-b]thiazole a) 7-(3-Azidopropyl)thioimidazo[5,1-b]thiazole The procedure of Synthesis Example 1a) was repeated, except that 12.5 g of 7-iodoimidazo[5,1-b]thiazole and 6.06 g of 3-azidopropanol were used as the starting compounds. Thus, 8.56 g of 7-(3-azidopropyl)thioimidazo[5,1-b]thiazole was prepared.

NMR (CDCl$_3$) δ: 1.8–1.9 (2H, m), 2.8–2.9 (2H, m), 3.4–3.5 (2H, m), 6.88 (1H, d, J=4.5 Hz), 7.41 (1H, d, J=4.5 Hz), 8.01 (1H, s)

b) 7-(3-Aminopropyl)thioimidazo[5,1-b]thiazole 7-(3-Azidopropyl)thioimidazo[5,1-b]thiazole (1.46 g) was dissolved in 30 ml of THF ethanol and 6 ml of water, and 6.1 ml of a 1 N aqueous hydrochloric acid solution and 1.46 g of 10% Pd-C were added to the solution. The air in the reaction vessel was replaced by hydrogen, and the contents of the reaction vessel were stirred at room temperature for 24 hr. The catalyst was removed by filtration on Celite, and was washed with water. The filtrate was concentrated under the reduced pressure. A 1 N aqueous sodium hydroxide solution (20 ml) was added to the residue, and the mixture was extracted with dichloromethane five times. The extract was dried over anhydrous magnesium sulfate. The solvent was removed by distillation to prepare 1.15 g of 7-(3-aminopropyl)thioimidazo[5,1-b]thiazole.

NMR (CDCl$_3$) δ: 1.7–1.8 (2H, m), 2.8–2.9 (4H, m), 6.88 (1H, d, J=4.2 Hz), 7.40 (1H, d, J=4.2 Hz), 8.01 (1H, s)

c) 7-[3-N,N'-Bis(4-nitrobenzyloxycarbonyl) guanidinopropyl]thioimidazo[5,1-b]thiazole 7-(3-Aminopropyl)thioimidazo[5,1-b]thiazole (629 mg) was dissolved in 12 ml of DMF, and 1.66 g of 1H-pyrazole-1-[N,N'-bis(4-nitrobenzyloxycarbonyl)]carboxamidine was added to the solution. The mixture was stirred at room temperature for 19 hr. Brine was added to the reaction solution, and the mixture was extracted with ethyl acetate twice. The organic layer was washed with brine three times. The extract was dried over anhydrous magnesium sulfate. The solvent was removed by distillation, and the residue was purified by column chromatography on silica gel (dichloromethane:ethyl acetate=1:1) to prepare 1.12 g of 7-[3-N,N'-bis(4-nitrobenzyloxycarbonyl)guanidinopropyl] thioimidazo[5,1-b]thiazole.

NMR (CDCl$_3$) δ: 1.85–1.95 (2H, m), 2.8–2.9 (2H, m), 3.6–3.7 (2H, m), 5.22 (2H, s), 5.27 (2H, s), 6.87 (1H, d, J=4.2 Hz), 7.39 (1H, d, J=4.2 Hz), 7.5–7.6 (4H, m), 8.00 (1H, s), 8.2–8.3 (4H, m), 8.35–8.5 (1H, m), 11.78 (1H, s)

d) 7-[3-N,N'-Bis(4-nitrobenzyloxycarbonyl) guanidinopropyl]thio-2-(tri-n-butylstannyl)imidazo[5,1-b] thiazole The procedure of Synthesis Example 2c) was repeated, except that 992 mg of 7-[3-N,N'-bis(4-nitrobenzyloxycarbonyl)guanidinopropyl]thioimidazo[5,1-b]thiazole was used as the starting compound. Thus, 710 mg of the title compound was prepared.

NMR (CDCl$_3$) δ: 0.91 (9H, t, J=7.2 Hz), 1.1–1.2 (6H, m), 1.3–1.4 (6H, m), 1.5–1.6 (6H, m), 1.85–1.95 (2H, m), 2.8–2.9 (2H, m), 3.6–3.7 (2H, m), 5.22 (2H, s), 5.27 (2H, s), 7.15 (1H, s), 7.5–7.6 (4H, m), 7.94 (1H, s), 8.15–8.25 (4H, m), 8.4–8.5 (1H, m), 11.78 (1H, s)

Synthesis Example 18

7-Benzylthio-2-(tri-n-butylstannyl)imidazo[5,1-b] thiazole a) 7-Benzylthioimidazo[5,1-b]thiazole A solution of 396 mg of 7-acetylthioimidazo[5,1-b] thiazole in 2 ml of methanol was cooled in ice. A 1.018 M sodium methoxide/methanol solution (2.16 ml) was added to the cooled solution, and the mixture was stirred for 30 min. Benzyl bromide (0.262 ml) was added thereto, and the mixture was stirred at that temperature for 2 hr. An aqueous ammonium chloride solution was added to the reaction solution, and the mixture was extracted with ethyl acetate twice. The organic layer was washed with brine twice, and was dried over anhydrous magnesium sulfate. The solvent was removed by distillation, and the residue was purified by column chromatography on silica gel (dichloromethane:methanol=30:1) to prepare 419 mg of 7-benzylthioimidazo[5,1-b]thiazole.

NMR (CDCl$_3$) δ: 3.99 (2H, s), 6.76 (1H, d, J=4.2 Hz), 7.1–7.25 (5H, m), 7.32 (1H, d, J=4.2 Hz), 7.99 (1H, s)

b) 7-Benzylthio-2-(tri-n-butylstannyl)imidazo[5,1-b]thiazole

The procedure of Synthesis Example 1b) was repeated, except that 330 mg of 7-benzylthioimidazo[5,1-b]thiazole was used as the starting compound. Thus, 602 mg of the title compound was prepared.

NMR (CDCl$_3$) δ: 0.92 (9H, t, J=7.2 Hz), 1.1–1.2 (6H, m), 1.3–1.4 (6H, m), 1.5–1.6 (6H, m), 3.99 (2H, s), 7.08 (1H, s), 7.15–7.2 (5H, m), 7.93 (1H, s)

Synthesis Example 19

7-(Pyridin-2-yl)methylthio-2-(tri-n-butylstannyl)imidazo[5,1-b]thiazole a) 7-(Pyridin-2-yl)methylthioimidazo[5,1-b]thiazole Triphenylphosphine (2.95 g) and 3.73 g of carbon tetrabromide were added to a solution of 0.724 ml of (pyridin-2-yl)methanol in 40 ml of dichloromethane under ice cooling, and the mixture was stirred at that temperature for 1.5 hr. The reaction solution was purified by column chromatography on silica gel (dichloromethane:methanol=30:1) to prepare 2-bromomethylpyridine. A solution of 990 mg of 7-acetylthioimidazo[5,1-b]thiazole in 5 ml of methanol was cooled in ice. A 1.018 M sodium methoxide/methanol solution (5.4 ml) was added to the cooled solution, and the mixture was stirred for 30 min. The above solution of 2-bromomethylpyridine in 5 ml of dichloromethane was added thereto, and the mixture was stirred at room temperature for 20 hr. A saturated aqueous ammonium chloride solution was added to the reaction mixture, and the mixture was extracted with ethyl acetate three times. The organic layer was washed with saturated brine, and was then dried over anhydrous magnesium sulfate. The solvent was removed by distillation, and the residue was purified by column chromatography on silica gel (dichloromethane:methanol=20:1) to prepare 776 mg of 7-(pyridin-2-yl)methylthioimidazo[5,1-b]thiazole.

NMR (CDCl$_3$) δ: 4.12 (2H, s), 6.78 (1H, d, J=4.2 Hz), 7.05–7.15 (2H, m), 7.33 (1H, d, J=4.2 Hz), 7.45–7.55 (1H, m), 7.99 (1H, s), 8.45–8.5 (1H, m)

b) 7-(Pyridin-2-yl)methylthio-2-(tri-n-butylstannyl)imidazo[5,1-b]thiazole

The procedure of Synthesis Example 1b) was repeated, except that 776 mg of 7-(pyridin-2-yl)methylthioimidazo[5,1-b]thiazole was used as the starting compound. Thus, 1.18 g of the title compound was prepared.

NMR (CDCl$_3$) δ: 0.92 (9H, t, J=7.2 Hz), 1.1–1.2 (6H, m), 1.3–1.4 (6H, m), 1.5–1.6 (6H, m), 4.11 (2H, s), 7.05–7.2 (3H, m), 7.45–7.55 (1H, m), 7.92 (1H, s), 8.45–8.5 (1H, m)

Synthesis Example 20

7-(Pyridin-2-yl)thio-2-(tri-n-butylstannyl)imidazo[5,1-b]thiazole a) 7-(Pyridin-2-yl)thioimidazo[5,1-b]thiazole A solution of 661 mg of 7-iodoimidazo[5,1-b]thiazole in 15 ml of dry THF was cooled in ice. A 0.95 M ethylmagnesium bromide/THF solution (2.89 ml) was added to the cooled solution under an argon atmosphere. The mixture was stirred at that temperature for 15 min. A solution of 798 mg of S-(pyridin-2-yl) pyridine-2-thiosulfonate in 10 ml of THF was added thereto, and the mixture was stirred at room temperature for 3 hr. A saturated aqueous ammonium chloride solution was added to the reaction mixture, and the mixture was then extracted with ethyl acetate twice, and the extract was washed with brine. The organic layer was dried over anhydrous magnesium sulfate. The solvent was removed by distillation. The residue was purified by column chromatography on silica gel (ethyl acetate) to prepare 456 mg of 7-(pyridin-2-yl)thioimidazo[5,1-b]thiazole.

NMR (CDCl$_3$) δ: 6.9–7.0 (3H, m), 7.4–7.5 (1H, m), 7.50 (1H, d, J=3.9 Hz), 8.16 (1H, s), 8.35–8.45 (1H, m)

b) 7-(Pyridin-2-yl)thio-2-(tri-n-butylstannyl)imidazo[5,1-b]thiazole

The procedure of Synthesis Example 2c) was repeated, except that 456 mg of 7-(pyridin-2-yl)thioimidazo[5,1-b]thiazole was used as the starting compound. Thus, 760 mg of the title compound was prepared.

NMR (CDCl$_3$) δ: 0.91 (9H, t, J=7.2 Hz), 1.1–1.2 (6H, m), 1.3–1.4 (6H, m), 1.5–1.65 (6H, m), 6.9–7.0 (2H, m), 7.23 (1H, s), 7.35–7.45 (1H, m), 8.09 (1H, s), 8.35–8.45 (1H, m)

Synthesis Example 21

7-((2R)-3-Azido-2-triethylsilyloxypropyl)thio-2-(tri-n-butylstannyl)imidazo[5,1-b]thiazole a) 7-((2R)-3-Azido-2-triethylsilyloxypropyl)thioimidazo[5,1-b]thiazole The procedure of Synthesis Example 11b) was repeated, except that 907 mg of 7-acetylthioimidazo[5,1-b]thiazole and 1.27 g of (2R)-3-azido-2-triethylsilyloxy-1-propanol was used as the starting compound. Thus, 1.44 g of 7-((2R)-3-azido-2-triethylsilyloxypropyl)thioimidazo[5,1-b]thiazole was prepared.

NMR (CDCl$_3$) δ: 0.53 (6H, q, J=7.5 Hz), 0.88 (9H, t, J=7.5 Hz), 2.85–3.0 (2H, m), 3.4–3.6 (2H, m), 3.9–4.0 (1H, m), 6.88 (1H, d, J=4.2 Hz), 7.40 (1H, d, J=4.2 Hz), 7.99 (1H, s)

b) 7-((2R)-3-Azido-2-triethylsilyloxypropyl)thio-2-(tri-n-butylstannyl)imidazo[5,1-b]thiazole The procedure of Synthesis Example 2c) was repeated, except that 1.33 g of 7-((2R)-3-azido-2-triethylsilyloxypropyl)thioimidazo[5,1-b]thiazole was used as the starting compound. Thus, 2.07 g of the title compound was prepared.

NMR (CDCl$_3$) δ: 0.51 (6H, q, J=7.8 Hz), 0.87 (9H, t, J=7.8 Hz), 0.92 (9H, t, J=7.2 Hz), 1.1–1.2 (6H, m), 1.3–1.4 (6H, m), 1.5–1.7 (6H, m), 2.8–3.0 (2H, m), 3.4–3.6 (2H, m), 3.9–4.0 (1H, m), 7.14 (1H, s), 7.93 (1H, s)

Synthesis Example 22

7-(Pyridin-4-yl)thio-2-(tri-n-butylstannyl)imidazo[5,1-b]thiazole a) 7-(Pyridin-4-yl)thioimidazo[5,1-b]thiazole A solution of 2.5 g of 7-iodoimidazo[5,1-b]thiazole in 40 ml of dry THF was cooled in ice. A 0.95 M ethylmagnesium bromide/THF solution (11.7 ml) was added to the cooled solution under an argon atmosphere. The mixture was stirred at that temperature for 40 min. 4,4'-Dipyridyl disulfide (3.3 g) was added thereto, and the mixture was stirred at room temperature for 18 hr. A saturated aqueous ammonium chloride solution was added to the reaction mixture, and the mixture was then extracted with ethyl acetate twice. The extract was washed with brine, and the organic layer was dried over anhydrous magnesium sulfate. The solvent was removed by distillation. The residue was purified by column chromatography on silica gel (dichloromethane:methanol= 30:1 to 20:1) and by column chromatography on Sephadex LH-20 (dichloromethane:methanol=1:1) to prepare 1.09 g of 7-(pyridin-4-yl)thioimidazo[5,1-b]thiazole.

NMR (CDCl$_3$) δ: 6.95–7.0 (3H, m), 7.53 (1H, d, J=3.9Hz), 8.16 (1H, s), 8.3–8.4 (2H, m)

b) 7-(Pyridin-4-yl)thio-2-(tri-n-butylstannyl)imidazo[5,1-b]thiazole

The procedure of Synthesis Example 1b) was repeated, except that 1.09 g of 7-(pyridin-4-yl)thioimidazo[5,1-b]thiazole was used as the starting compound. Thus, 1.78 g of the title compound was prepared.

NMR (CDCl$_3$) δ: 0.91 (9H, t, J=7.2 Hz), 1.1–1.2 (6H, m), 1.3–1.4 (6H, m), 1.5–1.6 (6H, m), 6.95–7.0 (2H, m), 7.25 (1H, s), 8.09 (1H, s), 8.3–8.35 (2H, m)

Synthesis Example 23

7-(Pyridin-4-yl)sulfonyl-2-(tri-n-butylstannyl)imidazo[5,1-b]thiazole

A solution of 1.24 g of 7-(pyridin-4-yl)thio-2-(tri-n-butylstannyl)imidazo[5,1-b]thiazole in 25 ml of dichloromethane was cooled in ice, and 1.64 g of 3-chloroperbenzoic acid was added to the cooled solution. The mixture was stirred at that temperature for 2 hr. The reaction solution was diluted with dichloromethane. The diluted solution was washed with an aqueous sodium thiosulfate solution and an aqueous sodium hydrogencarbonate solution in that order and was then dried over anhydrous magnesium sulfate. The solvent was removed by distillation. The residue was purified by column chromatography on silica gel (hexane:ethyl acetate=1:1 to 1:2) to prepare 741 mg of the title compound.

NMR (CDCl$_3$) δ: 0.92 (9H, t, J=7.5 Hz), 1.15–1.25 (6H, m), 1.3–1.4 (6H, m), 1.5–1.65 (6H, m), 7.25 (1H, s), 7.85–7.9 (2H, m), 7.96 (1H, s), 8.8–8.85 (2H, m)

Example 1

Sodium (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate a) 4-Nitrobenzyl (1S,5R,6S)-2-[7-(2-t-butyldimethylsilyloxyethyl)thioimidazo[5,1-b]thiazol-2-yl]-6-((1R)-1-hydroxyethyl)-1-methyl-1-carbapen-2-em-3-carboxylate N,N-Diisopropylethylamine (0.574 ml) was added dropwise to a solution of 791 mg of 4-nitrobenzyl (1R,3R,5R,6S)-6-((1R)-1-hydroxyethyl)-1-methyl-2-oxo-1-carbapenam-3-carboxylate in 20 ml of dry acetonitrile at −30° C. under an argon atmosphere, followed by the dropwise addition of 0.367 ml of trifluoromethanesulfonic anhydride under the same conditions. The mixture was stirred at that temperature for 30 min. Ethyl acetate (40 ml) was then added thereto, and the mixture was washed with semi-saturated brine, a mixed solution composed of semi-saturated brine with a 1 N aqueous hydrochloric acid solution (pH 1.1), a mixed solution composed of semi-saturated brine with a saturated aqueous sodium hydrogencarbonate solution (pH 8.9), and semi-saturated brine in that order, dried over anhydrous magnesium sulfate, and then filtered. The solvent was removed by distillation under the reduced pressure. The residue was dissolved in 10 ml of dry N-methylpyrrolidinone. Tri-2-furylphosphine (11 mg), 104 mg of zinc chloride, 11 mg of tris(dibenzylideneacetone)dipalladium(0), and 1.433 g of 7-(2-t-butyldimethylsilyloxyethyl)thio-2-(tri-n-butylstannyl)imidazo[5,1-b]thiazole were added to the solution. The mixture was stirred at 50° C. under an argon atmosphere for 1.5 hr. Ethyl acetate (30 ml) and 15 ml of a semi-saturated aqueous sodium hydrogencarbonate solution were added to the reaction solution. The mixture was stirred, and the insolubles were removed by filtration. The organic layer was separated from the filtrate, washed with 20 ml of semi-saturated brine three times, and then dried over anhydrous magnesium sulfate. The solvent was removed by distillation under the reduced pressure. The residue was purified by column chromatography on silica gel (dichloromethane:methanol=20:1) to prepare 573 mg of 4-nitrobenzyl (1S,5R,6S)-2-[7-(2-t-butyldimethylsilyloxyethyl)thioimidazo[5,1-b]thiazole-2-yl]-6-((1R)-1-hydroxyethyl)-1-methyl-1-carbapen-2-em-3-carboxylate.

NMR (CDCl$_3$) δ: 0.02 (6H, s), 0.86 (9H, s), 1.31 (3H, d, J=7.3 Hz), 1.40 (3H, d, J=6.3 Hz), 2.9–3.0 (2H, m), 3.37 (1H, dd, J$_1$=6.6 Hz, J$_2$=2.8 Hz), 3.4–3.5 (1H, m), 3.75–3.85 (2H, m), 4.25–4.35 (1H, m), 4.38 (1H, dd, J$_1$=9.6 Hz, J$_2$2.8 Hz), 5.28 (1H, d, J=13.7 Hz), 5.53 (1H, d, J=13.7 Hz), 7.68 (2H, d, J=8.9 Hz), 8.00 (1H, s), 8.25 (2H, d, J=8.9 Hz), 8.32 (1H, s)

b) 4-Nitrobenzyl (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate Acetic acid (0.207 ml) and 1.21 ml of a 1 M tetra-n-butylammonium fluoride/THF solution were added to a solution of 265 mg of 4-nitrobenzyl (1S,5R,6S)-2-[7-(2-t-butyldimethylsilyloxyethyl)thioimidazo[5,1-b]thiazol-2-yl]-6-((1R)-1-hydroxyethyl)-1-methyl-1-carbapen-2-em-3-carboxylate in 5 ml of THF. The mixture was stirred at room temperature for 6 hr. Brine was added to the reaction solution, and a saturated sodium hydrogencarbonate solution was added thereto. The mixture was adjusted to pH 8.2, and was extracted with ethyl acetate twice. The organic layers were combined, were washed with brine, and were dried over anhydrous magnesium sulfate. The solvent was then removed by distillation under the reduced pressure. The residue was purified by column chromatography on silica gel (dichloromethane:methanol=20:1) to prepare 208 mg of 4-nitrobenzyl (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate.

NMR (CDCl$_3$) δ: 1.31 (3H, d, J=7.4 Hz), 1.40 (3H, d, J=6.3 Hz), 2.9–3.0 (2H, m), 3.37 (1H, dd, J$_1$=6.4 Hz, J$_2$=2.7 Hz), 3.4–3.5 (1H, m), 3.8–3.9 (2H, m), 4.0 (1H, br s), 4.3–4.4 (1H, m), 4.38 (1H, dd, J$_1$=9.7 Hz, J$_2$=2.7 Hz), 5.28 (1H, d, J=13.7 Hz), 5.53 (1H, d, J=13.7 Hz), 7.68 (2H, d, J=8.4 Hz), 8.02 (1H, s), 8.25 (2H, d, J=8.4 Hz), 8.29 (1H, s)

c) Sodium (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate 4-Nitrobenzyl (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate (48.4 mg) was dissolved in 2.5 ml of THF and 2.5 ml of a 1/15 M sodium phosphate buffer (pH 6.6). 10% Pd-C (50 mg) was added to the solution. The air in the reaction vessel was replaced by hydrogen, and the contents of the reaction vessel were stirred at room temperature for 2 hr. The catalyst was removed by filtration on Celite, and was washed with water. The filtrate was washed with ethyl acetate, and was then concentrated under the reduced pressure to bring the volume of the solution to about 1 ml. The residue was purified by column chromatography on Cosmosil $40C_{18}$-PREP (20% aqueous methanol solution) to prepare 15.8 mg of the title compound.

NMR ($D_2O$) δ(HOD=4.80 ppm): 1.21 (3H, d, J=7.1 Hz), 1.31 (3H, d, J=6.4 Hz), 2.8–2.9 (2H, m), 3.45–3.6 (2H, m), 3.6–3.7 (2H, m), 4.2–4.35 (2H, m), 7.84 (1H, s), 8.12 (1H, s)

Example 2

Sodium (1S,5R,6S)-6-((1R)-1-hydroxyethyl)-2-[7-(2-hydroxyethyl)sulfinylimidazo[5,1-b]thiazol-2-yl]-1-methyl-1-carbapen-2-em-3-carboxylate (a mixture of diastereomers)

a) 4-Nitrobenzyl (1S,5R,6S)-6-((1R)-1-hydroxyethyl)-2-[7-(2-hydroxyethyl)sulfinylimidazo[5,1-b]thiazol-2-yl]-1-methyl-1-carbapen-2-em-3-carboxylate (a mixture of diastereomers) and 4-nitrobenzyl (1S,5R,6S)-6-((1R)-1-hydroxyethyl)-2-[7-(2-hydroxyethyl)sulfonylimidazole[5,1-b]thiazol-2-yl]-1-methyl-1-carbapen-2-em-3-carboxylate OXONE (manufactured by Dupont) (248.9 mg) was added to a mixed solution composed of 248.9 mg of 4-nitrobenzyl (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate, 2.5 ml of THF, and 2.5 ml of water under ice cooling. The mixture was stirred at that temperature for 30 min. A saturated aqueous sodium hydrogencarbonate solution was then added thereto, and the mixture was extracted with dichloromethane. The organic layer was dried over anhydrous magnesium sulfate. The solvent was removed by distillation, and the residue was purified by column chromatography on silica gel (dichloromethane:methanol=40:1) to prepare 93 mg of 4-nitrobenzyl (1S,5R,6S)-6-((1R)-1-hydroxyethyl)-2-[7-(2-hydroxyethyl)sulfinylimidazo[5,1-b]thiazol-2-yl]-1-methyl-1-carbapen-2-em-3-carboxylate (a mixture of diastereomers) and 55 mg of 4-nitrobenzyl (1S,5R,6S)-6-((1R)-1-hydroxyethyl)-2-[7-(2-hydroxyethyl)sulfonylimidazo[5,1-b]thiazol-2-yl]-1-methyl-1-carbapen-2-em-3-carboxylate.

4-Nitrobenzyl (1S,5R,6S)-6-((1R)-1-hydroxyethyl)-2-[7-(2-hydroxyethyl)sulfinylimidazo[5,1-b]thiazol-2-yl]-1-methyl-1-carbapen-2-em-3-carboxylate (a mixture of diastereomers):

NMR ($CDCl_3$) δ: 1.30 (3H, m), 1.39 (3H, d, J=6.3 Hz), 3.30 (1H, m), 3.90 (2H, m), 3.98 (2H, m), 4.19 (2H, m), 4.31 (1H, m), 5.28 (1H, d, J=13.7 Hz), 5.52 (1H, d, J=13.7 Hz), 7.68 (2H, d, J=8.3 Hz), 8.12 (1H, s), 8.25 (2H, d, J=8.3 Hz), 8.45, 8.46 (total 1H, s each)

4-Nitrobenzyl (1S,5R,6S)-6-((1R)-1-hydroxyethyl)-2-[7-(2-hydroxyethyl)sulfonylimidazo[5,1-b]thiazol-2-yl]-1-methyl-1-carbapen-2-em-3-carboxylate:

NMR ($CDCl_3$) δ: 1.31 (3H, d, J=7.2 Hz), 1.40 (3H, d, J=6.3 Hz), 3.40 (1H, m), 3.90 (2H, m), 3.98 (2H, m), 4.19 (2H, m), 4.31 (1H, m), 4.41 (1H, dd, $J_1$=9.7 Hz, $J_2$=3.1 Hz), 5.28 (1H, d, J=13.5 Hz), 5.52 (1H, d, J=13.5 Hz), 7.69 (2H, d, J=8.8 Hz), 8.09 (1H, s), 8.24 (2H, d, J=8.8 Hz), 8.40 (1H, s)

b) Sodium (1S,5R,6S)-6-((1R)-1-hydroxyethyl)-2-[7-(2-hydroxyethyl)sulfinylimidazo[5,1-b]thiazol-2-yl)-1-methyl-1-carbapen-2-em-3-carboxylate (a mixture of diastereomers)

4-Nitrobenzyl (1S,5R,6S)-6-((1R)-1-hydroxyethyl)-2-[7-(2-hydroxyethyl)sulfinylimidazo[5,1-b]thiazol-2-yl]-1-methyl-1-carbapen-2-em-3-carboxylate (a mixture of diastereomers) (50.1 mg) was dissolved in 1.8 ml of THF and 1.8 ml of a 1/15 M sodium phosphate buffer (pH 6.6). 10% Pd-C (54.7 mg) was added to the solution. The air in the reaction vessel was replaced by hydrogen, and the contents of the reaction vessel were stirred at room temperature for 50 min. The catalyst was removed by filtration on Celite, and was washed with water. The filtrate was adjusted to pH 7.0 by the addition of an aqueous sodium hydrogencarbonate solution, and was then washed with ethyl acetate. The aqueous layer was then purified by column chromatography on Cosmosil $40C_{18}$-PREP (only water) to prepare 21.4 mg of the title compound.

NMR ($D_2O$) δ(HOD=4.80 ppm): 1.22 (3H, d, J=7.1 Hz), 1.32 (3H, d, J=6.4 Hz), 3.40 (1H, m), 3.51 (1H, m), 3.58 (2H, m), 3.97 (2H, m), 4.27 (2H, m), 7.98, 8.00 (total 1H, s each), 8.24, 8.25 (total 1H, s each)

Example 3

Sodium (1S,5R,6S)-6-((1R)-1-hydroxyethyl)-2-[7-(2-hydroxyethyl)sulfonylimidazo[5,1-b]thiazol-2-yl]-1-methyl-1-carbapen-2-em-3-carboxylate The procedure of Example 2b) was repeated, except that 34.0 mg of 4-nitrobenzyl (1S,5R,6S)-6-((1R)-1-hydroxyethyl)-2-[7-(2-hydroxyethyl)sulfonylimidazo[5,1-b]thiazol-2-yl]-1-methyl-1-carbapen-2-em-3-carboxylate was used as the starting compounds. Thus, 9.2 mg of the title compound was prepared.

NMR ($D_2O$) δ(HOD=4.80 ppm): 1.25 (3H, d, J=7.1 Hz), 1.33 (3H, d, J=6.4 Hz), 3.52 (1H, m), 3.63 (3H, m), 3.98 (2H, t, J=5.9 Hz), 4.30 (2H, m), 8.05 (1H, s), 8.26 (1H, s)

Example 4

Sodium (5R,6S)-6-((1R)-1-hydroxyethyl)-2-[7-(2-hydroxyethyl)thioimidazo[5,1-b]thiazol-2-yl)-1-carbapen-2-em-3-carboxylate a) 4-Nitrobenzyl (5R,6S)-2-[7-(2-t-butyldimethylsilyloxyethyl)thioimidazo[5,1-b]thiazol-2-yl]-6-((1R)-1-hydroxyethyl)-1-carbapen-2-em-3-carboxylate The procedure of Example 1a) was repeated, except that 752 mg of 4-nitrobenzyl (3R,5R,6S)-6-((1R)-1-hydroxyethyl)-2-oxo-1-carbapenam-3-carboxylate and 1.433 g of 7-(2-t-butyldimethylsilyloxyethyl)thio-2-(tri-n-butylstannyl)imidazo[5,1-b]thiazole were used as the starting compounds. Thus, 703 mg of 4-nitrobenzyl (5R,6S)-2-[7-(2-t-butyldimethylsilyloxyethyl)thioimidazo[5,1-b]thiazol-2-yl]-6-((1R)-1-hydroxyethyl)-1-carbapen-2-em-3-carboxylate was prepared.

NMR ($CDCl_3$) δ: 0.02 (6H, s), 0.86 (9H, s), 1.40 (3H, d, J=6.3 Hz), 2.9–3.0 (2H, m), 3.3–3.4 (3H, m), 3.75–3.85 (2H, m), 4.3–4.4 (2H, m), 5.31 (1H, d, J=13.6 Hz), 5.55 (1H, d, J=13.6 Hz), 7.69 (2H, d, J=8.8 Hz), 7.99 (1H, s), 8.21 (1H, s), 8.25 (2H, d, J=8.9 Hz)

b) 4-Nitrobenzyl (5R,6S)-6-((1R)-1-hydroxyethyl)-2-[7-(2-hydroxyethyl)thioimidazo[5,1-b]thiazol-2-yl]-1-carbapen-2-em-3-carboxylate The procedure of Example 1b) was repeated, except that 238 mg of 4-nitrobenzyl (5R,6S)-2-[7-(2-t-butyldimethylsilyloxyethyl)thioimidazo[5,1-b]thiazol-2-yl]-6-((1R)-1-hydroxyethyl)-1-carbapen-2-em-3-carboxylate was used as the starting compound. Thus, 152 mg of 4-nitrobenzyl (5R,6S)-6-((1R)-1-hydroxyethyl)-2-[7-(2-hydroxyethyl)thioimidazo[5,1-b]thiazol-2-yl]-1-carbapen-2-em-3-carboxylate was prepared.

NMR ($CDCl_3$) δ: 1.40 (3H, d, J=6.3 Hz), 2.90–2.96 (2H, m), 3.28–3.37 (2H, m), 4.26–4.40 (2H, m), 5.32 (1H, d,

J=13.5 Hz), 5.55 (1H, d, J=13.5 Hz), 7.70 (2H, d, J=8.7 Hz), 8.01 (1H, s), 8.17 (1H, s), 8.25 (2H, d, J=8.9 Hz)

c) Sodium (5R,6S)-6-((1R)-1-hydroxyethyl)-2-[7-(2-hydroxyethyl)thioimidazo[5,1-b]thiazol-2-yl]-1-carbapen-2-em-3-carboxylate The procedure of Example 1c) was repeated, except that 69 mg of 4-nitrobenzyl (5R,6S)-6-((1R)-1-hydroxyethyl)-2-[7-(2-hydroxyethyl)thioimidazo[5,1-b]-thiazol-2-yl]-1-carbapen-2-em-3-carboxylate was used as the starting compound. Thus, 26.5 mg of the title compound was prepared.

NMR (D$_2$O) δ(HOD=4.80 ppm): 1.31 (3H, d, J=6.3 Hz), 2.70–2.80 (2H, m), 3.06–3.26 (2H, m), 3.47 (1H, dd, J$_1$=5.9 Hz, J$_2$=2.8 Hz), 3.60–3.65 (2H, m), 4.16–4.30 (2H, m), 7.55 (1H, s), 7.97 (1H, s)

Example 5

Sodium (1S,5R,6S)-2-[7-(2-aminoethyl)thioimidazo[5,1-b]thiazol-2-yl]-6-((1R)-1-hydroxyethyl)-1-methyl-1-carbapen-2-em-3-carboxylate a) 4-Nitrobenzyl (1S,5R,6S)-2-[7-(2-azidoethyl)thioimidazo[5,1-b]thiazol-2-yl]-6-((1R)-1-hydroxyethyl)-1-methyl-1-carbapen-2-em-3-carboxylate The procedure of Example 1a) was repeated, except that 3.10 g of 4-nitrobenzyl (1R,3R,5R,6S)-6-((1R)-1-hydroxyethyl)-1-methyl-2-oxo-1-carbapenam-3-carboxylate and 4.62 g of 7-(2-azidoethyl)thio-2-(tri-n-butylstannyl)imidazo[5,1-b]thiazole were used as the starting compounds. Thus, 3.41 g of 4-nitrobenzyl (1S,5R,6S)-2-[7-(2-azidoethyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.31 (3H, d, J=7.4 Hz), 1.40 (3H, d, J=6.3 Hz), 2.95–3.05 (2H, m), 3.37 (1H, dd, J$_1$=6.5 Hz, J$_2$=2.8 Hz), 3.4–3.55 (3H, m), 4.25–4.35 (1H, m), 4.38 (1H, dd, J$_1$=9.6 Hz, J$_2$=2.8 Hz), 5.28 (1H, d, J=13.7 Hz), 5.53 (1H, d, J=13.7 Hz), 7.68 (2H, d, J=8.6 Hz), 8.03 (1H, s), 8.25 (2H, d, J=8.6 Hz), 8.32 (1H, s)

b) Sodium (1S,5R,6S)-2-[7-(2-aminoethyl)thioimidazo[5,1-b]thiazol-2-yl]-6-((1R)-1-hydroxyethyl)-1-methyl-1-carbapen-2-em-3-carboxylate The procedure of Example 1c) was repeated, except that 1.46 g of 4-nitrobenzyl (1S,5R,6S)-2-[7-(2-azidoethyl)thioimidazo[5,1-b]thiazol-2-yl]-6-((1R)-1-hydroxyethyl)-1-methyl-1-carbapen-2-em-3-carboxylate was used as the starting compound for the reaction. Purification was performed by column chromatography on Cosmosil 40C$_{18}$-PREP (an 10 to 25% aqueous methanol solution), and the finally eluted main product was collected to prepare 335 mg of the title compound.

NMR (D$_2$O) δ(HOD=4.80 ppm): 1.22 (3H, d, J=7.1 Hz), 1.32 (3H, d, J=6.5 Hz), 2.92–3.00 (2H, m), 3.06–3.14 (2H, m), 3.46–3.60 (2H, m), 4.22–4.35 (2H, m), 7.82 (1H, s), 8.11 (1H, s)

Example 6

Sodium (1S,5R,6S)-6-((1R)-1-hydroxyethyl)-1-methyl-2-[7-(2-phosphonoxyethyl)thioimidazo[5,1-b]-thiazol-2-yl]-1-carbapen-2-em-3-carboxylate A fraction was collected which had been eluted first in the column chromatography on Cosmosil 40C$_{18}$-PREP (a 10 to 25% aqueous methanol solution) in Example 5b). Thus, 60 mg of the title compound was prepared.

NMR (D$_2$O) δ(HOD=4.80 ppm): 1.26 (3H, d, J=6.6 Hz), 1.33 (3H, d, J=6.2 Hz), 2.95–3.05 (2H, m), 3.5–3.65 (2H, m), 3.85–4.0 (2H, m), 4.2–4.35 (2H, m), 7.95 (1H, s), 8.18 (1H, s)

Example 7

Sodium (1S,5R,6S)-2-[7-(2-azidoethyl)thioimidazo[5,1-b]thiazol-2-yl]-6-((1R)-1-hydroxyethyl)-1-methyl-1-carbapen-2-em-3-carboxylate A fraction was collected which had been eluted second in the column chromatography on Cosmosil 40C$_{18}$-PREP (a 10 to 25% aqueous methanol solution) in Example 5b). Thus, 47 mg of the title compound was prepared.

NMR (D$_2$O) δ(HOD=4.80 ppm): 1.26 (3H, d, J=7.1 Hz), 1.32 (3H, d, J=6.3 Hz), 2.9–3.0 (2H, m), 3.4–3.65 (4H, m), 4.25–4.35 (2H, m), 7.94 (1H, s), 8.17 (1H, s)

Example 8

Sodium (5R,6S)-2-[7-(2-aminoethyl)thioimidazo[5,1-b]thiazol-2-yl]-6-((1R)-1-hydroxyethyl)-1-carbapen-2-em-3-carboxylate a) 4-Nitrobenzyl (5R,6S)-6-((1R)-1-hydroxyethyl)-2-[7-[2-(4-nitrobenzyloxycarbonyl)aminoethyl]thioimidazo[5,1-b]thiazol-2-yl]-1-carbapen-2-em-3-carboxylate The procedure of Example 1a) was repeated, except that 201 mg of 4-nitrobenzyl (3R,5R,6S)-6-((1R)-1-hydroxyethyl)-2-oxo-1-carbapenam-3-carboxylate and 424 mg of 7-[2-(4-nitrobenzyloxycarbonyl)aminoethyl]thio-2-(tri-n-butylstannyl)imidazo[5,1-b]thiazole were used as the starting compounds. Thus, 200 mg of 4-nitrobenzyl (5R,6S)-6-((1R)-1-hydroxyethyl)-2-[7-[2-(4-nitrobenzyloxycarbonyl)aminoethyl]thioimidazo[5,1-b]thiazol-2-yl]-1-carbapen-2-em-3-carboxylate was prepared.

NMR (CDCl$_3$) δ: 1.40 (3H, d, J=6.3 Hz), 2.86–2.94 (2H, m), 3.28–3.37 (3H, m), 3.40–3.48 (2H, m), 4.28–4.40 (2H, m), 5.19 (2H, s), 5.31 (1H, d, J=13.5 Hz), 5.54 (1H, d, J=13.5 Hz), 6.10 (1H, br s), 7.48 (2H, d, J=8.6 Hz), 7.69 (2H, d, J=8.9 Hz), 8.00 (1H, s), 8.17 (1H, s), 8.19 (2H, d, J=8.6 Hz), 8.24 (2H, d, J=8.9 Hz)

b) Sodium (5R,6S)-2-[7-(2-aminoethyl)thioimidazo-[5,1-b]thiazol-2-yl]-6-((1R)-1-hydroxyethyl)-1-carbapen-2-em-3-carboxylate The procedure of Example 1c) was repeated, except that 200 mg of 4-nitrobenzyl (5R,6S)-6-((1R)-1-hydroxyethyl)-2-[7-[2-(4-nitrobenzyloxycarbonyl)aminoethyl]thioimidazo[5,1-b]thiazol-2-yl]-1-carbapen-2-em-3-carboxylate was used as the starting compound. Thus, 44.4 mg of the title compound was prepared.

NMR (D$_2$O) δ(HOD=4.80 ppm): 1.34 (3H, d, J=6.3 Hz), 2.98–3.06 (2H, m), 3.11–3.18 (2H, m), 3.24–3.34 (2H, m), 3.53 (1H, dd, J$_1$=5.9 Hz, J$_2$=2.4 Hz), 4.24–4.35 (2H, m), 7.71 (1H, s), 8.14 (1H, s)

Example 9

Sodium (1S,5R,6S)-2-(7-carbamoylmethylthio-5-methylthioimidazo[5,1-b]thiazol-2-yl)-6-((1R)-1-hydroxyethyl)-1-methyl-1-carbapen-2-em-3-carboxylate a) 4-Nitrobenzyl (1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate The procedure of Example 1a) was repeated, except that 762 mg of 4-nitrobenzyl (1R,3R,5R,6S)-6-((1R)-1-hydroxyethyl)-1-methyl-2-oxo-1-carbapenam-3-carboxylate and 1.10 g of 5,7-bis(methylthio)-2-(tri-n-butylstannyl)imidazo[5,1-b]thiazole were used as the starting compounds. Thus, 720 mg of 4-nitrobenzyl (1S,5R,6S)-2-[5,7-bis(methylthio)imidazo[5,1-b]thiazol-2-yl]-6-((1R)-1-hydroxyethyl)-1-methyl-1-carbapen-2-em-3-carboxylate was prepared.

NMR (CDCl$_3$) δ: 1.31 (3H, d, J=7.3 Hz), 1.39 (3H, d, J=6.3 Hz), 2.43 (3H, s), 2.58 (3H, s), 3.34–3.38 (1H, m), 3.47–3.52 (1H, m), 4.28–4.35 (2H, m), 5.28 (1H, d, J=13.7 Hz), 5.53 (1H, d, J=13.4 Hz), 7.67 (2H, d, J=9.0 Hz), 8.13 (1H, s), 8.23 (2H, d, J=9.0 Hz)

b) 4-Nitrobenzyl (1S,5R,6S)-2-(7-carbamoylmethylthio-5-methylthioimidazo[5,1-b]thiazol-2-yl)-6-((1R)-1-hydroxyethyl)-1-methyl-1-carbapen-2-em-3-carboxylate 4-Nitrobenzyl (1S,5R,6S)-2-[5,7-bis(methylthio)imidazo [5,1-b]thiazol-2-yl]-6-((1R)-1-hydroxyethyl)-1-methyl-1-carbapen-2-em-3-carboxylate (107 mg) was dissolved in 2 ml of acetone. 2-Iodoacetamide (353 mg) was added to the solution. The mixture was stirred at room temperature for 14 days. The solvent was removed by distillation under the reduced pressure. The residue was purified by column chromatography on Sephadex LH-20 (chloroform:methanol=1:1) to prepare 88 mg of 4-nitrobenzyl (1S,5R,6S)-2-(7-carbamoylmethylthio-5-methylthioimidazo[5,1-b]thiazol-2-yl)-6-((1R)-1-hydroxyethyl)-1-methyl-1-carbapen-2-em-3-carboxylate as a crude product.

c) Sodium (1S,5R,6S)-2-(7-carbamoylmethylthio-5-methylthioimidazo[5,1-b]thiazol-2-yl)-6-((1R)-1-hydroxyethyl)-1-methyl-1-carbapen-2-em-3-carboxylate The procedure of Example 1c) was repeated, except that 88 mg of 4-nitrobenzyl (1S,5R,6S)-2-(7-carbamoylmethylthio-5-methylthioimidazo[5,1-b]thiazol-2-yl)-6-((1R)-1-hydroxyethyl)-1-methyl-1-carbapen-2-em-3-carboxylate as a crude product was used as the starting compound. Thus, 7 mg of the title compound was prepared.

NMR (D$_2$O) δ(HOD=4.65 ppm): 1.13 (3H, d, J=7.3 Hz), 1.21 (3H, d, J=6.3 Hz), 2.38 (3H, s), 3.27 (2H, s), 3.40 (1H, dd, J$_1$=6.1 Hz, J$_2$=2.7 Hz), 3.44–3.53 (1H, m), 4.13–4.23 (2H, m), 7.72 (1H, s)

Example 10

(1S,5R,6S)-6-((1R)-1-Hydroxyethyl)-1-methyl-2-[7-[2-(pyridinium-1-yl)ethyl]thioimidazo[5,1-b]thiazol-2-yl]-1-carbapen-2-em-3-carboxylate (intramolecular salt)

a) 4-Nitrobenzyl (1S,5R,6S)-6-((1R)-1-hydroxyethyl)-2-[7-(2-methanesulfonyloxyethyl)thioimidazo[5,1-b]thiazol-2-yl]-1-methyl-1-carbapen-2-em-3-carboxylate 4-Nitrobenzyl (1S,5R,6S)-6-((1R)-1-hydroxyethyl)-2-[7-(2-hydroxyethyl)thioimidazo[5,1-b]thiazol-2-yl]-1-methyl-1-carbapen-2-em-3-carboxylate (62.8 mg) was dissolved in 2 ml of dichloromethane. N,N-Diisopropylethylamine (0.040 ml) and 0.011 ml of methanesulfonyl chloride were added to the solution at −50° C. The mixture was stirred at that temperature for 40 min. The reaction solution was then diluted with dichloromethane, and the diluted solution was washed with water. The organic layer was dried over anhydrous magnesium sulfate. The solvent was then removed by distillation under the reduced pressure. The residue was purified by column chromatography on silica gel (dichloromethane:methanol=20:1) to prepare 40.9 mg of 4-nitrobenzyl (1S,5R,6S)-6-((1R)-1-hydroxyethyl)-2-[7-(2-methanesulfonyloxyethyl)thioimidazo[5,1-b]thiazol-2-yl]-1-methyl-1-carbapen-2-em-3-carboxylate.

NMR (CDCl$_3$) δ: 1.32 (3H, d, J=7.2 Hz), 1.40 (3H, d, J=6.2 Hz), 3.08 (3H, s), 3.05–3.15 (2H, m), 3.38 (1H, dd, J$_1$=6.6 Hz, J$_2$=2.8 Hz), 3.4–3.5 (1H, m), 4.25–4.45 (4H, m), 5.28 (1H, d, J=13.8 Hz), 5.53 (1H, d, J=13.8 Hz), 7.68 (2H, d, J=8.5 Hz), 8.03 (1H, s), 8.24 (2H, d, J=8.5 Hz), 8.30 (1H, s)

b) (1S,5R,6S)-6-((1R)-1-Hydroxyethyl)-1-methyl-2-[7-[2-(pyridinium-1-yl)ethyl]thioimidazo[5,1-b]thiazol-2-yl]-1-carbapen-2-em-3-carboxylate (intramolecular salt)

4-Nitrobenzyl (1S,5R,6S)-6-((1R)-1-hydroxyethyl)-2-[7-(2-methanesulfonyloxyethyl)thioimidazo[5,1-b]thiazol-2-yl]-1-methyl-1-carbapen-2-em-3-carboxylate (77.6 mg) was dissolved in 4 ml of pyridine. The solution was stirred at room temperature for 3 days. The reaction solution was concentrated under the reduced pressure. The residue was purified by column chromatography on Sephadex LH-20 (chloroform:methanol=1:1). The residue was reacted in the same manner as in Example 1c), and the reaction product was purified by column chromatography on Cosmosil 40C$_{18}$-PREP (a 5 to 30% aqueous methanol solution). A main product was collected which had been eluted as the latter fraction. Thus, 17.4 mg of the title compound was prepared.

NMR (D$_2$O) δ(HOD=4.80 ppm): 1.23 (3H, d, J=7.1 Hz), 1.32 (3H, d, J=6.1 Hz), 3.4–3.6 (4H, m), 4.2–4.35 (2H, m), 4.7–4.8 (2H, m), 7.72 (1H, s), 7.8–7.9 (2H, m), 7.94 (1H, s), 8.25–8.35 (1H, m) 8.65–8.75 (2H, m)

Example 11

(5R,6S)-6-((1R)-1-Hydroxyethyl)-2-[7-[2-(pyridinium-1-yl)ethyl]thioimidazo[5,1-b]thiazol-2-yl]-1-carbapen-2-em-3-carboxylate (intramolecular salt)

a) 4-Nitrobenzyl (5R,6S)-6-((1R)-1-hydroxyethyl)-2-[7-(2-methanesulfonyloxyethyl)thioimidazo[5,1-b]thiazol-2-yl]-1-carbapen-2-em-3-carboxylate The procedure of Example 10a) was repeated, except that 303 mg of 4-nitrobenzyl (5R,6S)-6-((1R)-1-hydroxyethyl)-2-[7-(2-hydroxyethyl)thioimidazo[5,1-b]thiazol-2-yl]-1-carbapen-2-em-3-carboxylate was used as the starting compound. Thus, 154 mg of 4-nitrobenzyl (5R,6S)-6-((1R)-1-hydroxyethyl)-2-[7-(2-methanesulfonyloxyethyl) thioimidazo[5,1-b]thiazol-2-yl]-1-carbapen-2-em-3-carboxylate was prepared.

NMR (DMSO-d$_6$) δ: 1.17 (3H, d, J=6.4 Hz), 3.0–3.1 (2H, m), 3.19 (3H, s), 3.3–3.55 (3H, m), 3.95–4.05 (1H, m), 4.2–4.35 (3H, m), 5.42 (1H, d, J=13.8 Hz), 5.55 (1H, d, J=13.8 Hz), 7.76 (2H, d, J=8.5 Hz), 8.25 (2H, d, J=8.9 Hz), 8.31 (1H, s), 8.37 (1H, s)

b) (5R,6S)-6-((1R)-1-Hydroxyethyl)-2-[7-[2-(pyridinium-1-yl)ethyl]thioimidazo[5,1-b]thiazol-2-yl]-1-carbapen-2-em-3-carboxylate (intramolecular salt)

The procedure of Example 10b) was repeated, except that 84 mg of 4-nitrobenzyl (5R,6S)-6-((1R)-1-hydroxyethyl)-2-[7-(2-methanesulfonyloxyethyl)thioimidazo[5,1-b]thiazol-2-yl]-1-carbapen-2-em-3-carboxylate was used as the starting compound. Thus, 4.7 mg of the title compound was prepared.

NMR (D$_2$O) δ(HOD=4.80 ppm): 1.33 (3H, d, J=6.3 Hz), 3.15–3.3 (2H, m), 3.4–3.55 (3H, m), 4.2–4.35 (2H, m), 4.7–4.8 (2H, m), 7.56 (1H, s), 7.8–7.9 (2H, m), 7.94 (1H, s), 8.3–8.4 (1H, m) 8.7–8.8 (2H, m)

Example 12

Sodium (1S,5R,6S)-2-[7-(2-formimidoylaminoethyl) thioimidazo[5,1-b]thiazol-2-yl]-6-((1R)-1-hydroxyethyl)-1-methyl-1-carbapen-2-em-3-carboxylate Sodium (1S,5R,6S)-2-[7-(2-aminoethyl)thioimidazo[5,1-b]thiazol-2-yl]-6-((1R)-1-hydroxyethyl)-1-methyl-1-carbapen-2-em-3-carboxylate (45.7 mg) was suspended in 3 ml of water under ice cooling. Ethylformimidate hydrochloride (46 mg) was added to the suspension. While adjusting the mixture to pH 8 to 9 by the addition of an aqueous sodium carbonate solution, the mixture was stirred at that temperature for one hr, and then at room temperature for 1.5 hr. The reaction product was then purified by column chromatography on Cosmosil 40C$_{18}$-PREP (a 20% aqueous methanol solution) to prepare 5.4 mg of the title compound.

NMR (D$_2$O) δ(HOD=4.80 ppm): 1.23 (3H, d, J=6.9 Hz), 1.32 (3H, d, J=6.0 Hz), 2.9–3.1 (2H, m), 3.3–3.6 (4H, m), 4.2–4.4 (2H, m), 7.82 (1H, s), 7.84 (1H, s), 8.12 (1H, s)

Example 13

Sodium (1S,5R,6S)-2-[7-(2-acetimidoylaminoethyl) thioimidazo[5,1-b]thiazol-2-yl]-6-((1R)-1-hydroxyethyl)-1-methyl-1-carbapen-2-em-3-carboxylate The procedure of Example 12 was repeated, except that 44.0 mg of sodium (1S,5R,6S)-2-[7-(2-aminoethyl) thioimidazo[5,1-b]thiazol-2-yl]-6-((1R)-1-hydroxyethyl)-1-methyl-1-carbapen-2-em-3-carboxylate and 63 mg of ethylacetimidate hydrochloride were used as the starting compounds. Thus, 9.3 mg of the title compound was prepared.

NMR (D$_2$O) δ(HOD=4.80 ppm): 1.25 (3H, d, J=6.9 Hz), 1.33 (3H, d, J=6.1 Hz), 2.18 (3H, s), 2.95–3.05 (2H, m), 3.25–3.35 (2H, m), 3.5–3.6 (2H, m), 4.25–4.35 (2H, m), 7.88 (1H, s), 8.16 (1H, s)

Example 14

Sodium (1S,5R,6S)-2-[7-(2-fluoroethyl)thioimidazo [5,1-b]thiazol-2-yl]-6-((1R)-1-hydroxyethyl)-1-methyl-1-carbapen-2-em-3-carboxylate a) 4-Nitrobenzyl (1S,5R,6S)-2-[7-(2-fluoroethyl) thioimidazo[5,1-b]thiazol-2-yl]-6-((1R)-1-hydroxyethyl)-1-methyl-1-carbapen-2-em-3-carboxylate The procedure of Example 1a) was repeated, except that 181 mg of 4-nitrobenzyl (1R,3R,5R,6S)-6-((1R)-1-hydroxyethyl)-1-methyl-2-oxo-1-carbapenam-3-carboxylate and 232 mg of 7-(2-fluoroethyl)thio-2-(tri-n-butylstannyl)imidazo[5,1-b]thiazole were used as the starting compounds. Thus, 69 mg of 4-nitrobenzyl (1S,5R, 6S)-2-[(7-fluoroethyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.32 (3H, d, J=7.3 Hz), 1.40 (3H, d, J=6.3 Hz), 3.04–3.13 (2H, m), 3.37 (1H, dd, J$_1$=6.6 Hz, J$_2$=2.9 Hz), 3.43–3.52 (1H, m), 4.29–4.36 (1H, m), 4.38 (1H, dd, J$_1$=9.5 Hz, J$_2$=2.7 Hz), 4.50 (1H, t, J=6.8 Hz), 4.62 (1H, t, J=6.8 Hz), 5.28 (1H, d, J=13.6 Hz), 5.53 (1H, d, J=13.6 Hz), 7.68 (2H, d, J=8.8 Hz), 8.02 (1H, s), 8.25 (2H, d, J=8.8 Hz), 8.31 (1H, s)

b) Sodium (1S,5R,6S)-2-[7-(2-fluoroethyl)thioimidazo[5,1-b]thiazol-2-yl]-6-((1R)-1-hydroxyethyl)-1-methyl-1-carbapen-2-em-3-carboxylate The procedure of Example 1c) was repeated, except that 66 mg of 4-nitrobenzyl (1S,5R,6S)-2-[7-(2-fluoroethyl) thioimidazo[5,1-b]thiazol-2-yl]-6-((1R)-1-hydroxyethyl)-1-methyl-1-carbapen-2-em-3-carboxylate was used as the starting compound. Thus, 32 mg of the title compound was prepared.

NMR (D$_2$O) δ(HOD=4.65 ppm): 1.10 (3H, d, J=7.3 Hz), 1.16 (3H, d, J=6.3 Hz), 2.87 (1H, t, J=6.0 Hz), 2.92 (1H, t, J=6.0 Hz), 3.37 (1H, dd, J$_1$=6.1 Hz, J$_2$=2.7 Hz), 3.38–3.47 (1H, m), 4.08–4.18 (2H, m), 4.32 (1H, t, J=6.0 Hz), 4.44 (1H, t, J=6.0 Hz), 7.77 (1H, s), 8.00 (1H, s)

Example 15

Sodium (1S,5R,6S)-6-((1R)-1-hydroxyethyl)-1-methyl-2-[5-methylthio-7-(2-phosphonoxyethyl) thioimidazo[5,1-b]thiazol-2-yl]-1-carbapen-2-em-3-carboxylate a) 4-Nitrobenzyl (1S,5R,6S)-2-[7-(2-azidoethyl)thio-5-methylthioimidazo[5,1-b]thiazol-2-yl]-6-((1R)-1-hydroxyethyl)-1-methyl-1-carbapen-2-em-3-carboxylate The procedure of Example 1a) was repeated, except that 300 mg of 4-nitrobenzyl (1R,3R,5R,6S)-6-((1R)-1-hydroxyethyl)-1-methyl-2-oxo-1-carbapenam-3-carboxylate and 485 mg of 7-(2-azidoethyl)thio-5-methylthio-2-(tri-n-butylstannyl)imidazo[5,1-b]thiazole were used as the starting compounds. Thus, 272 mg of 4-nitrobenzyl (1S,5R,6S)-2-[7-(2-azidoethyl)thio-5-methylthioimidazo-[5,1-b]thiazol-2-yl]-6-((1R)-1-hydroxyethyl)-1-methyl-1-carbapen-2-em-3-carboxylate was prepared.

NMR (CDCl$_3$) δ: 1.33 (3H, d, J=7.4 Hz), 1.40 (3H, d, J=6.3 Hz), 2.61 (3H, s), 2.9–3.0 (2H, m), 3.37 (1H, dd, J$_1$=6.5 Hz, J$_2$=2.9 Hz), 3.45–3.55 (3H, m), 4.3–4.4 (2H, m), 5.29 (1H, d, J=13.7 Hz), 5.55 (1H, d, J=13.7 Hz), 7.68 (2H, d, J=8.9 Hz), 8.14 (1H, s), 8.25 (2H, d, J=8.9 Hz)

b) Sodium (1S,5R,6S)-6-((1R)-1-hydroxyethyl)-1-methyl-2-[5-methylthio-7-(2-phosphonoxyethyl)thioimidazo[5,1-b]thiazol-2-yl]-1-carbapen-2-em-3-carboxylate The procedure of Example 1c) was repeated, except that 136 mg of 4-nitrobenzyl (1S,5R,6S)-2-[7-(2-azidoethyl) thio-5-methylthioimidazo[5,1-b]thiazol-2-yl]-6-((1R)-1-hydroxyethyl)-1-methyl-1-carbapen-2-em-3-carboxylate was used as the starting compound for the reaction. The reaction product was purified by column chromatography on Cosmosil 40C$_{18}$-PREP (a 10 to 25% aqueous methanol solution), and a fraction was collected which had been eluted first. Thus, 5.0 mg of the title compound was prepared.

NMR (D$_2$O) δ(HOD=4.80 ppm): 1.25 (3H, d, J=6.9 Hz), 1.33 (3H, d, J=6.3 Hz), 2.50 (3H, s), 2.9–3.05 (2H, m), 3.5–3.7 (2H, m), 3.8–3.9 (2H, m), 4.2–4.35 (2H, m), 7.86 (1H, s)

Example 16

Sodium (1S,5R,6S)-6-((1R)-1-hydroxyethyl)-2-[7-(2-hydroxyethyl)thio-5-methylthioimidazo[5,1-b] thiazol-2-yl]-1-methyl-1-carbapen-2-em-3-carboxylate A fraction was collected which had been eluted second in the column chromatography on Cosmosil 40C$_{18}$-PREP (a 10 to 25% aqueous methanol solution) in Example 15b). Thus, 6.8 mg of the title compound was prepared.

NMR (D$_2$O) δ(HOD=4.80 ppm): 1.23 (3H, d, J=7.1 Hz), 1.33 (3H, d, J=6.3 Hz), 2.49 (3H, s), 2.8–2.9 (2H, m), 3.49 (1H, dd, J$_1$=6.3 Hz, J$_2$=2.7 Hz), 3.5–3.65 (3H, m), 4.2–4.35 (2H, m), 7.77 (1H, s)

Example 17

Sodium (1S,5R,6S)-2-[7-(2-aminoethyl)thio-5-methylimidazo[5,1-b]thiazol-2-yl]-6-((1R)-1-hydroxyethyl)-1-methyl-1-carbapen-2-em-3-carboxylate A main product was collected which had been eluted lastly in the column chromatograph on Cosmosil 40C$_{18}$-PREP (a 10 to 25% aqueous methanol solution) in Example 15b). Thus, 52.9 mg of the title compound was prepared.

NMR (D$_2$O) δ(HOD=4.80 ppm): 1.23 (3H, d, J=7.1 Hz), 1.32 (3H, d, J=6.3 Hz), 2.50 (3H, s), 2.9–3.0 (2H, m), 3.05–3.15 (2H, m), 3.50 (1H, dd, J$_1$=6.2 Hz, J$_2$=2.7 Hz), 3.5–3.65 (1H, m), 4.25–4.35 (2H, m), 7.77 (1H, s)

Example 18

Sodium (1S,5R,6S)-2-[7-(2-formylaminoethyl) thioimidazo[5,1-b]thiazol-2-yl]-6-((1R)-1-hydroxyethyl-1-methyl-1-carbapen-2-em-3-carboxylate a) 4-Nitrobenzyl (1S,5R,6S)-2-[7-(2-formylaminoethyl) thioimidazo[5,1-b]thiazol-2-yl]-6-((1R)-1-hydroxyethyl)-1-methyl-1-carbapen-2-em-3-carboxylate The procedure of Example 1a) was repeated, except that 1.06 g of 4-nitrobenzyl (1R,3R,5R,6S)-6-((1R)-1-hydroxyethyl)-1-methyl-2-oxo-1-carbapenam-3-carboxylate and 1.665 g of 7-(2-formylaminoethyl)thio-2-(tri-n-butylstannyl)imidazo[5,1-b]thiazole were used as the starting compounds. Thus, 818 mg of 4-nitrobenzyl (1S,5R,6S)-2-[7-(2-formylaminoethyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.32 (3H, d, J=7.4 Hz), 1.40 (3H, d, J=6.3 Hz), 2.85–2.95 (2H, m), 3.38 (1H, dd, J$_1$=6.6 Hz, J$_2$=2.8 Hz), 3.4–3.6 (3H, m), 4.25–4.35 (1H, m), 4.39 (1H, dd, J$_1$=9.6 Hz, J$_2$=2.8 Hz), 5.28 (1H, d, J=13.5 Hz), 5.53 (1H, d, J=13.5 Hz), 7.1–7.2 (1H, br s), 7.68 (2H, d, J=8.9 Hz), 8.03 (1H, s), 8.21 (1H, s), 8.25 (2H, d, J=8.9 Hz), 8.30 (1H, s)

b) Sodium (1S,5R,6S)-2-[7-(2-formylaminoethyl)thioimidazo[5,1-b]thiazol-2-yl]-6-((1R)-1-hydroxyethyl)-1-methyl-1-carbapen-2-em-3-carboxylate The procedure of Example 1c) was repeated, except that 165 mg of 4-nitrobenzyl (1S,5R,6S)-2-[7-(2-formylaminoethyl)thioimidazo[5,1-b]thiazol-2-yl]-6-((1R)-1-hydroxyethyl)-1-methyl-1-carbapen-2-em-3-carboxylate was used as the starting compound. Thus, 90.7 mg of the title compound was prepared.

NMR (D$_2$O) δ(HOD=4.80 ppm): 1.23 (3H, d, J=7.1 Hz), 1.33 (3H, d, J=6.3 Hz), 2.85–2.95 (2H, m), 3.25–3.4 (2H, m), 3.45–3.6 (2H, m), 4.2–4.35 (2H, m), 7.85 (1H, s), 8.01 (1H, s), 8.10 (1H, s)

Example 19

Sodium (1S,5R,6S)-2-[7-(3-aminopropyl)thioimidazo[5,1-b]thiazol-2-yl]-6-((1R)-1-hydroxyethyl)-1-methyl-1-carbapen-2-em-3-carboxylate a) 4-Nitrobenzyl (1S,5R,6S)-6-((1R)-1-hydroxyethyl)-1-methyl-2-[7-[3-(4-nitrobenzyloxycarbonyl)aminopropyl]thioimidazo[5,1-b]thiazol-2-yl]-1-carbapen-2-em-3-carboxylate The procedure of Example 1a) was repeated, except that 628 mg of 4-nitrobenzyl (1R,3R,5R,6S)-6-((1R)-1-hydroxyethyl)-1-methyl-2-oxo-1-carbapenam-3-carboxylate and 1.24 g of 7-[3-(4-nitrobenzyloxycarbonyl)aminopropyl]thio-2-(tri-n-butylstannyl)imidazo[5,1-b]-thiazole were used as the starting compounds. Thus, 812 mg of 4-nitrobenzyl (1S,5R,6S)-6-((1R)-1-hydroxyethyl)-1-methyl-2-[7-[3-(4-nitrobenzyloxycarbonyl)aminopropyl]thioimidazo[5,1-b]thiazol-2-yl]-1-carbapen-2-em-3-carboxylate were prepared.

NMR (CDCl$_3$) δ: 1.31 (3H, d, J=7.4 Hz), 1.40 (3H, d, J=6.2 Hz), 1.8–1.9 (2H, m), 2.8–2.95 (2H, m), 3.35–3.5 (4H, m), 4.3–4.4 (2H, m), 5.18 (2H, s), 5.27 (1H, d, J=13.5 Hz), 5.42 (1H, br s), 5.52 (1H, d, J=13.5 Hz), 7.50 (2H, d, J=8.8 Hz), 7.68 (2H, d, J=8.8 Hz), 8.02 (1H, s), 8.20 (2H, d, J=8.8 Hz), 8.24 (2H, d, J=8.8 Hz), 8.28 (1H, s)

b) Sodium (1S,5R,6S)-2-[7-(3-aminopropyl)thioimidazo[5,1-b]thiazol-2-yl]-6-((1R)-1-hydroxyethyl)-1-methyl-1-carbapen-2-em-3-carboxylate The procedure of Example 1c) was repeated, except that 167 mg of 4-nitrobenzyl (1S,5R,6S)-6-((1R)-1-hydroxyethyl)-1-methyl-2-[7-[3-(4-nitrobenzyloxycarbonyl)aminopropyl]thioimidazo[5,1-b]thiazol-2-yl]-1-carbapen-2-em-3-carboxylate was used as the starting compound. Thus, 48.4 mg of the title compound was prepared.

NMR (D$_2$O) δ(HOD=4.80 ppm): 1.22 (3H, d, J=7.3 Hz), 1.33 (3H, d, J=6.4 Hz), 1.75–1.95 (2H, m), 2.75–2.85 (2H, m), 3.05–3.15 (2H, m), 3.45–3.6 (2H, m), 4.25–4.35 (2H, m), 7.80 (1H, s), 8.07 (1H, s)

Example 20

Sodium (1S,5R,6S)-2-[7-(2-guanidinoethyl)thioimidazo[5,1-b]thiazol-2-yl]-6-((1R)-1-hydroxyethyl)-1-methyl-1-carbapen-2-em-3-carboxylate a) 4-Nitrobenzyl (1S,5R,6S)-2-[7-[2-N,N'-bis(4-nitrobenzyloxycarbonyl)guanidinoethyl]thioimidazo-[5,1-b]-thiazol-2-yl]-6-((1R)-1-hydroxyethyl)-1-methyl-1-carbapen-2-em-3-carboxylate The procedure of Example 1a) was repeated, except that 101 mg of 4-nitrobenzyl (1R,3R,5R,6S)-6-((1R)-1-hydroxyethyl)-1-methyl-2-oxo-1-carbapenam-3-carboxylate and 260 mg of 7-[2-N,N'-bis(4-nitrobenzyloxycarbonyl)guanidinoethyl]thio-2-(tri-n-butylstannyl)imidazo[5,1-b]thiazole were used as the starting compounds. Thus, 85.6 mg of 4-nitrobenzyl (1S,5R,6S)-2-[7-[2-N,N'-bis(4-nitrobenzyloxycarbonyl)guanidinoethyl]thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.30 (3H, d, J=7.2 Hz), 1.41 (3H, d, J=6.0 Hz), 2.9–3.05 (2H, m), 3.35–3.5 (2H, m), 3.6–3.7 (2H, m), 4.25–4.4 (2H, m), 5.20 (2H, s), 5.26 (1H, d, J=13.5 Hz), 5.31 (2H, s), 5.51 (1H, d, J=13.5 Hz), 7.5–7.6 (4H, m), 7.67 (2H, d, J=8.7 Hz), 8.01 (1H, s), 8.15–8.3 (6H, m), 8.8–8.9 (1H, m), 11.8 (1H, s)

b) Sodium (1S,5R,6S)-2-[7-(2-guanidinoethyl)thioimidazo [5,1-b]thiazol-2-yl]-6-((1R)-1-hydroxyethyl)-1-methyl-1-carbapen-2-em-3-carboxylate The procedure of Example 1c) was repeated, except that 47.9 mg of 4-nitrobenzyl (1S,5R,6S)-2-[7-[2-N,N'-bis(4-nitrobenzyloxycarbonyl)guanidinoethyl]thioimidazo-[5,1-b]thiazol-2-yl]-6-((1R)-1-hydroxyethyl)-1-methyl-1-carbapen-2-em-3-carboxylate was used as the starting compound. Thus, 12.7 mg of the title compound was prepared.

NMR (D$_2$O) δ(HOD=4.80 ppm): 1.24 (3H, d, J=7.2 Hz), 1.32 (3H, d, J=6.3 Hz), 2.9–3.0 (2H, m), 3.2–3.3 (2H, m), 3.45–3.6 (2H, m), 4.2–4.35 (2H, m), 7.86 (1H, s), 8.13 (1H, s)

Example 21

Sodium (1S,5R,6S)-2-[7-(3-acetimidoylaminopropyl)thioimidazo[5,1-b]thiazol-2-yl]-6-((1R)-1-hydroxyethyl)-1-methyl-1-carbapen-2-em-3-carboxylate The procedure of Example 12 was repeated, except that 29.1 mg of sodium (1S,5R,6S)-2-[7-(3-aminopropyl)thioimidazo[5,1-b]thiazol-2-yl]-6-((1R)-1-hydroxyethyl)-1-methyl-1-carbapen-2-em-3-carboxylate and 40 mg of ethylacetimidate hydrochloride were used as the starting compounds. Thus, 8.8 mg of the title compound was prepared.

NMR (D$_2$O) δ(HOD=4.80 ppm): 1.24 (3H, d, J=7.2 Hz), 1.32 (3H, d, J=6.6 Hz), 1.8–1.9 (2H, m), 2.12 (3H, s), 2.75–2.85 (2H, m), 3.3–3.4 (2H, m), 3.45–3.6 (2H, m), 4.25–4.35 (2H, m), 7.86 (1H, s), 8.10 (1H, s)

Example 22

(1S,5R,6S)-2-[7-(6-Aminohexyl)thioimidazo[5,1-b]thiazol-2-yl]-6-((1R)-1-hydroxyethyl)-1-methyl-1-carbapen-2-em-3-carboxylic acid a) 4-Nitrobenzyl (1S,5R,6S)-2-[7-(6-azidohexyl)thioimidazo[5,1-b]thiazol-2-yl]-6-((1R)-1-hydroxyethyl)-1-methyl-1-carbapen-2-em-3-carboxylate The procedure of Example 1a) was repeated, except that 611 mg of 4-nitrobenzyl (1R,3R,5R,6S)-6-((1R)-1-hydroxyethyl)-1-methyl-2-oxo-1-carbapenam-3-carboxylate and 1.01 g of 7-(6-azidohexyl)thio-2-(tri-n-butylstannyl)imidazo[5,1-b]thiazole were used as the starting compounds. Thus, 493 mg of 4-nitrobenzyl (1S,5R,6S)-2-[7-(6-azidohexyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.2–1.5 (10H, m), 1.5–1.7 (4H, m), 2.75–2.85 (2H, m), 3.2–3.3 (2H, m), 3.37 (1H, dd, J$_1$=6.6 Hz, J$_2$=2.4 Hz), 3.4–3.55 (1H, m), 4.25–4.35 (1H, m), 4.38 (1H, dd, J$_1$=9.6 Hz, J$_2$=2.4 Hz), 5.27 (1H, d, J=13.5 Hz), 5.53 (1H, d, J=13.5 Hz), 7.68 (2H, d, J=8.7 Hz), 8.02 (1H, s), 8.24 (2H, d, J=8.7 Hz), 8.30 (1H, s)

b) (1S,5R,6S)-2-[7-(6-Aminohexyl)thioimidazo[5,1-b]thiazol-2-yl]-6-((1R)-1-hydroxyethyl)-1-methyl-1-carbapen-2-em-3-carboxylic acid The procedure of Example 1c) was repeated, except that 268 mg of 4-nitrobenzyl (1S,5R,6S)-2-[7-(6-azidohexyl)thioimidazo[5,1-b]thiazol-2-yl]-6-((1R)-1-hydroxyethyl)-1-methyl-1-carbapen-2-em-3-carboxylate was used as the starting compound. Thus, 62.3 mg of the title compound was prepared.

NMR (D$_2$O) δ(HOD=4.80 ppm): 1.2–1.6 (12H, m), 1.6–1.7 (2H, m), 2.7–2.8 (2H, m), 2.95–3.0 (2H, m), 3.50 (1H, dd, J$_1$=6.3 Hz, J$_2$=2.4 Hz), 3.5–3.6 (1H, m), 4.25–4.35 (2H, m), 7.88 (1H, s), 8.12 (1H, s)

Example 23

Sodium (1S,5R,6S)-6-((1R)-1-hydroxyethyl)-1-methyl-2-[7-((3S)-pyrrolidin-3-yl)thioimidazo[5,1-b]thiazol-2-yl]-1-carbapen-2-em-3-carboxylate a) 4-Nitrobenzyl (1S,5R,6S)-6-((1R)-1-hydroxyethyl)-1-methyl-2-[7-[(3S)-1-(4-nitrobenzyloxycarbonyl)pyrrolidin-3-yl]thioimidazo[5,1-b]thiazol-2-yl]-1-carbapen-2-em-3-carboxylate The procedure of Example 1a) was repeated, except that 143 mg of 4-nitrobenzyl (1R,3R,5R,6S)-6-((1R)-1-hydroxyethyl)-1-methyl-2-oxo-1-carbapenam-3-carboxylate and 287 mg of 7-[(3S)-1-(4-nitrobenzyloxycarbonyl)pyrrolidin-3-yl]thio-2-(tri-n-butylstannyl)imidazo[5,1-b]thiazole were used as the starting compounds. Thus, 136 mg of 4-nitrobenzyl (1S,5R,6S)-6-((1R)-1-hydroxyethyl)-1-methyl-2-[7-[(3S)-1-(4-nitrobenzyloxycarbonyl)pyrrolidin-3-yl]thioimidazo[5,1-b]thiazol-2-yl]-1-carbapen-2-em-3-carboxylate was prepared.

NMR (CDCl$_3$) δ: 1.29 (3H, d, J=6.6 Hz), 1.40 (3H, d, J=6.3 Hz), 1.9–2.3 (2H, m), 3.35–3.6 (4H, m), 3.6–3.8 (3H, m), 4.25–4.4 (2H, m), 5.21 (2H, s), 5.27 (1H, d, J=13.5 Hz), 5.52 (1H, d, J=13.5 Hz), 7.4–7.55 (2H, m), 7.6–7.7 (2H, m), 8.03, 8.04 (total 1H, s each), 8.1–8.3 (5H, m)

b) Sodium (1S,5R,6S)-6-((1R)-1-hydroxyethyl)-1-methyl-2-[7-((3S)-pyrrolidin-3-yl)thioimidazo[5,1-b]thiazol-2-yl]-1-carbapen-2-em-3-carboxylate The procedure of Example 1c) was repeated, except that 75.5 mg of 4-nitrobenzyl (1S,5R,6S)-6-((1R)-1-hydroxyethyl)-1-methyl-2-[7-[(3S)-1-(4-nitrobenzyloxycarbonyl)pyrrolidin-3-yl]thioimidazo[5,1-b]thiazol-2-yl]-1-carbapen-2-em-3-carboxylate was used as the starting compound. Thus, 16.1 mg of the title compound was prepared.

NMR (D$_2$O) δ(HOD=4.80 ppm): 1.22 (3H, d, J=7.5 Hz), 1.32 (3H, d, J=6.3 Hz), 1.9–2.05 (1H, m), 2.25–2.4 (1H, m), 3.2–3.6 (6H, m), 3.7–3.85 (1H, m), 4.2–4.35 (2H, m), 7.83 (1H, s), 8.11 (1H, s)

Example 24

Sodium (1S,5R,6S)-6-((1R)-1-hydroxyethyl)-1-methyl-2-(7-trifluoromethylthioimidazo[5,1-b]thiazol-2-yl)-1-carbapen-2-em-3-carboxylate a) 4-Nitrobenzyl (1S,5R,6S)-6-((1R)-1-hydroxyethyl)-1-methyl-2-(7-trifluoromethylthioimidazo[5,1-b]thiazol-2-yl)-1-carbapen-2-em-3-carboxylate The procedure of Example 1a) was repeated, except that 743 mg of 4-nitrobenzyl (1R,3R,5R,6S)-6-((1R)-1-hydroxyethyl)-1-methyl-2-oxo-1-carbapenam-3-carboxylate and 1.06 g 2-(tri-n-butylstannyl)-7-trifluoromethylthioimidazo[5,1-b]thiazole were used as the starting compounds. Thus, 172 mg of 4-nitrobenzyl (1S,5R,6S)-6-((1R)-1-hydroxyethyl)-1-methyl-2-(7-trifluoromethylthioimidazo[5,1-b]thiazol-2-yl)-1-carbapen-2-em-3-carboxylate was prepared.

NMR (CDCl$_3$) δ: 1.32 (3H, d, J=7.3 Hz), 1.40 (3H, d, J=6.3 Hz), 3.36–3.41 (1H, m), 3.45–3.54 (1H, m), 4.28–4.42 (2H, m), 5.28 (1H, d, J=13.0 Hz), 5.53 (1H, d, J=13.0 Hz), 7.67 (2H, d, J=8.8 Hz), 8.09 (1H, s), 8.24 (2H, d, J=8.8 Hz), 8.33 (1H, s)

b) Sodium (1S,5R,6S)-6-((1R)-1-hydroxyethyl)-1-methyl-2-(7-trifluoromethylthioimidazo[5,1-b]thiazol-2-yl)-1-carbapen-2-em-3-carboxylate The procedure of Example 1c) was repeated, except that 60 mg of 4-nitrobenzyl (1S,5R,6S)-6-((1R)-1-hydroxyethyl)-1-methyl-2-(7-trifluoromethylthioimidazo[5,1-b]thiazol-2-yl)-1-carbapen-2-em-3-carboxylate was used as the starting compound. Thus, 28 mg of the title compound was prepared.

NMR (D$_2$O) δ(HOD=4.65 ppm): 1.08 (3H, d, J=7.3 Hz), 1.16 (3H, d, J=6.3 Hz), 3.36 (1H, dd, J$_1$=6.0 Hz, J$_2$=2.7 Hz), 3.38–3.47 (1H, m), 4.08–4.18 (2H, m), 7.79 (1H, s), 8.06 (1H, s)

Example 25

(1S,5R,6S)-2-(7-carbamoylmethylthioimidazo[5,1-b]thiazol-2-yl)-6-((1R)-1-hydroxyethyl)-1-methyl-1-carbapen-2-em-3-carboxylic acid a) 4-Nitrobenzyl (1S,5R,6S)-2-(7-carbamoylmethylthioimidazo[5,1-b]thiazol-2-yl)-6-((1R)-1-hydroxyethyl)-1-methyl-1-carbapen-2-em-3-carboxylate The procedure of Example 1a) was repeated, except that 231 mg of 4-nitrobenzyl (1R,3R,5R,6S)-6-((1R)-1-hydroxyethyl)-1-methyl-2-oxo-1-carbapenam-3-carboxylate and 336 mg of 7-carbamoylmethylthio-2-(tri-n-butylstannyl)imidazo[5,1-b]thiazole were used as the starting compounds. Thus, 213 mg of 4-nitrobenzyl (1S,5R,6S)-2-(7-carbamoylmethylthioimidazo[5,1-b]thiazol-2-yl)-6-((1R)-1-hydroxyethyl)-1-methyl-1-carbapen-2-em-3-carboxylate was prepared.

NMR (DMSO-d$_6$) δ: 1.15–1.25 (6H, m), 3.31 (2H, s), 3.35–3.45 (1H, m), 3.6–3.75 (1H, m), 3.95–4.1 (1H, m), 4.32 (1H, dd, J$_1$=9.6 Hz, J$_2$=2.7 Hz), 5.15 (1H, d, J=5.1 Hz), 5.39 (1H, d, J=13.8 Hz), 5.52 (1H, d, J=13.8 Hz), 7.04 (1H, br s), 7.46 (1H, br s), 7.74 (2H, d, J=8.7 Hz), 8.23 (2H, d, J=8.7 Hz), 8.26 (1H, s), 8.42 (1H, s)

b) (1S,5R,6S)-2-(7-Carbamoylmethylthioimidazo[5,1-b]thiazol-2-yl)-6-((1R)-1-hydroxyethyl)-1-methyl-1-carbapen-2-em-3-carboxylic acid The procedure of Example 1c) was repeated, except that 97.9 mg of 4-nitrobenzyl (1S,5R,6S)-2-(7-carbamoylmethylthioimidazo[5,1-b]thiazol-2-yl)-6-((1R)-1-hydroxyethyl)-1-methyl-1-carbapen-2-em-3-carboxylate was used as the starting compound. Thus, 34.9 mg of the title compound was prepared.

NMR (D$_2$O) δ(HOD=4.80 ppm): 1.23 (3H, d, J=6.9 Hz), 1.32 (3H, d, J=6.6 Hz), 3.38 (2H, s), 3.45–3.6 (2H, m), 4.2–4.35 (2H, m), 7.84 (1H, s), 8.13 (1H, s)

Example 26

(1S,5R,6S)-2-[7-(2-Aminosulfonylaminoethyl)thioimidazo[5,1-b]thiazol-2-yl]-6-((1R)-1-hydroxyethyl)-1-methyl-1-carbapen-2-em-3-carboxylic acid a) 4-Nitrobenzyl (1S,5R,6S)-6-((1R)-1-hydroxyethyl)-1-methyl-2-[7-[2-(4-nitrobenzyloxycarbonyl)aminosulfonylaminoethyl]thioimidazo[5,1-b]thiazol-2-yl]-1-carbapen-2-em-3-carboxylate The procedure of Example 1a) was repeated, except that 54 mg of 4-nitrobenzyl (1R,3R,5R,6S)-6-((1R)-1-hydroxyethyl)-1-methyl-2-oxo-1-carbapenam-3-carboxylate and 116 mg of 7-[2-(4-nitrobenzyloxycarbonyl)aminosulfonylaminoethyl]thio-2-(tri-n-butylstannyl)imidazo[5,1-b]thiazole were used as the starting compounds. Thus, 31.8 mg of 4-nitrobenzyl (1S,5R,6S)-6-((1R)-1-hydroxyethyl)-1-methyl-2-[7-[2-(4-nitrobenzyloxycarbonyl)aminosulfonylaminoethyl]thioimidazo[5,1-b]thiazol-2-yl]-1-carbapen-2-em-3-carboxylate was prepared.

NMR (CDCl$_3$) δ: 1.31 (3H, d, J=7.2 Hz), 1.40 (3H, d, J=6.3 Hz), 2.85–2.95 (2H, m), 3.35–3.5 (4H, m), 4.25–4.4 (2H, m), 5.28 (1H, d, J=13.5H), 5.53 (1H, d, J=13.5H), 7.51 (2H, d, J=8.7 Hz), 7.68 (2H, d, J=8.7 Hz), 8.00 (1H, s), 8.15–8.3 (5H, m)

b) (1S,5R,6S)-2-[7-(2-Aminosulfonylaminoethyl)thioimidazo[5,1-b]thiazol-2-yl]-6-((1R)-1-hydroxyethyl)-1-methyl-1-carbapen-2-em-3-carboxylic acid The procedure of Example 1c) was repeated, except that 31.8 mg of 4-nitrobenzyl (1S,5R,6S)-6-((1R)-1-hydroxyethyl)-1-methyl-2-[7-[2-(4-nitrobenzyloxycarbonyl)aminosulfonylaminoethyl]thioimidazo[5,1-b]thiazol-2-yl]-1-carbapen-2-em-3-carboxylate was used as the starting compound. Thus, 4.1 mg of the title compound was prepared.

NMR (D$_2$O) δ(HOD=4.80 ppm): 1.26 (3H, d, J=7.2 Hz), 1.32 (3H, d, J=6.6 Hz), 2.95–3.05 (2H, m), 3.15–3.25 (2H, m), 3.5–3.65 (2H, m), 4.2–4.35 (2H, m), 8.01 (1H, s), 8.54 (1H, s)

Example 27

Sodium (1S,5R,6S)-6-((1R)-1-hydroxyethyl)-1-methyl-2-[7-(piperidin-4-yl)thioimidazo[5,1-b]thiazol-2-yl]-1-carbapen-2-em-3-carboxylate a) 4-Nitrobenzyl (1S,5R,6S)-6-((1R)-1-hydroxyethyl)-1-methyl-2-[7-[1-(4-nitrobenzyloxycarbonyl)piperidin-4-yl]thioimidazo[5,1-b]thiazol-2-yl]-1-carbapen-2-em-3-carboxylate The procedure of Example 1a) was repeated, except that 410 mg of 4-nitrobenzyl (1R,3R,5R,6S)-6-((1R)-1-hydroxyethyl)-1-methyl-2-oxo-1-carbapenam-3-carboxylate and 881 mg of 7-[1-(4-nitrobenzyloxycarbonyl)piperidin-4-yl]thio-2-(tri-n-butylstannyl)imidazo[5,1-b]thiazole were used as the starting compounds. Thus, 450 mg of 4-nitrobenzyl (1S,5R,6S)-6-((1R)-1-hydroxyethyl)-1-methyl-2-[7-[1-(4-nitrobenzyloxycarbonyl)piperidin-4-yl]thioimidazo[5,1-b]thiazol-2-yl]-1-carbapen-2-em-3-carboxylate was prepared.

NMR (CDCl$_3$) δ: 1.31 (3H, d, J=7.5 Hz), 1.40 (3H, d, J=6.3 Hz), 1.5–1.7 (2H, m), 1.9–2.1 (2H, m), 2.9–3.2 (3H, m), 3.35–3.5 (2H, m), 4.0–4.15 (2H, m), 4.25–4.4 (2H, m), 5.19 (2H, s), 5.27 (1H, d, J=13.5 Hz), 5.53 (1H, d, J=13.5 Hz), 7.48 (2H, d, J=8.7 Hz), 7.68 (2H, d, J=8.7 Hz), 8.21 (2H, d, J=8.7 Hz), 8.24 (2H, d, J=8.7 Hz), 8.28 (1H, s)

b) Sodium (1S,5R,6S)-6-((1R)-1-hydroxyethyl)-1-methyl-2-[7-(piperidin-4-yl)thioimidazo[5,1-b]thiazol-2-yl]-1-carbapen-2-em-3-carboxylate The procedure of Example 1c) was repeated, except that 197 mg of 4-nitrobenzyl (1S,5R,6S)-6-((1R)-1-hydroxyethyl)-1-methyl-2-[7-[1-(4-nitrobenzyloxycarbonyl)piperidin-4-yl]thioimidazo[5,1-b]thiazol-2-yl]-1-carbapen-2-em-3-carboxylate was used as the starting compound. Thus, 35.7 mg of the title compound was prepared.

NMR (D$_2$O) δ(HOD=4.80 ppm): 1.21 (3H, d, J=7.2 Hz), 1.31 (3H, d, J=6.3 Hz), 1.6–1.8 (2H, m), 2.05–2.2 (2H, m), 2.95–3.1 (2H, m), 3.1–3.25 (1H, m), 3.35–3.6 (4H, m), 4.2–4.35 (2H, m), 7.83 (1H, s), 8.09 (1H, s)

Example 28

Sodium (1S,5R,6S)-2-[7-(2-N,N-dimethylaminosulfonylaminoethyl)thioimidazo[5,1-b]thiazol-2-yl]-6-((1R)-1-hydroxyethyl)-1-methyl-1-carbapen-2-em-3-carboxylate a) 4-Nitrobenzyl (1S,5R,6S)-2-[7-(2-N,N-dimethylaminosulfonylaminoethyl)thioimidazo[5,1-b]thiazol-2-yl]-6-((1R)-1-hydroxyethyl)-1-methyl-1-carbapen-2-em-3-carboxylate The procedure of Example 1a) was repeated, except that 237 mg of 4-nitrobenzyl (1R,3R,5R,6S)-6-((1R)-1-hydroxyethyl)-1-methyl-2-oxo-1-carbapenam-3-carboxylate and 408 mg of 7-(2-N,N-dimethylaminosulfonylaminoethyl)thio-2-(tri-n-butylstannyl)imidazo[5,1-b]thiazole were used as the starting compounds. Thus, 239 mg of 4-nitrobenzyl (1S,5R,6S)-2-[7-(2-N,N-dimethylaminosulfonylaminoethyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.31 (3H, d, J=7.2 Hz), 1.40 (3H, d, J=6.3 Hz), 2.81 (6H, s), 2.9–3.0 (2H, m), 3.3–3.4 (3H, m), 3.4–3.5 (1H, m), 4.3–4.4 (2H, m), 5.28 (1H, d, J=13.5 Hz), 5.52 (1H, d, J=13.5 Hz), 6.1–6.2 (1H, m), 7.68 (2H, d, J=8.7 Hz), 8.03 (1H, s), 8.25 (2H, d, J=8.7 Hz), 8.28 (1H, s)

b) Sodium (1S,5R,6S)-2-[7-(2-N,N-dimethylaminosulfonylaminoethyl)thioimidazo[5,1-b]thiazol-2-yl]-6-((1R)-1-hydroxyethyl)-1-methyl-1-carbapen-2-em-3-carboxylate The procedure of Example 1c) was repeated, except that 85.1 mg of 4-nitrobenzyl (1S,5R,6S)-2-[7-(2-N,N-dimethylaminosulfonylaminoethyl)thioimidazo[5,1-b]thiazol-2-yl]-6-((1R)-1-hydroxyethyl)-1-methyl-1-carbapen-2-em-3-carboxylate was used as the starting compound. Thus, 30.6 mg of the title compound was prepared.

NMR (D$_2$O) δ(HOD=4.80 ppm): 1.23 (3H, d, J=6.9 Hz), 1.31 (3H, d, J=6.3 Hz), 2.67 (6H, s), 2.8–2.9 (2H, m), 3.1–3.2 (2H, m), 3.45–3.6 (2H, m), 4.2–4.35 (2H, m), 7.88 (1H, s), 8.11 (1H, s)

Example 29

(1S,5R,6S)-2-[7-[2-(1-Azonia-4-azabicyclo[2,2,2]oct-1-yl)ethyl]thioimidazo[5,1-b]thiazol-2-yl]-6-((1R)-1-hydroxyethyl)-1-methyl-1-carbapen-2-em-3-carboxylate (intramolecular salt) hydrochloride a) 4-Nitrobenzyl (1S,5R,6S)-2-[7-(2-bromoethyl)thioimidazo[5,1-b]thiazol-2-yl]-6-((1R)-1-hydroxyethyl)-1-methyl-1-carbapen-2-em-3-carboxylate The procedure of Example 1a) was repeated, except that 1.01 g of 4-nitrobenzyl (1R,3R,5R,6S)-6-((1R)-1- hydroxyethyl)-1-methyl-2-oxo-1-carbapenam-3-carboxylate and 1.62 g of 7-(2-bromoethyl)thio-2-(tri-n-butylstannyl)imidazo[5,1-b]thiazole were used as the starting compounds. Thus, 780 mg of 4-nitrobenzyl (1S,5R,6S)-2-[7-(2-bromoethyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.32 (3H, d, J=7.2 Hz), 1.40 (3H, d, J=6.3 Hz), 3.1–3.2 (2H, m), 3.38 (1H, dd, J$_1$=6.6 Hz, J$_2$=3.0 Hz), 3.4–3.6 (3H, m), 4.25–4.35 (1H, m), 4.38 (1H, dd, J$_1$=9.3 Hz, J$_2$=3.0 Hz), 5.28 (1H, d, J=13.5 Hz), 5.53 (1H, d, J=13.5 Hz), 7.68 (2H, d, J=8.7 Hz), 8.03 (1H, s), 8.25 (2H, d, J=8.7 Hz), 8.30 (1H, s)

b) 4-Nitrobenzyl (1S,5R,6S)-2-[7-[2-(1-azonia-4-azabicyclo[2,2,2]oct-1-yl)ethyl]thioimidazo[5,1-b]thiazol-2-yl)-6-((1R)-1-hydroxyethyl)-1-methyl-1-carbapen-2-em-3-carboxylate bromide 4-Nitrobenzyl (1S,5R,6S)-2-[7-(2-bromoethyl)thioimidazo[5,1-b]thiazol-2-yl]-6-((1R)-1-hydroxyethyl)-1-methyl-1-carbapen-2-em-3-carboxylate (177 mg) was dissolved in 5 ml of acetonitrile. 1,4-Diazabicylco[2,2,2]octane (43 mg) was added to the solution. The mixture was stirred at 50° C. for 12 hr. The reaction solution was concentrated, and the residue was purified by column chromatography on Sephadex LH-20 (chloroform:methanol=1:1) to prepare 184 mg of 4-nitrobenzyl (1S,5R,6S)-2-[7-[2-(1-azonia-4-azabicyclo-[2,2,2]oct-1-yl)ethyl]thioimidazo[5,1-b]thiazol-2-yl]-6-((1R)-1-hydroxyethyl)-1-methyl-1-carbapen-2-em-3-carboxylate bromide.

NMR (CD$_3$OD) δ: 1.25–1.35 (6H, m), 3.1–3.2 (8H, m), 3.25–3.4 (6H, m), 3.4–3.5 (3H, m), 3.6–3.7 (1H, m), 4.1–4.2 (1H, m), 4.36 (1H, dd, J$_1$=9.6 Hz, J$_2$=2.7 Hz), 5.35 (1H, d, J=13.2 Hz), 5.52 (1H, d, J=13.2 Hz), 7.73 (2H, d, J=8.7 Hz), 8.22 (2H, d, J=8.7 Hz), 8.27 (1H, s), 8.35 (1H, s)

c) (1S,5R,6S)-2-[7-[2-(1-Azonia-4-azabicyclo-[2,2,2]oct-1-yl)ethyl]thioimidazo[5,1-b]thiazol-2-yl]-6-((1R)-1-hydroxyethyl)-1-methyl-1-carbapen-2-em-3-carboxylate (intramolecular salt) hydrochloride The procedure of Example 1c) was repeated, except that 122 mg of 4-nitrobenzyl (1S,5R,6S)-2-[7-[2-(1-azonia-4-azabicyclo[2,2,2]oct-1-yl)ethyl]thioimidazo[5,1-b]thiazol-2-yl]-6-((1R)-1-hydroxyethyl)-1-methyl-1-carbapen-2-em-3-carboxylate bromide was used as the starting compound for the reaction. The reaction product was subjected to column chromatography on Amberlyst A-26 as an ion-exchange resin (chloro form) (water). Thus, 52.1 mg of the title compound was prepared.

NMR (D$_2$O) δ(HOD=4.80 ppm): 1.25 (3H, d, J=7.2 Hz), 1.34 (3H, d, J=6.3 Hz), 3.05–3.2 (8H, m), 3.3–3.5 (8H, m), 3.5–3.6 (2H, m), 4.25–4.35 (2H, m), 7.85 (1H, s), 8.14 (1H, s)

Example 30

(1S,5R,6S)-2-[7-(3-Guanidinopropyl)thioimidazo[5,1-b]thiazol-2-yl]-6-((1R)-1-hydroxyethyl)-1-methyl-1-carbapen-2-em-3-carboxylic acid a) 4-Nitrobenzyl (1S,5R,6S)-2-[7-[3-N,N'-bis(4-nitrobenzyloxycarbonyl)guanidinopropyl]thioimidazo[5,1-b]thiazol-2-yl]-6-((1R)-1-hydroxyethyl)-1-methyl-1-carbapen-2-em-3-carboxylate The procedure of Example 1a) was repeated, except that 297 mg of 4-nitrobenzyl (1R,3R,5R,6S)-6-((1R)-1-hydroxyethyl)-1-methyl-2-oxo-1-carbapenam-3-carboxylate and 777 mg of 7-[3-N,N'-bis(4-nitrobenzyloxycarbonyl)guanidinopropyl]thio-2-(tri-n-butylstannyl)imidazo[5,1-b]thiazole were used as the starting compounds. Thus, 436 mg of 4-nitrobenzyl (1S,5R,6S)-2-[7-[3-N,N'-bis(4-nitrobenzyloxycarbonyl)guanidinopropyl]thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 1.30 (3H, d, J=7.2 Hz), 1.40 (3H, d, J=6.3 Hz), 1.85–1.95 (2H, m), 2.8–2.9 (2H, m), 3.36 (1H, dd, J$_1$=6.3 Hz, J$_2$=2.7 Hz), 3.4–3.5 (1H, m), 3.6–3.7 (2H, m), 4.25–4.4 (2H, m), 5.22 (2H, s), 5.26 (2H, s), 5.27 (1H, d, J=13.8 Hz), 5.52 (1H, d, J=13.8 Hz), 7.5–7.6 (4H, m), 7.68 (2H, d, J=8.4 Hz), 8.01 (1H, s), 8.15–8.3 (7H, m), 8.4–8.5 (1H, m), 11.78 (1H, s)

b) (1S,5R,6S)-2-[7-(3-Guanidinopropyl)thioimidazo[5,1-b]thiazol-2-yl]-6-((1R)-1-hydroxyethyl)-1-methyl-1-carbapen-2-em-3-carboxylic acid The procedure of Example 1c) was repeated, except that 121.6 mg of 4-nitrobenzyl (1S,5R,6S)-2-[7-[3-N,N'-bis(4-nitrobenzyloxycarbonyl)guanidinopropyl]thioimidazo[5,1-b]thiazol-2-yl]-6-((1R)-1-hydroxyethyl)-1-methyl-1-carbapen-2-em-3-carboxylate was used as the starting compound. Thus, 39.9 mg of the title compound was prepared.

NMR (D$_2$O) δ(HOD=4.80 ppm): 1.26 (3H, d, J=7.2 Hz), 1.33 (3H, d, J=6.3 Hz), 1.75–1.85 (2H, m), 2.8–2.9 (2H, m), 3.2–3.3 (2H, m), 3.5–3.6 (2H, m), 4.25–4.35 (2H, m), 7.89 (1H, s), 8.13 (1H, s)

Example 31

Sodium (1S,5R,6S)-2-[7-(2-bromoethyl)thioimidazo[5,1-b]thiazol-2-yl]-6-((1R)-1-hydroxyethyl)-1-methyl-1-carbapen-2-em-3-carboxylate The procedure of Example 1c) was repeated, except that 78.4 mg of 4-nitrobenzyl (1S,5R,6S)-2-[7-(2-bromoethyl)thioimidazo[5,1-b]thiazol-2-yl]-6-((1R)-1-hydroxyethyl)-1-methyl-1-carbapen-2-em-3-carboxylate was used as the starting compound. Thus, 8.6 mg of the title compound was prepared.

NMR (D$_2$O) δ(HOD=4.80 ppm): 1.19 (3H, d, J=7.2 Hz), 1.29 (3H, d, J=6.6 Hz), 2.8–2.9 (2H, m), 3.4–3.6 (4H, m), 4.2–4.3 (2H, m), 7.79 (1H, s), 8.04 (1H, s)

Example 32

Sodium (1S,5R,6S)-2-(7-benzylthioimidazo[5,1-b]thiazol-2-yl)-6-((1R)-1-hydroxyethyl)-1-methyl-1-carbapen-2-em-3-carboxylate a) 4-Nitrobenzyl (1S,5R,6S)-2-(7-benzylthioimidazo[5,1-b]thiazol-2-yl)-6-((1R)-1-hydroxyethyl)-1-methyl-1-carbapen-2-em-3-carboxylate The procedure of Example 1a) was repeated, except that 424 mg of 4-nitrobenzyl (1R,3R,5R,6S)-6-((1R)-1-hydroxyethyl)-1-methyl-2-oxo-1-carbapenam-3-carboxylate and 658 mg of 7-benzylthio-2-(tri-n-butylstannyl) imidazo[5,1-b]thiazole were used as the starting compounds. Thus, 459 mg of 4-nitrobenzyl (1S,5R,6S)-2-(7-benzylthioimidazo[5,1-b]thiazol-2-yl)-6-((1R)-1-hydroxyethyl)-1-methyl-1-carbapen-2-em-3-carboxylate was prepared.

NMR (CDCl$_3$) δ: 1.24 (3H, d, J=7.5 Hz), 1.40 (3H, d, J=6.3 Hz), 3.3–3.4 (2H, m), 3.99 (2H, s), 4.25–4.4 (2H, m), 5.26 (1H, d, J=13.8 Hz), 5.51 (1H, d, J=13.8 Hz), 7.1–7.25 (5H, m), 7.67 (2H, d, J=8.4 Hz), 8.01 (1H, s), 8.24 (2H, d, J=8.4 Hz), 8.30 (1H, s)

b) Sodium (1S,5R,6S)-2-(7-benzylthioimidazo[5,1-b]thiazol-2-yl)-6-((1R)-1-hydroxyethyl)-1-methyl-1-carbapen-2-em-3-carboxylate The procedure of Example 1c) was repeated, except that 140 mg of 4-nitrobenzyl (1S,5R,6S)-2-(7- benzylthioimidazo[5,1-b]thiazol-2-yl)-6-((1R)-1-hydroxyethyl)-1-methyl-1-carbapen-2-em-3-carboxylate was used as the starting compound. Thus, 52.6 mg of the title compound was prepared.

NMR (D$_2$O) δ(HOD=4.80 ppm): 1.15 (3H, d, J=7.2 Hz), 1.30 (3H, d, J=6.3 Hz), 3.3–3.5 (2H, m), 3.86 (2H, s), 4.2–4.3 (2H, m), 6.95–7.05 (2H, m), 7.1–7.2 (3H, m), 7.71 (1H, s), 8.01 (1H, s)

Example 33

(1S,5R,6S)-6-((1R)-1-Hydroxyethyl)-2-[7-(2-isothioureidoethyl)thioimidazo[5,1-b]thiazol-2-yl]-1-methyl-1-carbapen-2-em-3-carboxylic acid 4-Nitrobenzyl (1S,5R,6S)-2-[7-(2-bromoethyl)thioimidazo[5,1-b]thiazol-2-yl]-6-((1R)-1-hydroxyethyl)-1-methyl-1-carbapen-2-em-3-carboxylate (128 mg) was dissolved in 3 ml of acetonitrile and 0.5 ml of DMF. Thiourea (222 mg) was added to the solution. The mixture was stirred at 50° C. for 18 hr. The reaction solution was concentrated under the reduced pressure. The residue was purified by column chromatography on Sephadex LH-20 (dichloromethane:methanol=1:1), followed by a reaction and purification in the same manner as in Example 1c). Thus, 14.5 mg of the title compound was prepared.

NMR (D$_2$O) δ(HOD=4.80 ppm): 1.24 (3H, d, J=7.2 Hz), 1.32 (3H, d, J=6.6 Hz), 3.05–3.15 (2H, m), 3.2–3.3 (2H, m), 3.5–3.6 (2H, m), 4.2–4.4 (2H, m), 7.88 (1H, s), 8.15 (1H, s)

Example 34

Sodium (1S,5R,6S)-6-((1R)-1-hydroxyethyl)-1-methyl-2-[7-(pyridin-2-yl)methylthioimidazo[5,1-b]thiazol-2-yl]-1-carbapen-2-em-3-carboxylate a) 4-Nitrobenzyl (1S,5R,6S)-6-((1R)-1-hydroxyethyl)-1-methyl-2-[7-(pyridin-2-yl)methylthioimidazo[5,1-b]thiazol-2-yl]-1-carbapen-2-em-3-carboxylate The procedure of Example 1a) was repeated, except that 807 mg of 4-nitrobenzyl (1R,3R,5R,6S)-6-((1R)-1-hydroxyethyl)-1-methyl-2-oxo-1-carbapenam-3-carboxylate and 1.255 g of 7-(pyridin-2-yl)methylthio-2-(tri-n-butylstannyl)imidazo[5,1-b]thiazole were used as the starting compounds. Thus, 149 mg of 4-nitrobenzyl (1S,5R,6S)-6-((1R)-1-hydroxyethyl)-1-methyl-2-[7-(pyridin-2-yl)methylthioimidazo[5,1-b]thiazol-2-yl]-1-carbapen-2-em-3-carboxylate was prepared.

NMR (CDCl$_3$) δ: 1.25 (3H, d, J=7.2 Hz), 1.40 (3H, d, J=6.3 Hz), 3.3–3.4 (2H, m), 4.13 (2H, s), 4.25–4.4 (2H, m), 5.26 (1H, d, J=13.8 Hz), 5.51 (1H, d, J=13.8 Hz), 7.1–7.25 (2H, m), 7.5–7.6 (1H, m), 7.67 (2H, d, J=8.7 Hz), 8.00 (1H, s), 8.24 (2H, d, J=8.7 Hz), 8.30 (1H, s), 8.45–8.5 (1H, m)

b) Sodium (1S,5R,6S)-6-((1R)-1-hydroxyethyl)-1-methyl-2-[7-(pyridin-2-yl)methylthioimidazo[5,1-b]thiazol-2-yl]-1-carbapen-2-em-3-carboxylate The procedure of Example 1c) was repeated, except that 86.6 mg of 4-nitrobenzyl (1S,5R,6S)-6-((1R)-1-hydroxyethyl)-1-methyl-2-[7-(pyridin-2-yl)methylthioimidazo[5,1-b]thiazol-2-yl]-1-carbapen-2-em-3-carboxylate was used as the starting compound. Thus, 32.5 mg of the title compound was prepared.

NMR (D$_2$O) δ(HOD=4.80 ppm): 1.18 (3H, d, J=7.2 Hz), 1.31 (3H, d, J=6.3 Hz), 3.4–3.5 (2H, m), 3.93 (2H, s), 4.2–4.3 (2H, m), 6.85–6.9 (1H, m), 7.2–7.25 (1H, m), 7.5–7.6 (1H, m), 7.77 (1H, s), 8.08 (1H, s), 8.25–8.3 (1H, m)

Example 35

Sodium (1S,5R,6S)-6-((1R)-1-hydroxyethyl)-1-methyl-2-[7-(pyridin-2-yl)thioimidazo[5,1-b]thiazol-2-yl]-1-carbapen-2-em-3-carboxylate a) 4-Nitrobenzyl (1S,5R,6S)-6-((1R)-1-hydroxyethyl)-1-methyl-2-[7-(pyridin-2-yl)thioimidazo[5,1-b]thiazol-2-yl]-1-carbapen-2-em-3-carboxylate The procedure of Example 1a) was repeated, except that 576 mg of 4-nitrobenzyl (1R,3R,5R,6S)-6-((1R)-1-hydroxyethyl)-1-methyl-2-oxo-1-carbapenam-3-carboxylate and 872 mg of 7-(pyridin-2-yl)thio-2-(tri-n-butylstannyl)imidazo[5,1-b]thiazole were used as the starting compounds. Thus, 112 mg of 4-nitrobenzyl (1S,5R,6S)-6-((1R)-1-hydroxyethyl)-1-methyl-2-[7-(pyridin-2-yl)thioimidazo[5,1-b]thiazol-2-yl]-1-carbapen-2-em-3-carboxylate was prepared.

NMR (CDCl$_3$) δ: 1.30 (3H, d, J=7.5 Hz), 1.39 (3H, d, J=6.3 Hz), 3.37 (1H, dd, J$_1$=6.6 Hz, J$_2$=2.7 Hz), 3.4–3.5 (1H, m), 4.25–4.4 (2H, m), 5.28 (1H, d, J=13.5 Hz), 5.52 (1H, d, J=13.5 Hz), 6.9–7.05 (2H, m), 7.4–7.5 (1H, m), 7.67 (2H, d, J=8.7 Hz), 8.16 (1H,s), 8.23 (2H, d, J=8.7 Hz), 8.37 (1H, s), 8.4–8.45 (1H, m)

b) Sodium (1S,5R,6S)-6-((1R)-1-hydroxyethyl)-1-methyl-2-[7-(pyridin-2-yl)thioimidazo[5,1-b]thiazol-2-yl]-1-carbapen-2-em-3-carboxylate The procedure of Example 1c) was repeated, except that 70 mg of 4-nitrobenzyl (1S,5R,6S)-6-((1R)-1-hydroxyethyl)-1-methyl-2-[7-(pyridin-2-yl)thioimidazo[5,1-b]thiazol-2-yl]-1-carbapen-2-em-3-carboxylate was used as the starting compound. Thus, 21.1 mg of the title compound was prepared.

NMR (D$_2$O) δ(HOD=4.80 ppm): 1.20 (3H, d, J=6.9 Hz), 1.31 (3H, d, J=6.6 Hz), 3.45–3.6 (2H, m), 4.2–4.35 (2H, m), 6.8–6.9 (1H, m), 7.1–7.2 (1H, m), 7.5–7.6 (1H, m), 7.96 (1H, s), 8.25 (1H, s), 8.25–8.3 (1H, m)

Example 36

(1S,5R,6S)-2-[7-(1-Carbamoylmethylpyridinium-2-yl)thioimidazo[5,1-b]thiazol-2-yl]-6-((1R)-1-hydroxyethyl)-1-methyl-1-carbapen-2-em-3-carboxylate (intramolecular salt)

4-Nitrobenzyl (1S,5R,6S)-6-((1R)-1-hydroxyethyl)-1-methyl-2-[7-(pyridin-2-yl)thioimidazo[5,1-b]thiazol-2-yl]-1-carbapen-2-em-3-carboxylate (42.2 mg) was dissolved in 2 ml of acetone. 2-Iodoacetamide (140 mg) was added to the solution. The mixture was stirred at 40° C. for 4 days. Ethyl acetate (4 ml) was added to the reaction solution, and the resultant precipitate was collected, and was reacted in the same manner as in Example 1c). The reaction product was purified by column chromatography on Cosmosil 40C$_{18}$-PREP (a 10 to 25% aqueous methanol solution). In this case, the first eluted fraction in two major products was collected to prepare 1.44 mg of the title compound.

NMR (D$_2$O) δ(HOD=4.80 ppm): 1.27 (3H, d, J=6.3 Hz), 1.33 (3H, d, J=6.3 Hz), 3.5–3.6 (2H, m), 4.25–4.4 (2H, m), 5.61 (2H, s), 7.3–7.4 (1H, m), 7.7–7.8 (1H, m), 8.05 (1H, s), 8.2–8.3 (1H, m), 8.40 (1H, s), 8.65–8.75 (1H, m)

Example 37

Sodium (1S,5R,6S)-2-[7-((2R)-2,3-dihydroxypropyl)thioimidazo[5,1-b]thiazol-2-yl]-6-((1R)-1-hydroxyethyl)-1-methyl-1-carbapen-2-em-3-carboxylate a) 4-Nitrobenzyl (1S,5R,6S)-2-[7-((2R)-3-azido-2-triethylsilyloxypropyl)thioimidazo[5,1-b]thiazol-2-yl]-6-((1R)-1-hydroxyethyl)-1-methyl-1-carbapen-2-em-3-carboxylate The procedure of Example 1a) was repeated, except that 582 mg of 4-nitrobenzyl (1R,3R,5R,6S)-6-((1R)-1-hydroxyethyl)-1-methyl-2-oxo-1-carbapenam-3-carboxylate and 1.11 g of 7-((2R)-3-azido-2-triethylsilyloxypropyl)thio-2-(tri-n-butylstannyl)imidazo[5, 1-b]thiazole were used as the starting compounds. Thus, 560 mg of 4-nitrobenzyl (1S,5R,6S)-2-[7-((2R)-3-azido-2-triethylsilyloxypropyl)thioimidazo[5,1-b]thiazol-2-yl]-6-((1R)-1-hydroxyethyl)-1-methyl-1-carbapen-2-em-3-carboxylate was prepared.

NMR (CDCl$_3$) δ: 0.55 (6H, q, J=7.4 Hz), 0.89 (9H, t, J=7.4 Hz), 1.31 (3H, d, J=7.2 Hz), 1.40 (3H, d, J=6.3 Hz), 2.9–3.0 (2H, m), 3.35–3.6 (4H, m), 3.9–4.0 (1H, m), 4.3–4.4 (2H, m), 5.28 (1H, d, J=13.5 Hz), 5.53 (1H, d, J=13.5 Hz), 7.68 (2H, d, J=8.7 Hz), 8.01 (1H, s), 8.25 (2H, d, J=8.7 Hz), 8.33 (1H, s)

b) 4-Nitrobenzyl (1S,5R,6S)-2-[7-((2R)-3-azido-2-hydroxypropyl)thioimidazo[5,1-b]thiazol-2-yl]-6-((1R)-1-hydroxyethyl)-1-methyl-1-carbapen-2-em-3-carboxylate 4-Nitrobenzyl (1S,5R,6S)-2-[7-((2R)-3-azido-2-triethylsilyloxypropyl)thioimidazo[5,1-b]thiazol-2-yl]-6-((1R)-1-hydroxyethyl)-1-methyl-1-carbapen-2-em-3-carboxylate (560 mg) was dissolved in 10 ml of THF and 10 ml of water. The solution was adjusted to pH 2.5 by the addition of 1 N hydrochloric acid. The mixture was stirred at room temperature for 30 min, and was then adjusted to pH 7.0 by the addition of an aqueous sodium hydrogencarbonate solution, followed by extraction with ethyl acetate twice. The organic layers were combined, were washed with brine, and were dried over anhydrous magnesium sulfate. The solvent was then removed by distillation under the reduced pressure. The residue was purified by column chromatography on silica gel (dichloromethane:methanol=20:1) to prepare 455 mg of 4-nitrobenzyl (1S,5R,6S)-2-[7-((2R)-3-azido-2-hydroxypropyl)thioimidazo[5,1-b]thiazol-2-yl]-6-((1R)-1-hydroxyethyl)-1-methyl-1-carbapen-2-em-3-carboxylate.

NMR (CDCl$_3$) δ: 1.31 (3H, d, J=7.5 Hz), 1.40 (3H, d, J=6.3 Hz), 2.8–3.0 (2H, m), 3.35–3.5 (4H, m), 4.0–4.1 (1H, m), 4.3–4.4 (2H, m), 5.05–5.15 (1H, m), 5.28 (1H, d, J=13.8 Hz), 5.52 (1H, d, J=13.8 Hz), 7.68 (2H, d, J=8.7 Hz), 8.02 (1H, s), 8.24 (2H, d, J=8.7 Hz), 8.28 (1H, s)

c) Sodium (1S,5R,6S)-2-[7-((2R)-2,3-dihydroxypropyl)thioimidazo[5,1-b]thiazol-2-yl]-6-((1R)-1-hydroxyethyl)-1-methyl-1-carbapen-2-em-3-carboxylate The procedure of Example 1c) was repeated, except that 115 mg of 4-nitrobenzyl (1S,5R,6S)-2-[7-((2R)-3-azido-2-hydroxypropyl)thioimidazo[5,1-b]thiazol-2-yl]-6-((1R)-1-hydroxyethyl)-1-methyl-1-carbapen-2-em-3-carboxylate was used as the starting compound for the reaction. The reaction product was purified by column chromatography on Cosmosil 40C$_{18}$-PREP (a 10 to 25% aqueous methanol solution). In this case, a fraction was collected which had been eluted first. Thus, 4.7 mg of the title compound was prepared.

NMR (D$_2$O) δ(HOD=4.80 ppm): 1.24 (3H, d, J=7.2 Hz), 1.32 (3H, d, J=6.3 Hz), 2.7–3.0 (2H, m), 3.45–3.75 (5H, m), 4.2–4.4 (2H, m), 7.86 (1H, s), 8.10 (1H, s)

Example 38

Sodium (1S,5R,6S)-6-((1R)-1-hydroxyethyl)-1-methyl-2-[7-(2-oxopropyl)thioimidazo[5,1-b]thiazol-2-yl]-1-carbapen-2-em-3-carboxylate A fraction was collected which had been eluted second in the column chromatography on Cosmosil 40C$_{18}$-PREP (a 10 to 25% aqueous methanol solution) in Example 37c). Thus, 2.6 mg of the title compound was prepared.

NMR (D$_2$O) δ(HOD=4.80 ppm): 1.24 (3H, d, J=7.5 Hz), 1.32 (3H, d, J=6.3 Hz), 2.33 (3H, s), 3.5–3.65 (4H, m), 4.2–4.35 (2H, m), 7.87 (1H, s), 8.09 (1H, s)

Example 39

Sodium (1S,5R,6S)-2-[7-((2R)-3-amino-2-hydroxypropyl)thioimidazo[5,1-b]thiazol-2-yl]-6-((1R)-1-hydroxyethyl)-1-methyl-1-carbapen-2-em-3-carboxylate A main product was collected which had been eluted lastly in the column chromatography on Cosmosil 40C$_{18}$-PREP (a 10 to 25% aqueous methanol solution) in Example 37c). Thus, 36.1 mg of the title compound was prepared.

NMR (D$_2$O) δ(HOD=4.80 ppm): 1.22 (3H, d, J=6.9 Hz), 1.31 (3H, d, J=6.3 Hz), 2.8–3.0 (3H, m), 3.2–3.3 (1H, m), 3.45–3.6 (2H, m), 3.8–3.95 (1H, m), 4.2–4.35 (2H, m), 7.81 (1H, s), 8.08 (1H, s)

Example 40

Sodium (1S,5R,6S)-6-((1R)-1-hydroxyethyl)-1-methyl-2-[7-(pyridin-4-yl)thioimidazo[5,1-b]thiazol-2-yl]-1-carbapen-2-em-3-carboxylate a) 4-Nitrobenzyl (1S,5R,6S)-6-((1R)-1-hydroxyethyl)-1-methyl-2-[7-(pyridin-4-yl)thioimidazo[5,-b]thiazol-2-yl]-1-carbapen-2-em-3-carboxylate The procedure of Example 1a) was repeated, except that 1.18 g of 4-nitrobenzyl (1R,3R,5R,6S)-6-((1R)-1-hydroxyethyl)-1-methyl-2-oxo-1-carbapenam-3-carboxylate and 1.78 g of 7-(pyridin-4-yl)thio-2-(tri-n-butylstannyl)imidazo[5,1-b]thiazole were used as the starting compounds. Thus, 93.1 mg of 4-nitrobenzyl (1S,5R,6S)-6-((1R)-1-hydroxyethyl)-1-methyl-2-[7-(pyridin-4-yl)thioimidazo[5,1-b]thiazol-2-yl]-1-carbapen-2-em-3-carboxylate was prepared.

NMR (CDCl$_3$) δ: 1.31 (3H, d, J=7.5 Hz), 1.39 (3H, d, J=6.3 Hz), 3.37 (1H, dd, J$_1$=6.6 Hz, J$_2$=2.7 Hz), 3.4–3.5 (1H, m), 4.25–4.35 (1H, m), 4.38 (1H, dd, J$_1$=9.6 Hz, J$_2$=2.7 Hz), 5.27 (1H, d, J=13.8 Hz), 5.53 (1H, d, J=13.8 Hz), 6.95–7.0 (1H, m), 7.67 (2H, d, J=8.7 Hz), 8.17 (1H, s), 8.23 (2H, d, J=8.7 Hz), 8.3–8.35 (1H, m), 8.38 (1H, s)

b) Sodium (1S,5R,6S)-6-((1R)-1-hydroxyethyl)-1-methyl-2-[7-(pyridin-4-yl)thioimidazo[5,1-b]thiazol-2-yl]-1-carbapen-2-em-3-carboxylate The procedure of Example 1c) was repeated, except that 93.1 mg of 4-nitrobenzyl (1S,5R,6S)-6-((1R)-1-hydroxyethyl)-1-methyl-2-[7-(pyridin-4-yl)thioimidazo[5,1-b]thiazol-2-yl]-1-carbapen-2-em-3-carboxylate was used as the starting compound. Thus, 33.8 mg of the title compound was prepared.

NMR (D$_2$O) δ(HOD=4.80 ppm): 1.24 (3H, d, J=6.9 Hz), 1.33 (3H, d, J=6.1 Hz), 3.45–3.6 (2H, m), 4.2–4.35 (2H, m), 7.0–7.05 (2H, m), 8.00 (1H, s), 8.15–8.2 (2H, m), 8.29 (1H, s)

Example 41

Sodium (1S,5R,6S)-6-((1R)-1-hydroxyethyl)-1-methyl-2-[7-(pyridin-4-yl)sulfonylimidazo[5,1-b]thiazol-2-yl]-1-carbapen-2-em-3-carboxylate a) 4-Nitrobenzyl (1S,5R,6S)-6-((1R)-1-hydroxyethyl)-1-methyl-2-[7-(pyridin-4-yl)sulfonylimidazo[5,1-b]thiazol-2-yl]-1-carbapen-2-em-3-carboxylate The procedure of Example 1a) was repeated, except that 503 mg of 4-nitrobenzyl (1R,3R,5R,6S)-6-((1R)-1-hydroxyethyl)-1-methyl-2-oxo-1-carbapenam-3-carboxylate and 808 mg of 7-(pyridin-4-yl)sulfonyl-2-(tri-n-butylstannyl)imidazo[5,1-b]thiazole were used as the starting compounds. Thus, 466 mg of 4-nitrobenzyl (1S,5R,6S)-6-((1R)-1-hydroxyethyl)-1-methyl-2-[7-(pyridin-4-yl)sulfonylimidazo[5,1-b]thiazol-2-yl]-1-carbapen-2-em-3-carboxylate was prepared.

NMR (CDCl$_3$) δ: 1.32 (3H, d, J=7.2 Hz), 1.40 (3H, d, J=6.3 Hz), 3.40 (1H, dd, J$_1$=6.6 Hz, J$_2$=2.7 Hz), 3.4–3.6 (1H, m), 4.3–4.4 (1H, m), 4.42 (1H, dd, J$_1$=9.6 Hz, J$_2$=2.7 Hz), 5.28 (1H, d, J=13.5 Hz), 5.52 (1H, d, J=13.5 Hz), 7.67 (2H, d, J=8.7 Hz), 7.85–7.9 (2H, m), 8.04 (1H, s), 8.23 (2H, d, J=8.7 Hz), 8.39 (1H, s), 8.9–8.95 (2H, m)

b) Sodium (1S,5R,6S)-6-((1R)-1-hydroxyethyl)-1-methyl-2-[7-(pyridin-4-yl)sulfonylimidazo[5,1-b]thiazol-2-yl]-1-carbapen-2-em-3-carboxylate The procedure of Example 1c) was repeated, except that 283 mg of 4-nitrobenzyl (1S,5R,6S)-6-((1R)-1-hydroxyethyl)-1-methyl-2-[7-(pyridin-4-yl)sulfonylimidazo[5,1-b]thiazol-2-yl]-1-carbapen-2-em-3-carboxylate was used as the starting compound. Thus, 133 mg of the title compound was prepared.

NMR (D$_2$O) δ(HOD=4.80 ppm): 1.20 (3H, d, J=6.9 Hz), 1.31 (3H, d, J=6.3 Hz), 3.4–3.6 (2H, m), 4.2–4.35 (2H, m), 7.86 (2H, d, J=5.7 Hz), 8.03 (1H, s), 8.22 (1H, s), 8.74 (2H, d, J=5.7 Hz)

Preparation Example 1

Preparation for Injections

Aseptical charging into vials was carried out so that each vial contained 1000 mg (potency) of the compound prepared in Example 3.

Preparation Example 2

Soft capsules for Rectal Administration

| Olive oil | 160 parts (potency) |
| Polyoxyethylene lauryl ether | 10 parts (potency) |
| Sodium hexametaphosphate | 5 parts (potency) |

The compound (250 parts (potency)) prepared in Example 3 was added to and homogeneously mixed with a homogeneous base comprising the above ingredients. The mixture was filled into soft capsules for rectal administration to provide 250 mg (potency) per capsule.

Test Example 1

Antimicrobial Activities

The minimum inhibiting concentrations (MIC, μg/ml) of representative compounds, among the novel carbapenem derivatives of the present invention, to various pathogenic bacteria were measured in accordance with the method described in CHEMOTHERAPY, vol. 16, No. 1, 99, 1968. The results are shown in Table 1. The culture medium for the measurement is Sensitivity Disk agar-N+5% Horse blood, and the amount of inoculants used is 10$^6$ CFU/ml.

TABLE 1

| Test organisms | Compound of Ex. 5 | Compound of Ex. 14 | Compound of Ex. 20 | Compound A | Compound B |
| --- | --- | --- | --- | --- | --- |
| S. aureus 209P JC-1 | <0.025 | <0.025 | <0.025 | <0.025 | <0.025 |
| S. aureus M 126* | 1.56 | 0.78 | 0.78 | 25 | 6.25 |
| S. epidermidis ATCC 14990 | <0.025 | <0.025 | <0.025 | <0.025 | <0.025 |
| E. hirae ATCC 8043 | 0.39 | 0.20 | 0.20 | 0.78 | 0.39 |
| E. faecalis W-73 | 0.20 | 0.20 | 0.20 | 0.78 | 0.39 |
| S. pneumoniae PRC 9** | 0.05 | 0.05 | 0.05 | 0.20 | 0.20 |
| B. catarrhalis W-0500 | 0.05 | 0.10 | 0.05 | 0.05 | 0.10 |
| H. influenzae PRC 2 | 0.05 | <0.025 | 0.05 | 0.78 | <0.025 |
| H. influenzae PRC 44 | 0.20 | 0.025 | 0.10 | 12.5 | 0.20 |
| E. coli NIHJ JC-2 | 0.10 | 1.56 | 0.20 | 0.10 | 0.20 |
| K. pneumoniae PC 1602 | 0.10 | 1.56 | 0.39 | 0.20 | 0.10 |
| P. vulgaris GN 7919 | 0.20 | 0.78 | 0.39 | 0.10 | 0.10 |
| C. freundii GN 346 | 1.56 | NT | 1.56 | 0.20 | 1.56 |

*Methicillin-hyperresistant strain
**Penicillin-hyperresistant strain
Compound A: Imipenem
Compound B: Sodium (1S,5R,6S)-6-((1R)-1-hydroxyethyl)-2-(imidazo[5,1-b]thiazol-2-yl)-1-methyl-1-carbapen-2-em-3-carboxylate The carbapenem derivatives represented by formula (I) according to the present invention have potent antimicrobial activities against MRSA, PRSP, and Influenzavirus, as well as various pathogenic bacteria including β-lactamase-producing bacteria.

Test Example 2

Acute toxicity test

The compound of Example 5 according to the present invention was intraveneously administered at a dose of 2000 mg/kg to mice (ICR, male) (one group consisting of three mice). As a result, all the mice survived.

What is claimed is:

1. A compound of formula (I) or a pharmaceutically acceptable salt thereof:

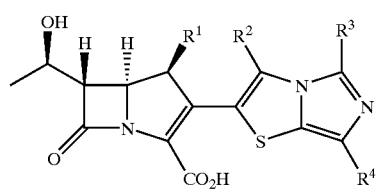

(I)

wherein
R¹ represents a hydrogen atom or methyl;
R² and R³, which may be the same or different, represent
a hydrogen atom,
a halogen atom,
lower alkyl on which one or more hydrogen atoms may be substituted by hydroxyl or amino,
lower alkylcarbonyl,
carbamoyl,
aryl, or
lower alkylthio; and
R⁴ represents
substituted lower alkylthio wherein one or more substituents of the alkyl portion, which may be the same or different, are selected from the group consisting of a halogen atom, nitro, azido, cyano, lower cycloalkyl, isothioureido, hydroxyl, lower alkoxy, phosphonoxy, formyl, lower alkylcarbonyl, arylcarbonyl, carboxy, lower alkoxycarbonyl, carbamoyl, N-lower alkylcarbamoyl, N,N-di-lower alkylcarbamoyl, amino, N-lower alkylamino, N,N-di-lower alkylamino, formylamino, lower alkylcarbonylamino, aminosulfonylamino, (N-lower alkylamino)sulfonylamino, (N,N-di-lower alkylamino)-sulfonylamino, formimidoylamino, acetimidoylamino, guanidino, aminosulfonyl, (N-lower alkylamino)sulfonyl, (N,N-di-lower alkylamino)sulfonyl, aryl, a monocyclic or bicyclic heterocyclic ring containing one or more hetero atoms, which may be the same or different, pyridinium-1-yl, 1-azonia-4-azabicyclo[2,2,2]oct-1-yl, and 4-lower alkyl-1,4-diazoniabicyclo[2,2,2]oct-1-yl wherein the lower alkyl portion may be substituted by one or more groups selected from the group consisting of a halogen atom, hydroxyl, carbamoyl, and amino,
lower cycloalkylthio wherein one or more hydrogen atoms of the cycloalkyl portion may be substituted by a group selected from the group consisting of a halogen atom, nitro, cyano, hydroxyl, carbamoyl, and amino,
$C_{2-4}$ alkenylthio,
$C_{2-4}$ alkynylthio,
substituted arylthio wherein one or more substituents of the aryl portion, which may be the same or different, are selected from the group consisting of a halogen atom, nitro, cyano, hydroxyl, carbamoyl, and amino,
thio substituted by a monocyclic or bicyclic heterocyclic ring containing one or more hetero atoms which may be the same or different, wherein, when the ring contains a nitrogen atom, lower alkyl optionally having carbamoyl may be attached to the nitrogen atom and the nitrogen atom may be in the form of a quaternary ammonium atom,
substituted lower alkylsulfinyl wherein one or more substituents of the alkyl portion, which may be the same or different, are selected from the group consisting of a halogen atom, hydroxyl, carbamoyl, and amino, substituted lower alkylsulfonyl wherein one or more substituents of the alkyl portion, which may be the same or different, are selected from the group consisting of a halogen atom, hydroxyl, carbamoyl, and amino, or
sulfonyl substituted by a monocyclic or bicyclic heterocyclic ring containing one or more hetero atoms which may be the same or different, wherein, when the ring contains a nitrogen atom, lower alkyl optionally having carbamoyl may be attached to the nitrogen atom and the nitrogen atom may be in the form of a quaternary ammonium atom
provided that, when R⁴ includes a quaternary ammonium atom, the quaternary ammonium atom forms an internal salt with the carboxyl group linked to the carbapenem ring.

2. The compound according to claim 1, wherein R⁴ represents substituted lower alkylthio,
thio substituted by a monocyclic or bicyclic heterocyclic ring containing one or more hetero atoms which may be the same or different,
substituted lower alkylsulfinyl,
substituted lower alkylsulfonyl, or
sulfonyl substituted by a monocyclic or bicyclic heterocyclic ring containing one or more hetero atoms which may be the same or different, wherein, when the ring contains a nitrogen atom, lower alkyl optionally having carbamoyl may be attached to the nitrogen atom and the nitrogen atom may be in the form of a quaternary ammonium atom.

3. The compound according to claim 1, wherein R⁴ represents
substituted lower alkylthio,
optionally substituted lower cycloalkylthio,
$C_{2-4}$ alkenylthio,
$C_{2-4}$ alkynylthio,
substituted arylthio,
thio substituted by a monocyclic or bicyclic heterocyclic ring containing one or more hetero atoms which may be the same or different,
substituted lower alkylsulfinyl, or
substituted lower alkylsulfonyl.

4. The compound according to claim 1, wherein
R¹ represents a hydrogen atom or methyl,
R² and R³, which may be the same or different, represent a hydrogen atom or lower alkylthio, and
R⁴ represents
substituted lower alkylthio wherein one or more substituents of the alkyl portion, which may be the same or different, are selected from the group consisting of a halogen atom, azido, isothioureido, hydroxyl, phosphonoxy, lower alkylcarbonyl, carbamoyl, amino, formylamino, aminosulfonylamino, (N,N-di-lower alkylamino)sulfonylamino, formimidoylamino, acetimidoylamino, guanidino, aryl, a pyridine ring, pyridinium-1-yl, 1-azonia-4-azabicyclo[2,2,2]oct-1-yl, and 4-lower alkyl-1,4-diazoniabicyclo[2,2,2]oct-1-yl in which lower alkyl may be substituted by one or more groups selected from the group consisting of a halogen atom, hydroxyl, carbamoyl, and amino,
thio substituted by a heterocyclic ring selected from the group consisting of pyrrolidine, piperidine, and pyridine, wherein lower alkyl optionally having carbamoyl may be attached to the nitrogen atom in the ring and the nitrogen atom may be in the form of a quaternary ammonium atom, lower alkylsulfinyl optionally substituted by hydroxyl lower alkylsulfonyl optionally substituted by hydroxyl, or sulfonyl substituted by a heterocyclic ring selected from the group consisting of pyrrolidine, piperidine, and pyridine, wherein lower alkyl optionally having carbamoyl may be attached to the nitrogen atom in the ring and the nitrogen atom may be in the form of a quaternary ammonium atom.

5. The compound according to claim 1, wherein $R^1$ represents a hydrogen atom or methyl, $R^2$ and $R^3$, which may be the same or different, represent a hydrogen atom or lower alkylthio, and $R^4$ represents substituted lower alkylthio wherein one or more substituents thereof are selected from the group consisting of a halogen atom, azido, isothioureido, hydroxyl, phosphonoxy, lower alkylcarbonyl, carbamoyl, amino, formylamino, aminosulfonylamino, (N,N-di-lower alkylamino)sulfonyl-amino, formimidoylamino, acetimidoylamino, guanidino, aryl, pyridyl, pyridinium-1-yl, 1-azonia-4-azabicyclo[2,2,2]oct-1-yl, and 4-lower alkyl-1,4-diazoniabicyclo [2,2,2]oct-1-yl wherein the lower alkyl portion may be substituted by one or more groups selected from the group consisting of a halogen atom, hydroxyl, carbamoyl, and amino.

6. The compound according to claim 1, wherein $R^1$ represents methyl and $R^2$ and $R^3$ represent a hydrogen atom.

7. The compound according to claim 1, wherein $R^1$ represents methyl, $R^2$ and $R^3$ represent a hydrogen atom and $R^4$ represents amino or guanidino-substituted lower alkylthio or pyrrolidinylthio.

8. The compound according to claim 1, wherein $R^1$ represents methyl, $R^2$ and $R^3$ represent a hydrogen atom and $R^4$ represents 2-aminoethylthio, 2-guanidinoethylthio, or (3 S)-pyrrolidin-3-ylthio.

9. A pharmaceutical composition, comprising as active ingredient the compound according to any one of claims 1 to 8, or a pharmaceutically acceptable salt thereof, and a pharmaceutically acceptable additive.

10. A method for the manufacture of an antibiotic preparation, which comprises mixing the compound according to any one of claims 1 to 8, or a pharmaceutically acceptable salt thereof, with a pharmaceutically acceptable additive.

11. A method for treating and/or preventing bacterial infectious diseases, comprising the step of administering an effective amount of the compound according to any one of claims 1 to 8, or a pharmaceutically acceptable salt thereof, for the treatment and/or prevention of bacterial infectious diseases, to a mammal including a human.

* * * * *

UNITED STATES PATENT AND TRADEMARK OFFICE
CERTIFICATE OF CORRECTION

PATENT NO. : 6,680,313 B2  Page 1 of 1
DATED : January 20, 2004
INVENTOR(S) : Yuko Kano et al.

It is certified that error appears in the above-identified patent and that said Letters Patent is hereby corrected as shown below:

<u>Title page,</u>
Item [75], Inventor, correct the spelling of the inventor to -- Katsuyoshi Iwamatsu --.

Signed and Sealed this

Thirteenth Day of April, 2004

JON W. DUDAS
*Acting Director of the United States Patent and Trademark Office*